United States Patent
Zergiebel et al.

(10) Patent No.: US 9,839,425 B2
(45) Date of Patent: Dec. 12, 2017

(54) ADAPTER ASSEMBLY FOR INTERCONNECTING ELECTROMECHANICAL SURGICAL DEVICES AND SURGICAL LOADING UNITS, AND SURGICAL SYSTEMS THEREOF

(71) Applicant: Covidien LP, Mansfield, MA (US)

(72) Inventors: Earl Zergiebel, Guilford, CT (US); David Chowaniec, Rocky Hill, CT (US); Ryan Williams, New Hartford, CT (US); Anand Subramanian, Stamford, CT (US); Paul Richard, Shelton, CT (US)

(73) Assignee: Covidien LP, Mansfield, MA (US)

( * ) Notice: Subject to any disclaimer, the term of this patent is extended or adjusted under 35 U.S.C. 154(b) by 368 days.

(21) Appl. No.: 14/672,973

(22) Filed: Mar. 30, 2015

(65) Prior Publication Data
US 2015/0374366 A1    Dec. 31, 2015

Related U.S. Application Data

(60) Provisional application No. 62/017,610, filed on Jun. 26, 2014.

(51) Int. Cl.
*F16H 25/20* (2006.01)
*A61B 17/068* (2006.01)
*A61B 17/072* (2006.01)
*A61B 17/00* (2006.01)

(52) U.S. Cl.
CPC ...... *A61B 17/068* (2013.01); *A61B 17/07207* (2013.01); *F16H 25/20* (2013.01); *A61B 2017/00017* (2013.01); *A61B 2017/0046* (2013.01); *A61B 2017/00398* (2013.01); *A61B 2017/00473* (2013.01); *A61B 2017/00477* (2013.01)

(58) Field of Classification Search
CPC ............ A61B 17/068; A61B 17/07207; A61B 2017/0046; F16H 25/20
See application file for complete search history.

(56) References Cited

U.S. PATENT DOCUMENTS

| | | |
|---|---|---|
| 2,777,340 A | 1/1957 | Hettwer et al. |
| 2,957,353 A | 10/1960 | Babacz |
| 3,111,328 A | 11/1963 | Di Rito et al. |

(Continued)

FOREIGN PATENT DOCUMENTS

| | | |
|---|---|---|
| AU | 2008229795 A1 | 4/2009 |
| CA | 2451558 A1 | 1/2003 |

(Continued)

OTHER PUBLICATIONS

European Search Report corresponding to EP 15 17 3803.6, completed Nov. 10, 2015 and dated Nov. 24, 2015; (6 pp).

(Continued)

*Primary Examiner* — David M Fenstermacher

(57) ABSTRACT

The present disclosure relates to adapter assemblies for use with and to electrically and mechanically interconnect electromechanical surgical devices and surgical loading units, and to surgical systems including hand held electromechanical surgical devices and adapter assemblies for connecting surgical loading units to the hand held electromechanical surgical devices.

20 Claims, 48 Drawing Sheets

(56) References Cited

U.S. PATENT DOCUMENTS

| | | | |
|---|---|---|---|
| 3,695,058 A | 10/1972 | Keith, Jr. | |
| 3,734,515 A | 5/1973 | Dudek | |
| 3,759,336 A | 9/1973 | Marcovitz et al. | |
| 4,162,399 A | 7/1979 | Hudson | |
| 4,504,227 A * | 3/1985 | Lohn | A61C 1/08 |
| | | | 433/126 |
| 4,606,343 A | 8/1986 | Conta et al. | |
| 4,705,038 A | 11/1987 | Sjostrom et al. | |
| 4,722,685 A | 2/1988 | de Estrada et al. | |
| 4,810,139 A * | 3/1989 | Regan | B23B 31/006 |
| | | | 279/101 |
| 4,823,807 A | 4/1989 | Russell et al. | |
| 4,874,181 A | 10/1989 | Hsu | |
| 5,129,118 A | 7/1992 | Walmesley | |
| 5,129,570 A | 7/1992 | Schulze et al. | |
| 5,152,744 A | 10/1992 | Krause et al. | |
| 5,301,061 A | 4/1994 | Nakada et al. | |
| 5,312,023 A | 5/1994 | Green et al. | |
| 5,326,013 A | 7/1994 | Green et al. | |
| 5,350,355 A | 9/1994 | Sklar | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,411,508 A | 5/1995 | Bessler et al. | |
| 5,413,267 A | 5/1995 | Solyntjes et al. | |
| 5,427,087 A | 6/1995 | Ito et al. | |
| 5,467,911 A | 11/1995 | Tsuruta et al. | |
| 5,476,379 A | 12/1995 | Disel | |
| 5,487,499 A | 1/1996 | Sorrentino et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,540,375 A | 7/1996 | Bolanos et al. | |
| 5,540,706 A | 7/1996 | Aust et al. | |
| 5,542,594 A | 8/1996 | McKean et al. | |
| 5,549,637 A | 8/1996 | Crainich | |
| 5,553,675 A | 9/1996 | Pitzen et al. | |
| 5,562,239 A | 10/1996 | Boiarski et al. | |
| 5,564,615 A | 10/1996 | Bishop et al. | |
| 5,609,560 A | 3/1997 | Ichikawa et al. | |
| 5,632,432 A | 5/1997 | Schulze et al. | |
| 5,647,526 A | 7/1997 | Green et al. | |
| 5,653,374 A | 8/1997 | Young et al. | |
| 5,658,300 A | 8/1997 | Bito et al. | |
| 5,667,517 A | 9/1997 | Hooven | |
| 5,693,042 A | 12/1997 | Boiarski et al. | |
| 5,704,534 A | 1/1998 | Huitema et al. | |
| 5,713,505 A | 2/1998 | Huitema | |
| 5,762,603 A | 6/1998 | Thompson | |
| 5,779,130 A | 7/1998 | Alesi et al. | |
| 5,782,396 A | 7/1998 | Mastri et al. | |
| 5,782,397 A | 7/1998 | Koukline | |
| 5,797,536 A | 8/1998 | Smith et al. | |
| 5,820,009 A | 10/1998 | Melling et al. | |
| 5,863,159 A | 1/1999 | Lasko | |
| 5,908,427 A | 6/1999 | McKean et al. | |
| 5,954,259 A | 9/1999 | Viola et al. | |
| 5,964,774 A | 10/1999 | McKean et al. | |
| 5,993,454 A | 11/1999 | Longo | |
| 6,010,054 A | 1/2000 | Johnson et al. | |
| 6,017,354 A | 1/2000 | Culp et al. | |
| 6,032,849 A | 3/2000 | Mastri et al. | |
| 6,045,560 A | 4/2000 | McKean et al. | |
| 6,090,123 A | 7/2000 | Culp et al. | |
| 6,126,651 A | 10/2000 | Mayer | |
| 6,129,547 A | 10/2000 | Cise et al. | |
| 6,165,169 A | 12/2000 | Panescu et al. | |
| 6,239,732 B1 | 5/2001 | Cusey | |
| 6,241,139 B1 | 6/2001 | Milliman et al. | |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,348,061 B1 | 2/2002 | Whitman | |
| 6,368,324 B1 | 4/2002 | Dinger et al. | |
| 6,371,909 B1 | 4/2002 | Hoeg et al. | |
| 6,434,507 B1 | 8/2002 | Clayton et al. | |
| 6,443,973 B1 | 9/2002 | Whitman | |
| 6,461,372 B1 | 10/2002 | Jensen et al. | |
| 6,488,197 B1 | 12/2002 | Whitman | |
| 6,491,201 B1 | 12/2002 | Whitman | |
| 6,533,157 B1 | 3/2003 | Whitman | |
| 6,537,280 B2 | 3/2003 | Dinger et al. | |
| 6,610,066 B2 | 8/2003 | Dinger et al. | |
| 6,611,793 B1 | 8/2003 | Burnside et al. | |
| 6,645,218 B1 | 11/2003 | Cassidy et al. | |
| 6,654,999 B2 | 12/2003 | Stoddard et al. | |
| 6,698,643 B2 | 3/2004 | Whitman | |
| 6,699,177 B1 | 3/2004 | Wang et al. | |
| 6,716,233 B1 | 4/2004 | Whitman | |
| 6,743,240 B2 | 6/2004 | Smith et al. | |
| 6,783,533 B2 | 8/2004 | Green et al. | |
| 6,792,390 B1 | 9/2004 | Burnside et al. | |
| 6,793,652 B1 | 9/2004 | Whitman et al. | |
| 6,817,508 B1 | 11/2004 | Racenet et al. | |
| 6,830,174 B2 | 12/2004 | Hillstead et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,899,538 B2 | 5/2005 | Matoba | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,981,628 B2 | 1/2006 | Wales | |
| 6,981,941 B2 | 1/2006 | Whitman et al. | |
| 6,986,451 B1 | 1/2006 | Mastri et al. | |
| 6,988,649 B2 | 1/2006 | Shelton, IV et al. | |
| 7,032,798 B2 | 4/2006 | Whitman et al. | |
| RE39,152 E | 6/2006 | Aust et al. | |
| 7,055,731 B2 | 6/2006 | Shelton, IV et al. | |
| 7,059,508 B2 | 6/2006 | Shelton, IV et al. | |
| 7,077,856 B2 | 7/2006 | Whitman | |
| 7,111,769 B2 | 9/2006 | Wales et al. | |
| 7,122,029 B2 | 10/2006 | Koop et al. | |
| 7,140,528 B2 | 11/2006 | Shelton, IV | |
| 7,143,923 B2 | 12/2006 | Shelton, IV et al. | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,172,104 B2 | 2/2007 | Scirica et al. | |
| 7,225,964 B2 | 6/2007 | Mastri et al. | |
| 7,238,021 B1 | 7/2007 | Johnson | |
| 7,246,734 B2 | 7/2007 | Shelton, IV | |
| 7,328,828 B2 | 2/2008 | Ortiz et al. | |
| 7,364,061 B2 | 4/2008 | Swayze et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,407,078 B2 | 8/2008 | Shelton, IV et al. | |
| 7,416,101 B2 | 8/2008 | Shelton, IV et al. | |
| 7,419,080 B2 | 9/2008 | Smith et al. | |
| 7,422,139 B2 | 9/2008 | Shelton, IV et al. | |
| 7,431,189 B2 | 10/2008 | Shelton, IV et al. | |
| 7,441,684 B2 | 10/2008 | Shelton, IV et al. | |
| 7,448,525 B2 | 11/2008 | Shelton, IV et al. | |
| 7,464,846 B2 | 12/2008 | Shelton, IV et al. | |
| 7,464,847 B2 | 12/2008 | Viola et al. | |
| 7,464,849 B2 | 12/2008 | Shelton, IV et al. | |
| 7,481,347 B2 | 1/2009 | Roy | |
| 7,481,824 B2 | 1/2009 | Boudreaux et al. | |
| 7,487,899 B2 | 2/2009 | Shelton, IV et al. | |
| 7,549,564 B2 | 6/2009 | Boudreaux | |
| 7,565,993 B2 | 7/2009 | Milliman et al. | |
| 7,568,603 B2 | 8/2009 | Shelton, IV et al. | |
| 7,575,144 B2 | 8/2009 | Ortiz et al. | |
| 7,588,175 B2 | 9/2009 | Timm et al. | |

(56) References Cited

U.S. PATENT DOCUMENTS

| | | |
|---|---|---|
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,819,896 B2 | 10/2010 | Racenet |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2007/0023476 A1 | 2/2007 | Whitman et al. |
| 2007/0023477 A1* | 2/2007 | Whitman .......... A61B 17/07207 227/175.1 |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0118315 A1* | 5/2008 | Brunson .............. B23B 31/008 408/204 |
| 2008/0146353 A1* | 6/2008 | Boffelli .................. F16H 48/08 464/29 |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |

(56) References Cited

U.S. PATENT DOCUMENTS

| | | |
|---|---|---|
| 2009/0182193 A1 | 7/2009 | Whitman et al. |
| 2009/0194954 A1* | 8/2009 | Hsu .................. B23B 51/126 279/144 |
| 2009/0209990 A1 | 8/2009 | Yates et al. |
| 2009/0254094 A1 | 10/2009 | Knapp et al. |
| 2009/0261539 A1* | 10/2009 | Paulsen ............ B23B 31/1071 279/145 |
| 2009/0273146 A1* | 11/2009 | Dezheng ............... B23D 51/10 279/78 |
| 2010/0056986 A1* | 3/2010 | Allen ................. A61F 9/00745 604/22 |
| 2010/0069942 A1 | 3/2010 | Shelton, IV |
| 2010/0081108 A1* | 4/2010 | Webster ............ A61C 17/0202 433/80 |
| 2010/0089974 A1* | 4/2010 | Shelton, IV ..... A61B 17/07207 227/180.1 |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2676615 A2 | 12/2013 |
| EP | 2881046 A2 | 6/2015 |
| ES | 2333509 A1 | 2/2010 |
| JP | 08-038488 | 2/1996 |
| JP | 2005-125075 A | 5/2005 |
| KR | 20120022521 A | 3/2012 |
| WO | 99/15086 A1 | 4/1999 |
| WO | 00/72760 A1 | 12/2000 |
| WO | 00/72765 A1 | 12/2000 |
| WO | 03/000138 A2 | 1/2003 |
| WO | 03/026511 A1 | 4/2003 |

(56) References Cited

FOREIGN PATENT DOCUMENTS

| WO | 03/030743 | A2 | 4/2003 |
|---|---|---|---|
| WO | 03065916 | A1 | 8/2003 |
| WO | 03/077769 | A1 | 9/2003 |
| WO | 03/090630 | A2 | 11/2003 |
| WO | 2004/107989 | A1 | 12/2004 |
| WO | 2006/042210 | A2 | 4/2006 |
| WO | 2007016290 | A2 | 2/2007 |
| WO | 2007/026354 | A1 | 3/2007 |
| WO | 2007137304 | A2 | 11/2007 |
| WO | 2008/131362 | A2 | 10/2008 |
| WO | 2008/133956 | A2 | 11/2008 |
| WO | 2009/039506 | A1 | 3/2009 |
| WO | 2007014355 | A3 | 4/2009 |
| WO | 2009/132359 | A2 | 10/2009 |
| WO | 2009/143092 | A1 | 11/2009 |
| WO | 2009/149234 | A1 | 12/2009 |
| WO | 2011/108840 | A2 | 9/2011 |
| WO | 2012040984 | A1 | 4/2012 |

OTHER PUBLICATIONS

Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.

* cited by examiner

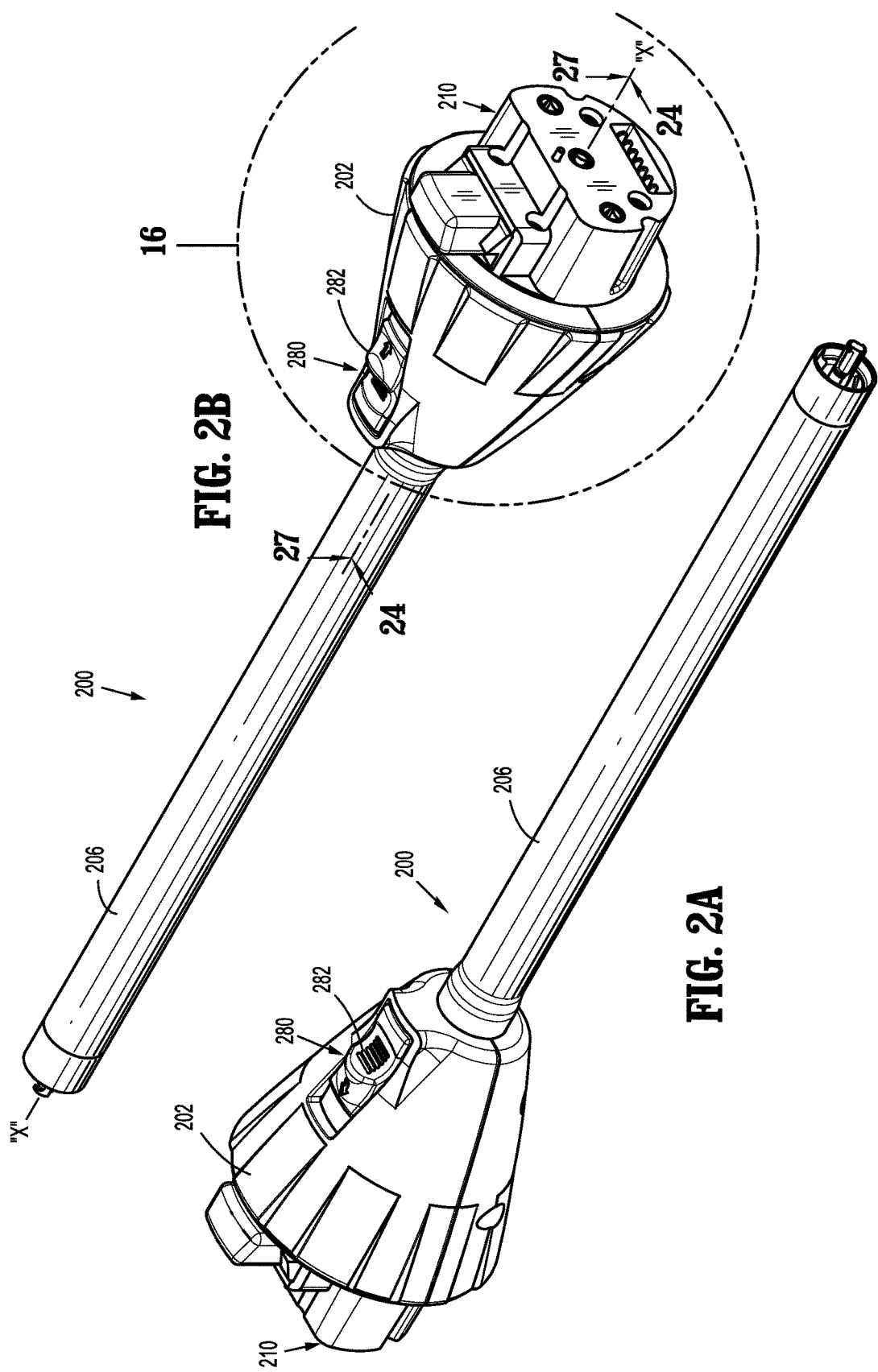

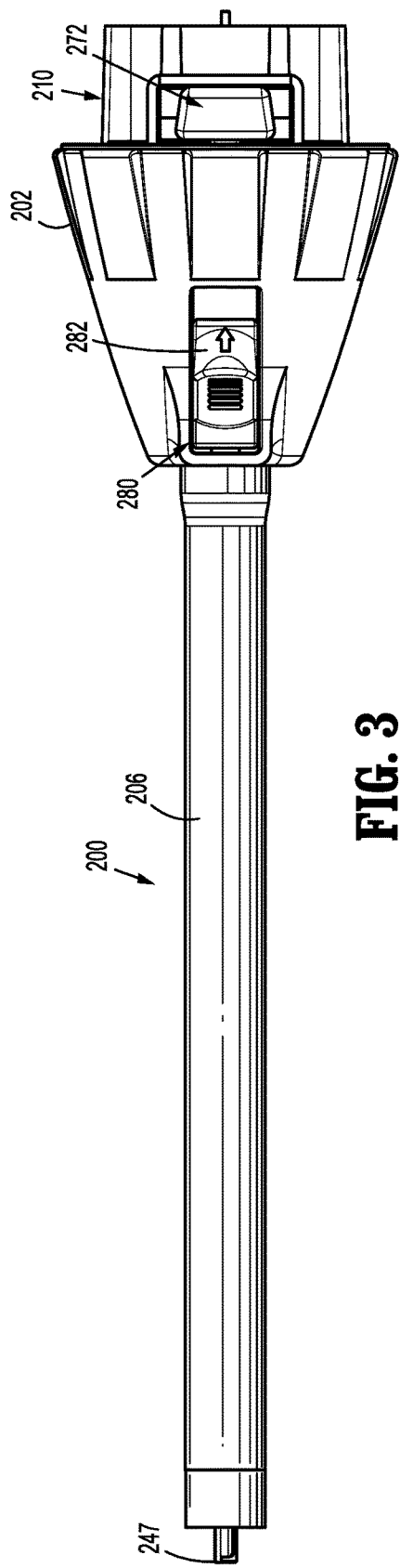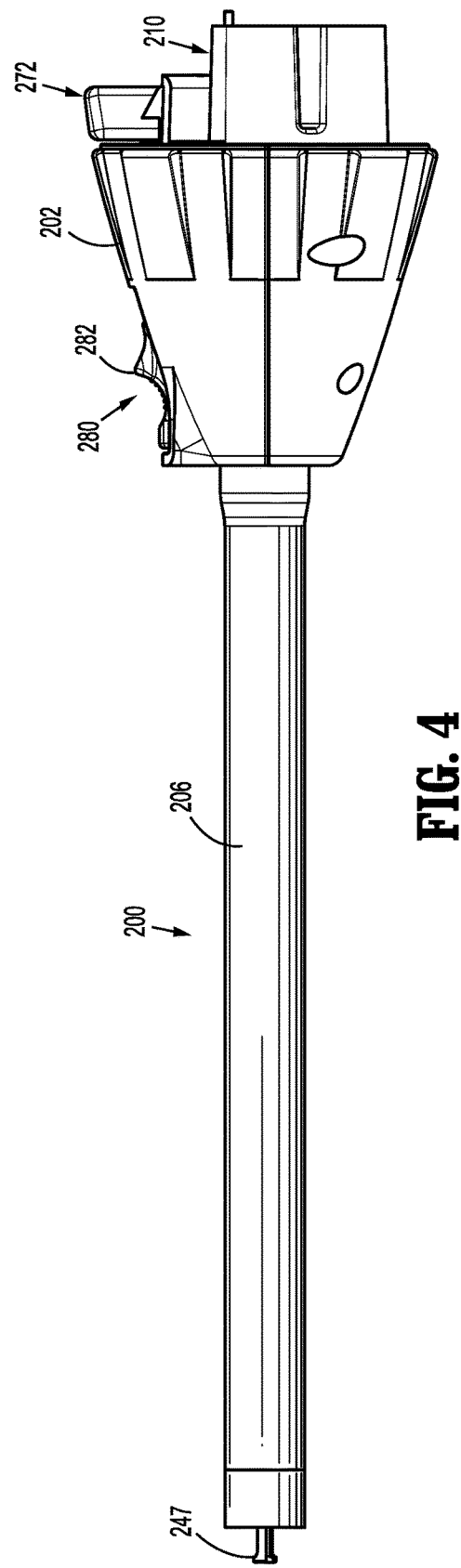
FIG. 3
FIG. 4

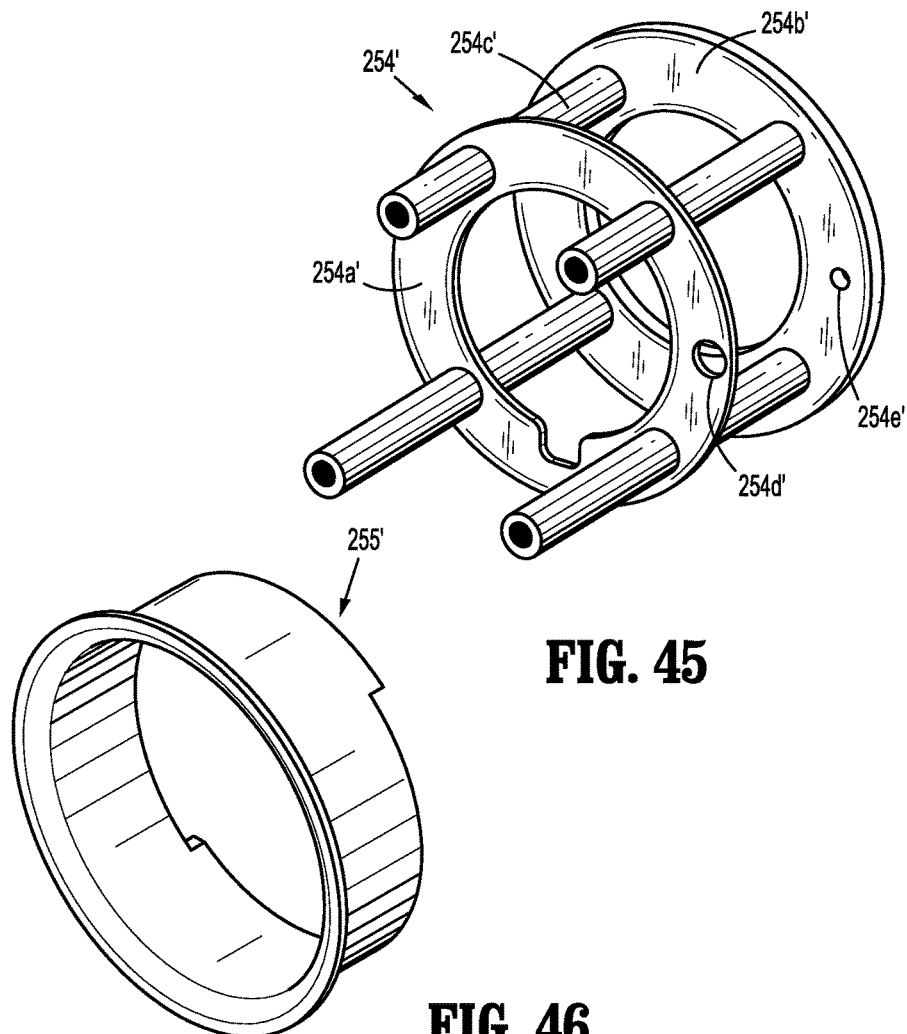
FIG. 45
FIG. 46
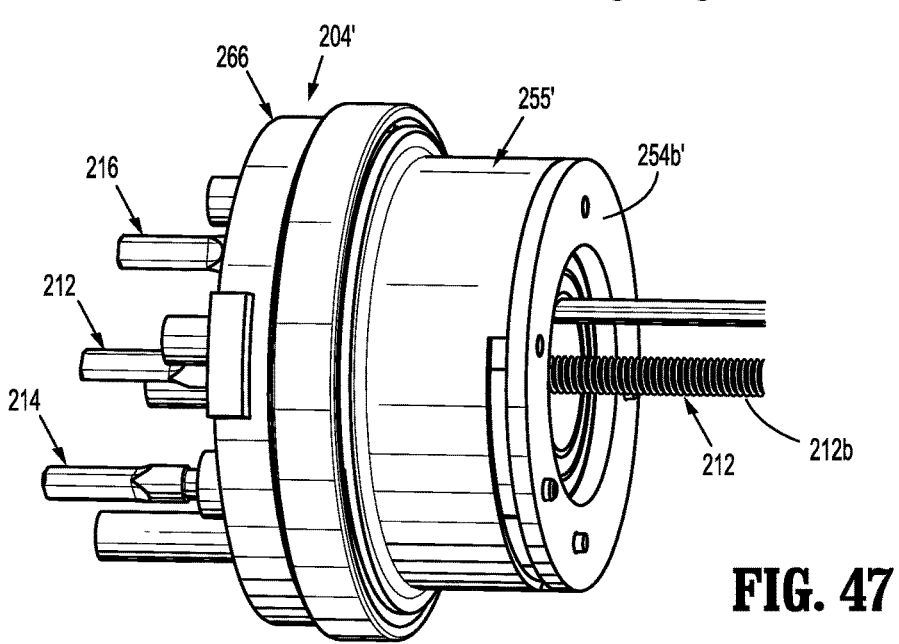
FIG. 47

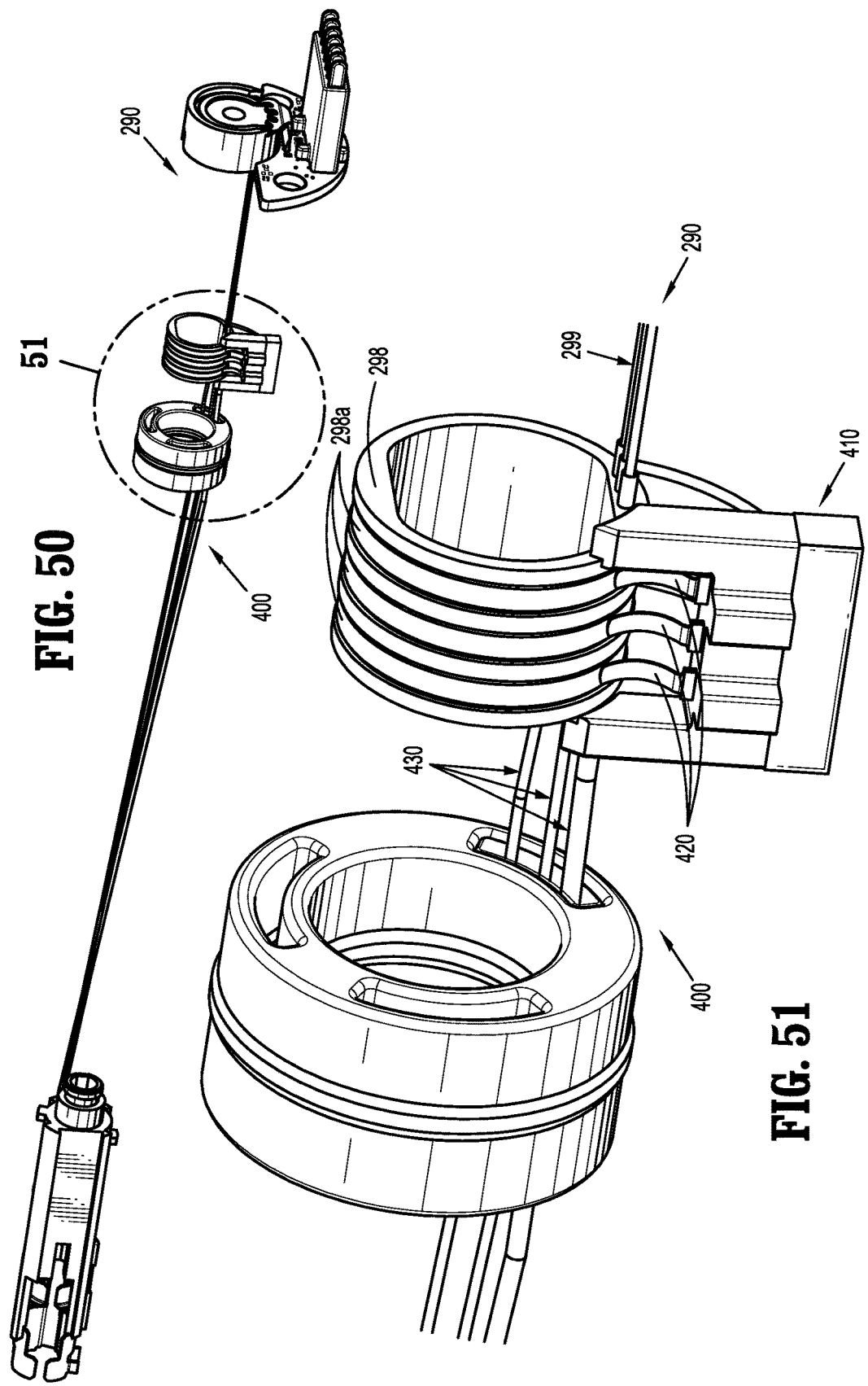

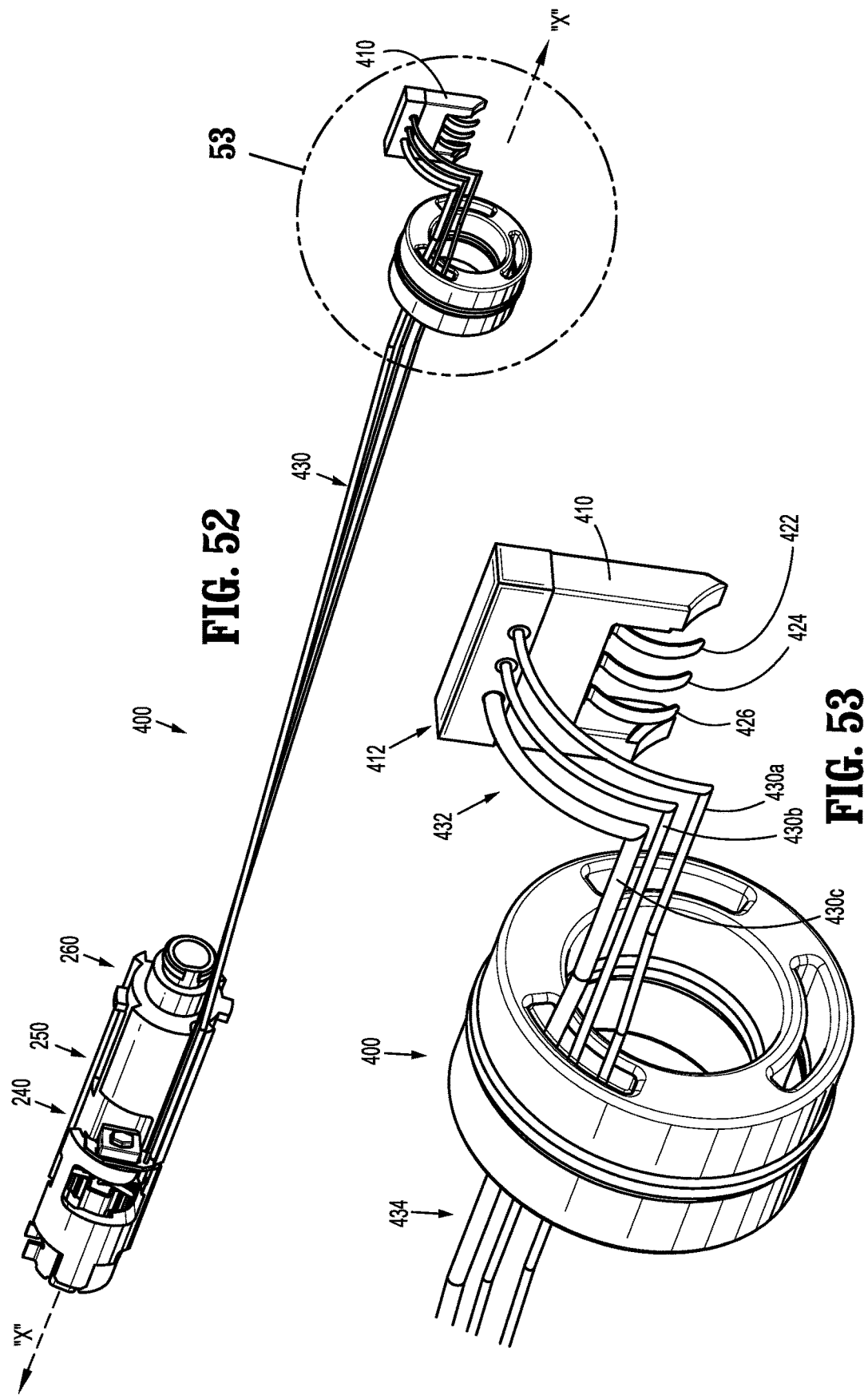

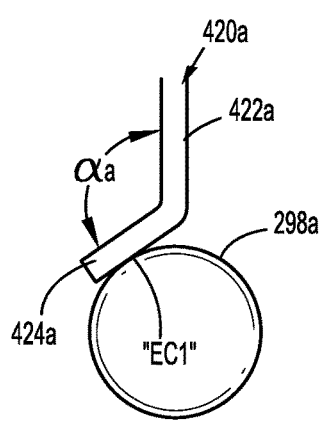 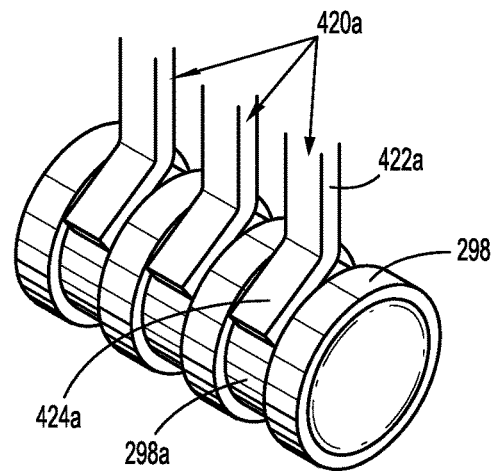
FIG. 56A    FIG. 56B
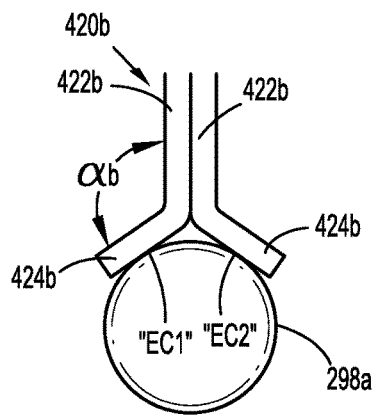 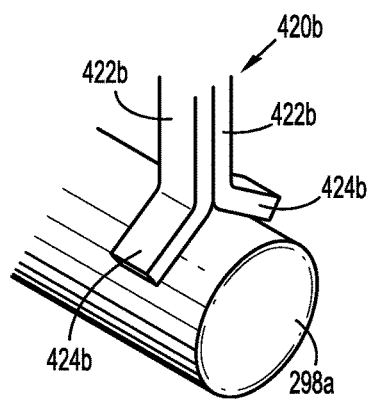
FIG. 57A    FIG. 57B
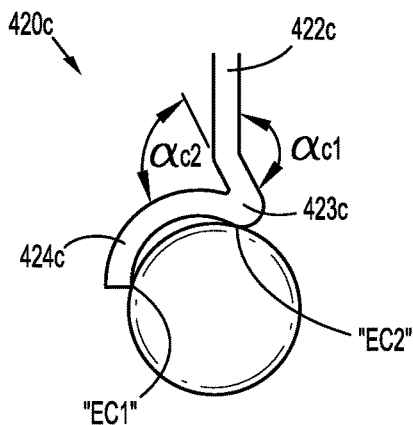 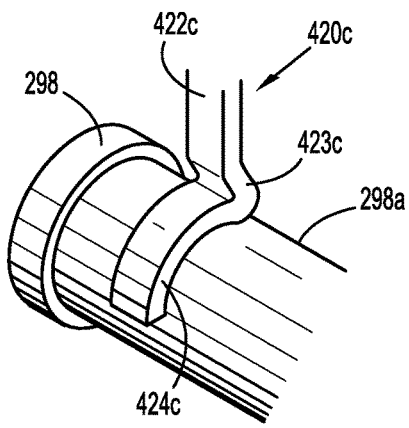
FIG. 58A    FIG. 58B

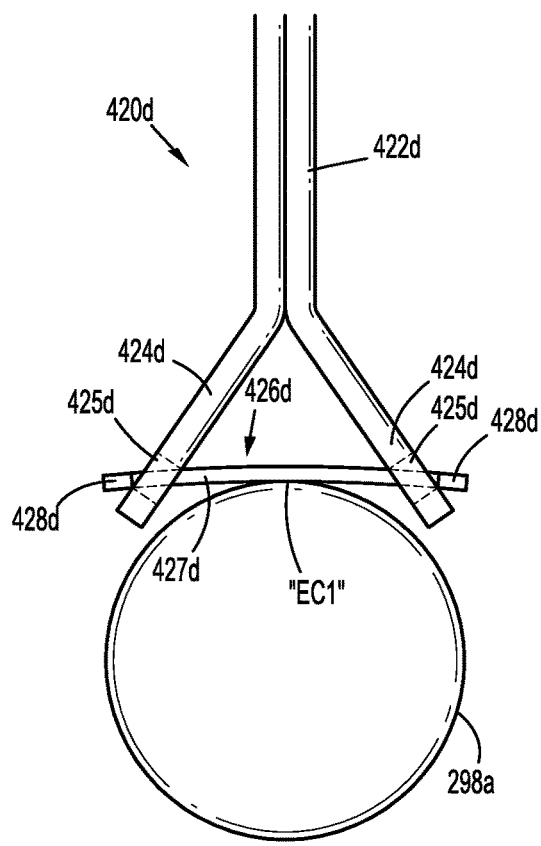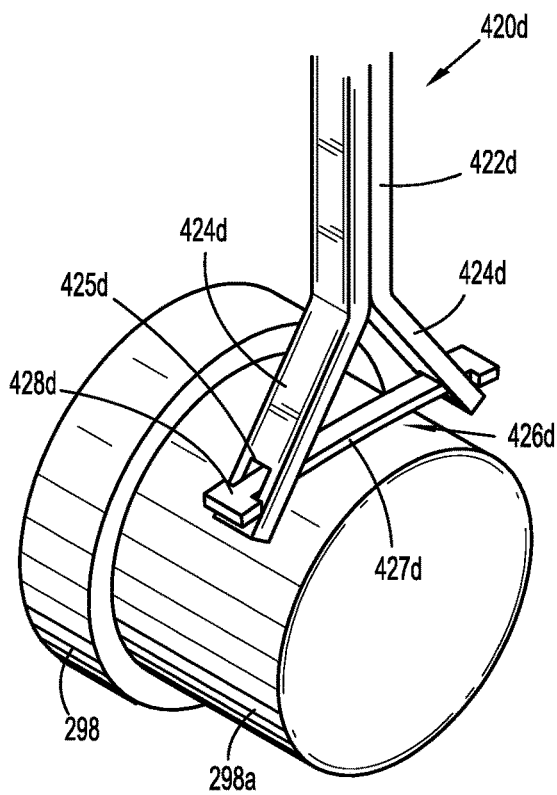
FIG.59A  FIG. 59B
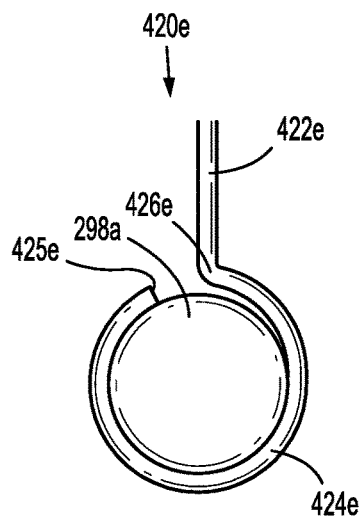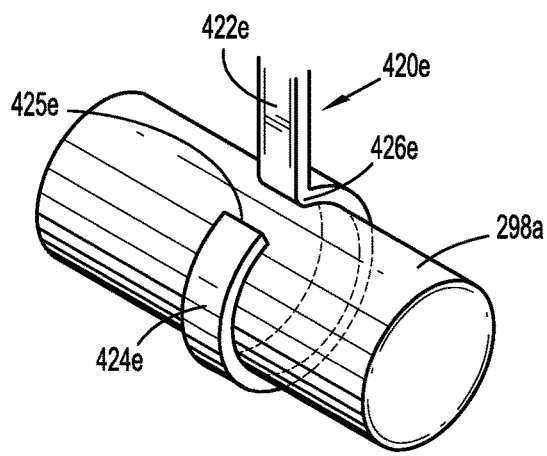
FIG.60A  FIG. 60B

ADAPTER ASSEMBLY FOR INTERCONNECTING ELECTROMECHANICAL SURGICAL DEVICES AND SURGICAL LOADING UNITS, AND SURGICAL SYSTEMS THEREOF

CROSS-REFERENCE TO RELATED APPLICATIONS

This application claims the benefit of and priority to U.S. Provisional Patent Application No. 62/017,610, filed Jun. 26, 2014, the entire disclosure of which is incorporated by reference herein.

BACKGROUND

1. Technical Field

The present disclosure relates to adapter assemblies for use in surgical systems. More specifically, the present disclosure relates to adapter assemblies for use with and to electrically and mechanically interconnect electromechanical surgical devices and surgical loading units, and to surgical systems including hand held electromechanical surgical devices and adapter assemblies for connecting surgical loading units to the hand held electromechanical surgical devices.

2. Background of Related Art

A number of surgical device manufacturers have developed product lines with proprietary drive systems for operating and/or manipulating electromechanical surgical devices. In many instances the electromechanical surgical devices include a handle assembly, which is reusable, and disposable loading units and/or single use loading units or the like that are selectively connected to the handle assembly prior to use and then disconnected from the handle assembly following use in order to be disposed of or in some instances sterilized for re-use.

In certain instances, an adapter assembly is used to interconnect an electromechanical surgical device with any one of a number of surgical loading units to establish a mechanical and/or electrical connection therebetween. Due to the complexity of the adapter assembly and the electromechanical surgical device, it is important to ensure that all electrical and mechanical connections therebetween can be easily, reliably and repeatedly accomplished.

Accordingly, a need exists for an adapter assembly that provides a robust way of electromechanically interconnecting with the surgical device.

SUMMARY

The present disclosure relates to adapter assemblies for use with and to electrically and mechanically interconnect electromechanical surgical devices and surgical loading units, and to surgical systems including hand held electromechanical surgical devices and adapter assemblies for connecting surgical loading units to the hand held electromechanical surgical devices.

According to an aspect of the present disclosure, an adapter assembly for selectively interconnecting a surgical loading unit that is configured to perform a function and a surgical device that is configured to actuate the loading unit, is provided. The loading unit may include at least one axially translatable drive member, and the surgical device may include at least one rotatable drive shaft. The adapter assembly includes a housing configured and adapted for connection with the surgical device and to be in operative communication with each rotatable drive shaft of the surgical device; an outer tube having a proximal end supported by the housing and a distal end configured and adapted for connection with the loading unit, wherein the distal end of the outer tube is in operative communication with each of the axially translatable drive member of the loading unit; the force/rotation transmitting/converting assembly for interconnecting a respective one drive shaft of the surgical device and a respective one axially translatable drive member of the loading unit; and an electrical assembly supported within at least one of the housing and the outer tube. The electrical assembly includes a proximal electrical assembly and a distal electrical assembly. The proximal electrical assembly is configured to electrically communicate with the surgical device. The proximal electrical assembly is rotatably fixed with respect to the surgical device, and the proximal electrical assembly includes a plurality of electrical contact rings disposed around a slip ring. The distal electrical assembly is disposed in electrical communication with the loading unit, and is rotatable with respect to the proximal electrical assembly. The distal electrical assembly includes a plurality of electrical contacts disposed in mechanical cooperation with a contact housing. Each electrical contact is configured to contact and maintain an electrical connection with one of the plurality of electrical contact rings of the proximal electrical assembly during rotation of the distal electrical assembly with respect to the proximal electrical assembly.

In disclosed embodiments, each electrical contact of the distal electrical assembly is curved along at least a majority of its length. It is further disclosed that each electrical contact of the distal electrical assembly includes a continuous curve in a first direction, and the plurality of electrical contact rings of the proximal electrical assembly are curved in a second direction. Here, the first and second directions are opposite from each other.

It is further disclosed that each electrical contact of the distal electrical assembly includes a leg and a foot, with the leg extending from the contact housing, and the foot extending at an angle from the leg. A portion of the foot configured to contact one of the plurality of electrical contact rings. The angle is between about 100° and about 160°.

The present disclosure also includes embodiments where each electrical contact of the distal electrical assembly includes a leg and two feet. The leg extends from the contact housing, each foot extends at an angle from the leg in opposite directions, and a portion of each foot is configured to contact one of the plurality of electrical contact rings. The angle is between about 100° and about 160°.

In disclosed embodiments, each electrical contact of the distal electrical assembly includes a leg, an ankle and an arcuate foot. The leg extends from the contact housing, the ankle extends at a first angle from the leg, and the arcuate foot extends at a second angle from the ankle. At least two portions of the arcuate foot are configured to contact one of the plurality of electrical contact rings. The first angle is between about 150° and about 175°, and the second angle is between about 10° and about 60°. Here, it is further disclosed that the arcuate foot includes a radius of curvature that is less than or equal to a radius of curvature of the plurality of electrical contact rings.

It is further disclosed that each electrical contact of the distal electrical assembly includes a leg, two feet extending from the leg in an opposite directions, and a flexible contact extending between the two feet. At least a portion of the flexible contact is configured to contact one of the plurality of electrical contact rings. Here, it is disclosed that the flexible contact is movable with respect to at least one foot.

In disclosed embodiments, each electrical contact of the distal electrical assembly includes a leg and a ring. The leg extends from the contact housing, and the ring extends from the leg. The ring is configured to contact one of the plurality of electrical contact rings in an arc of greater than 180°. Here, it is disclosed that the ring forms between about 180° and about 360° of a circle.

The present disclosure also includes embodiments where the contact housing includes a proximal leg configured to engage a proximal-most edge of the slip ring, and a distal leg configured to engage a distal-most edge of the slip ring. Here, it is disclosed that each leg of the contact housing includes a stepped portion. At least part of the stepped portion is configured to engage a radially-outermost portion of the slip ring.

In disclosed embodiments, the distal electrical assembly further includes a guide configured to help maintain a position of the contact housing with respect to the slip ring. Here, it is disclosed that the guide is configured to help maintain a longitudinal position and a radial position of the contact housing with respect to the slip ring. It is further disclosed that the guide includes an opening for receiving at least a portion of the contact housing therein, and that the guide includes a flexible member for extending between a pair of projections of the contact housing and for abutting a radially-outer surface of at least one of the projections of the contact housing. Additionally, embodiments disclose that the guide includes a first post extending adjacent a first portion of the opening for extending between a pair of projections of the contact housing, and that the guide includes a second post extending adjacent a second portion of the opening for engaging a portion of the contact housing. The first portion and the second portion are on opposite sides of the opening. The disclosure also includes that the contact housing includes at least one projection, and that the guide includes at least one flexible tab for engaging a radially-outer surface of the at least one projection of the contact housing. Further, it is disclosed that the contact housing includes at least two projections, and that the guide includes at least two flexible tabs. Each flexible tab is configured to engage a radially-outer surface of one of the at least two projections of the contact housing.

BRIEF DESCRIPTION OF THE DRAWINGS

Embodiments of the present disclosure are described herein with reference to the accompanying drawings, wherein:

FIG. 2A is a front, perspective view of the adapter assembly of the present disclosure;

FIG. 2B is a rear, perspective view of the adapter assembly of FIG. 2A;

FIG. 3 is a top plan view of the adapter assembly of FIGS. 2A and 2B;

FIG. 4 is a side, elevational view of the adapter assembly of FIGS. 2A and 2B;

FIG. 45 is a perspective view of a bracket assembly of the inner housing assembly of FIGS. 43 and 44;

FIG. 46 is a perspective view of a reinforcing sleeve for use with the inner housing assembly of FIGS. 43 and 44;

FIG. 47 is a perspective view of the inner housing assembly of FIGS. 43 and 44, illustrating the reinforcing sleeve of FIG. 46 supported thereon;

FIG. 50 is a perspective view of proximal and distal electrical assemblies of the adapter assembly of FIG. 49;

FIG. 51 is an enlarged view of the area of detail indicated in FIG. 50 showing engagement between the proximal and distal electrical assemblies of FIG. 50;

FIG. 52 is a perspective view of the distal electrical assembly of FIGS. 49 and 50;

FIG. 53 is an enlarged view of the area of detail indicated in FIG. 52;

FIGS. 56A-60A are side views of the proximal electrical assembly and various embodiments of the portion of the distal electrical assembly that engages the proximal electrical assembly;

FIGS. 56B-60B are perspective views of FIGS. 56A-60A, respectively;

DETAILED DESCRIPTION OF EMBODIMENTS

Figure 1A:
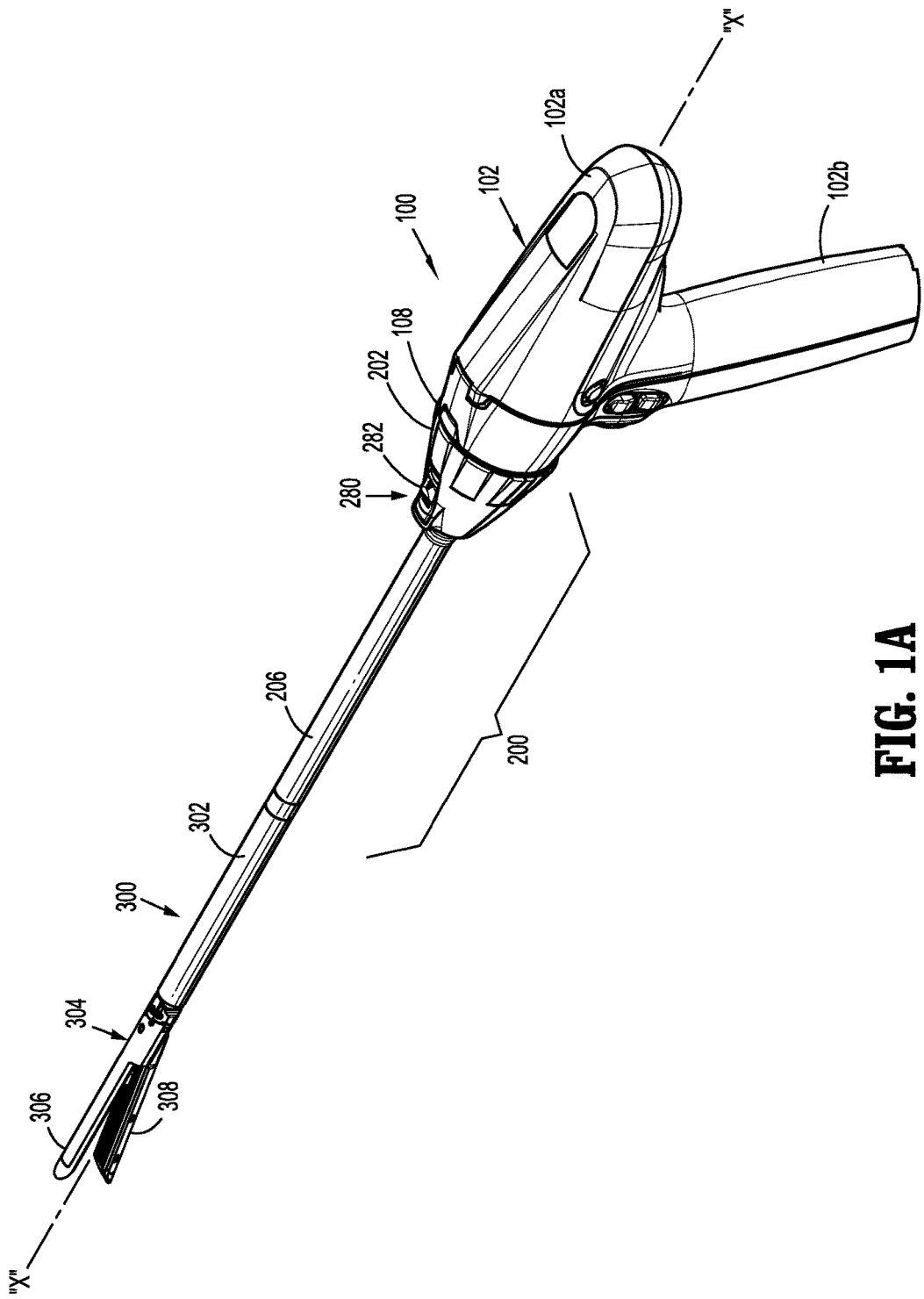
FIG. 1A is a perspective view of an adapter assembly, in accordance with an embodiment of the present disclosure, interconnected between an exemplary electromechanical surgical device and an end effector assembly.

Embodiments of the presently disclosed surgical devices, adapter assemblies, and loading unit detection assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

A surgical device, in accordance with an embodiment of the present disclosure, is generally designated as 100, and is in the form of a powered hand held electromechanical instrument configured for selective attachment thereto of a plurality of different end effectors that are each configured for actuation and manipulation by the powered hand held electromechanical surgical instrument.

Figure 48:
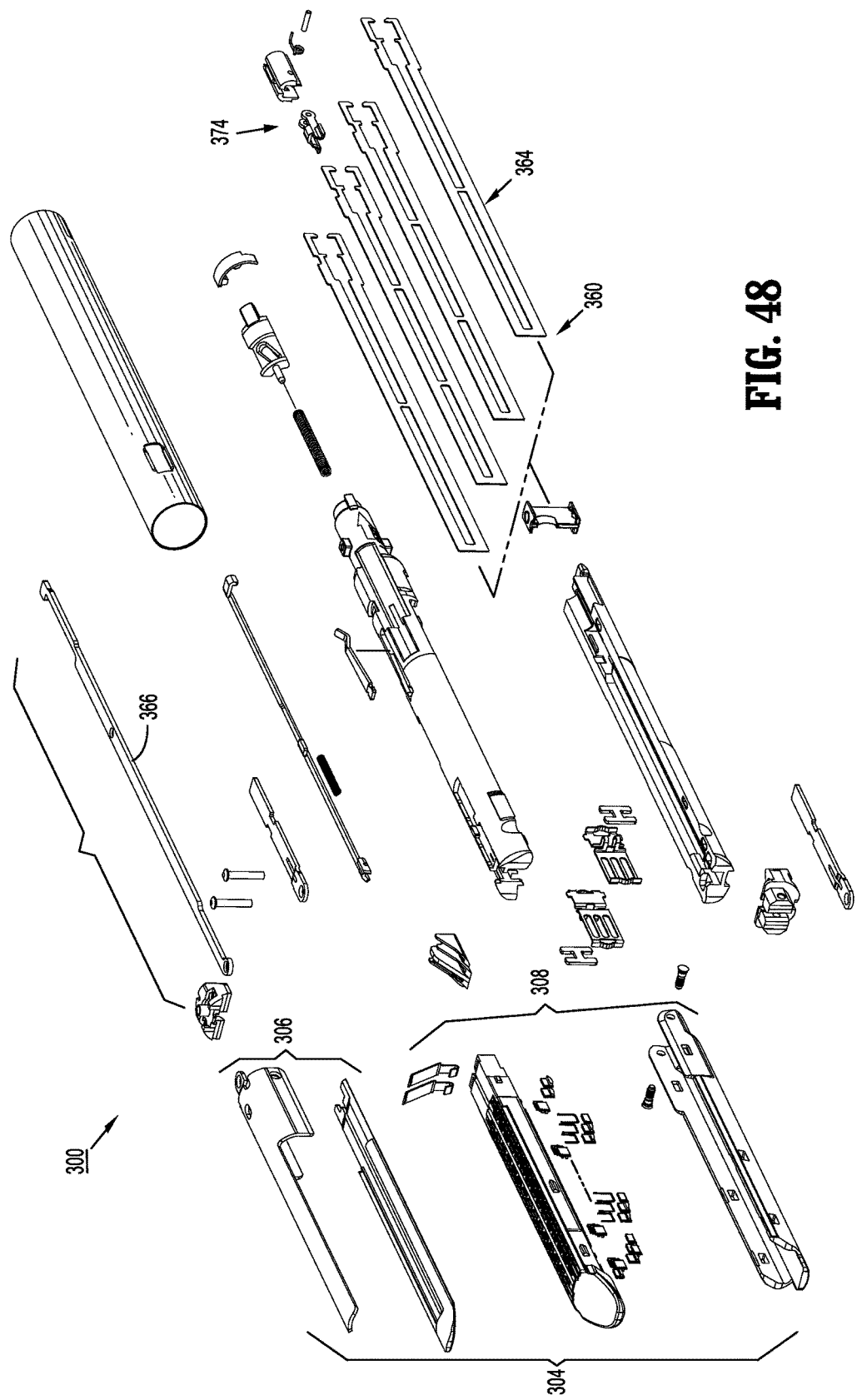
FIG. 48 is a perspective view, with parts separated, of an exemplary loading unit for use with the surgical device and the adapter of the present disclosure.
Figure 49:
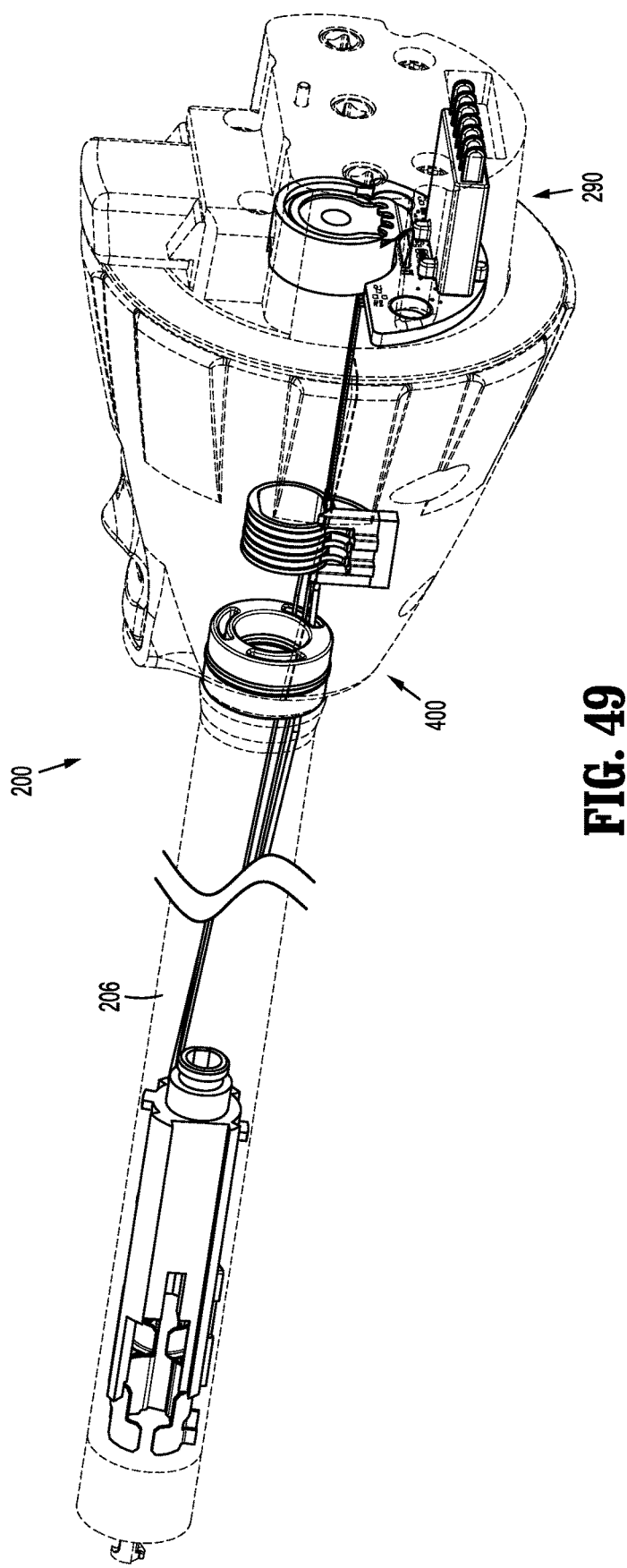
FIG. 49 is a perspective view of an adapter assembly in accordance with the present disclosure with several features shown in phantom.

As illustrated in FIG. 1A, surgical device 100 is configured for selective connection with an adapter assembly 200, and, in turn, adapter assembly 200 is configured for selective connection with a loading unit 300 (e.g., an end effector, or multiple- or single-use loading unit; see FIG. 48). Surgical device 100 and adapter assembly 200, together, may comprise an electromechanical surgical system that is configured and adapted to selectively connect with a loading unit 300 and to actuate loading unit 300.

Figure 1B:
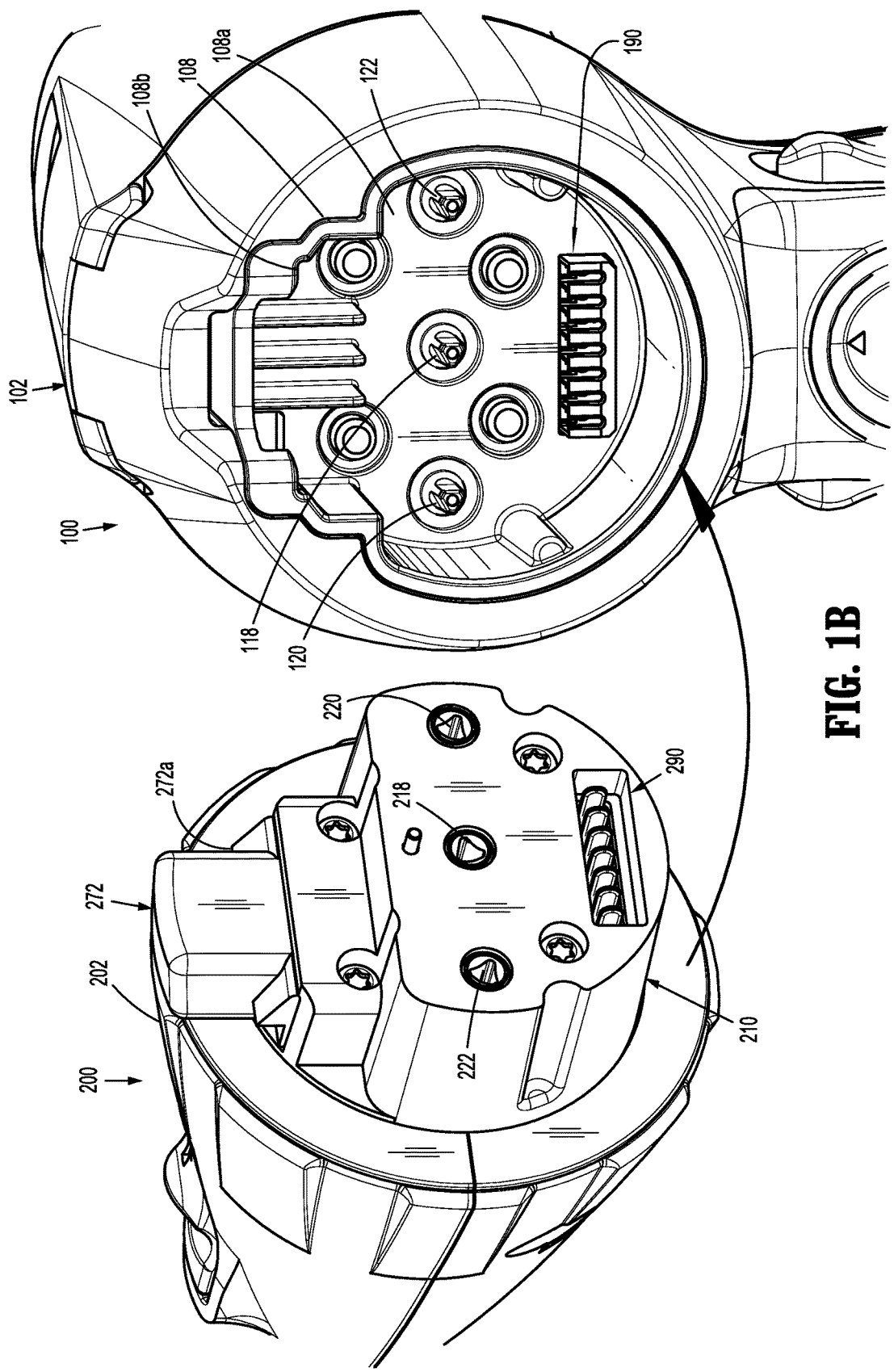
FIG. 1B is a perspective view illustrating an attachment of a proximal end of the adapter assembly to a distal end of the electromechanical surgical device.

As illustrated in FIGS. 1A and 1B, surgical device 100 includes a handle housing 102 including a circuit board (not shown), and a drive mechanism (not shown) is situated therein. The circuit board is configured to control the various operations of surgical device 100. Handle housing 102 defines a cavity therein (not shown) for selective removable receipt of a rechargeable battery (not shown) therein. The battery is configured to supply power to any of the electrical components of surgical device 100.

Handle housing 102 includes an upper housing portion 102a which houses various components of surgical device 100, and a lower hand grip portion 102b extending from upper housing portion 102a. Lower hand grip portion 102b may be disposed distally of a proximal-most end of upper housing portion 102a. The location of lower housing portion 102b relative to upper housing portion 102a is selected to balance a weight of a surgical device 100 that it is connected to or supporting adapter assembly 200 and/or end effector 300.

Handle housing 102 provides a housing in which the drive mechanism is situated. The drive mechanism is configured to drive shafts and/or gear components in order to perform the various operations of surgical device 100. In particular, the drive mechanism is configured to drive shafts and/or gear components in order to selectively move a tool assembly 304 of loading unit 300 (see FIGS. 1A and 48) relative to a proximal body portion 302 of loading unit 300, to rotate loading unit 300 about a longitudinal axis "X" (see FIG. 1A) relative to handle housing 102, to move/approximate an anvil assembly 306 and/or a cartridge assembly 308 of loading unit 300 relative to one another, and/or to fire a stapling and cutting cartridge within cartridge assembly 308 of loading unit 300.

Figure 5:
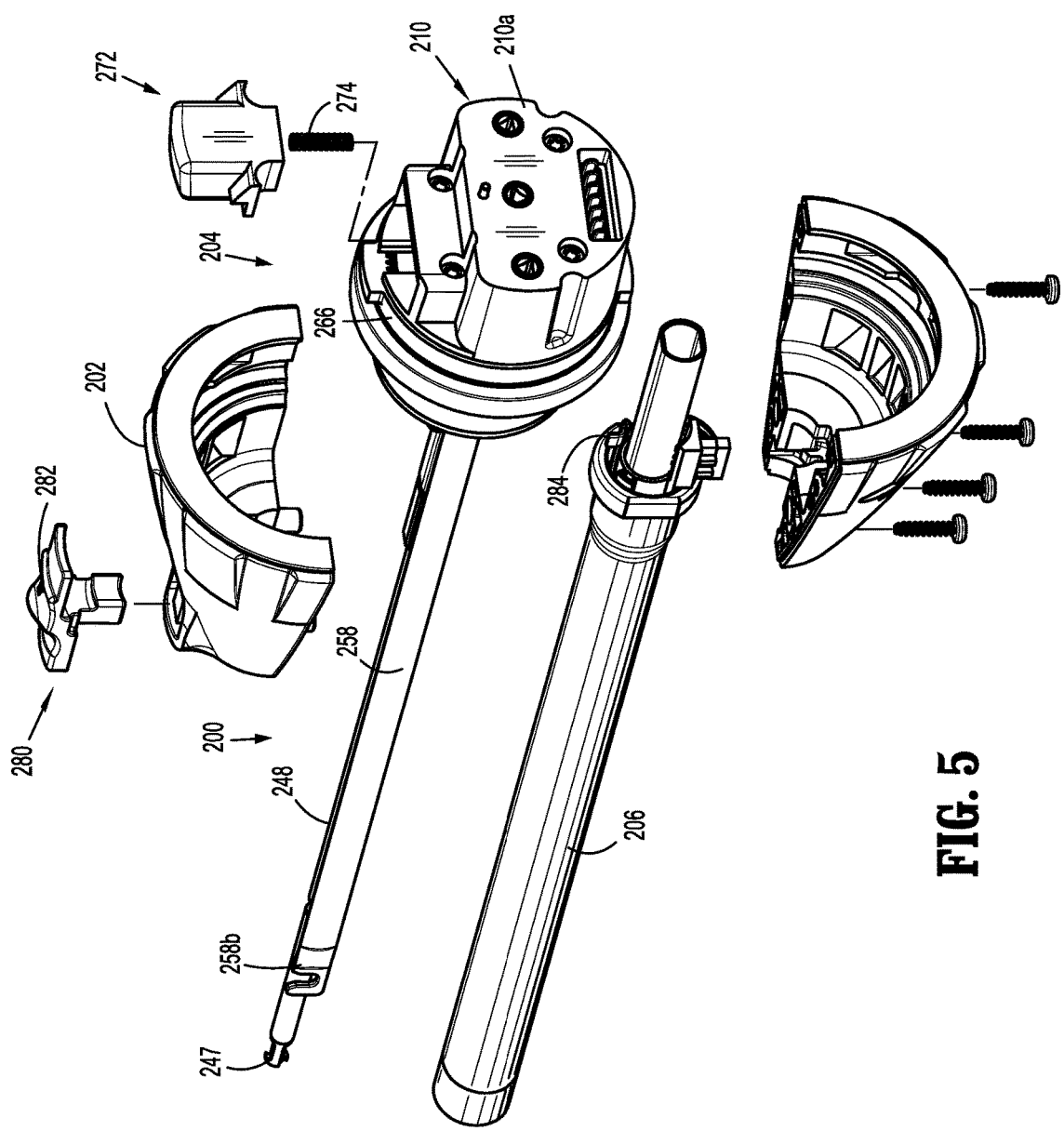
FIG. 5 is a rear, perspective view of the adapter assembly of FIGS. 2A and 2B, with some parts thereof separated.

As illustrated in FIG. 1B, handle housing 102 defines a connecting portion 108 configured to accept a corresponding drive coupling assembly 210 of adapter assembly 200. Specifically, connecting portion 108 of surgical device 100 has a recess 108a that receives a proximal cap 210a (FIGS. 5 and 6) of drive coupling assembly 210 of adapter assembly 200 when adapter assembly 200 is mated to surgical device 100. Connecting portion 108 houses three rotatable drive connectors 118, 120, 122 which are arranged in a common plane or line with one another.

When adapter assembly 200 is mated to surgical device 100, each of rotatable drive connectors 118, 120, 122 of surgical device 100 couples with a corresponding rotatable connector sleeve 218, 220, 222 of adapter assembly 200 (see FIG. 1B). In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical device 100 causes a corresponding rotation of the corresponding connector sleeve 218, 220, 222 of adapter assembly 200.

The mating of drive connectors 118, 120, 122 of surgical device 100 with connector sleeves 218, 220, 222 of adapter assembly 200 allows rotational forces to be independently transmitted via each of the three respective connector interfaces. The drive connectors 118, 120, 122 of surgical device 100 are configured to be independently rotated by the drive mechanism of surgical device 100. In this regard, a function selection module (not shown) of the drive mechanism selects which drive connector or connectors 118, 120, 122 of surgical device 100 is to be driven by the motor of surgical device 100.

Since each of drive connectors 118, 120, 122 of surgical device 100 has a keyed and/or substantially non-rotatable interface with respective connector sleeves 218, 220, 222 of adapter assembly 200, when adapter assembly 200 is coupled to surgical device 100, rotational force(s) are selectively transferred from drive connectors of surgical device 100 to adapter assembly 200.

The selective rotation of drive connector(s) 118, 120 and/or 122 of surgical device 100 allows surgical device 100 to selectively actuate different functions of loading unit 300. For example, selective and independent rotation of first drive connector 118 of surgical device 100 corresponds to the selective and independent opening and closing of tool assembly 304 of loading unit 300, and driving of a stapling/cutting component of tool assembly 304 of loading unit 300. As an additional example, the selective and independent rotation of second drive connector 120 of surgical device 100 corresponds to the selective and independent articulation of tool assembly 304 of loading unit 300 transverse to longitudinal axis "X" (see FIG. 1A). Additionally, for instance, the selective and independent rotation of third drive connector 122 of surgical device 100 corresponds to the selective and independent rotation of loading unit 300 about longitudinal axis "X" (see FIG. 1A) relative to handle housing 102 of surgical device 100.

As illustrated in FIG. 1A, handle housing 102 supports a plurality of finger-actuated control buttons, rocker devices and the like for activating various functions of surgical device 100.

Reference may be made to International Application No. PCT/US2008/077249, filed Sep. 22, 2008 (Inter. Pub. No. WO 2009/039506) and U.S. patent application Ser. No. 12/622,827, filed on Nov. 20, 2009, the entire content of each of which being incorporated herein by reference, for a detailed description of various internal components of and operation of exemplary electromechanical, hand-held, powered surgical instrument 100.

With particular reference to FIGS. 1B-2B, adapter assembly 200 includes an outer knob housing 202 and an outer tube 206 extending from a distal end of knob housing 202. Knob housing 202 and outer tube 206 are configured and dimensioned to house the components of adapter assembly 200. Outer tube 206 is dimensioned for endoscopic insertion, in particular, outer tube 206 is passable through a typical trocar port, cannula or the like. Knob housing 202 is dimensioned to not enter the trocar port, cannula of the like. Knob housing 202 is configured and adapted to connect to connecting portion 108 of handle housing 102 of surgical device 100.

Adapter assembly 200 is configured to convert a rotation of either of drive connectors 118, 120 and 122 of surgical device 100 into axial translation useful for operating a drive assembly 360 and an articulation link 366 of loading unit 300, as illustrated in FIG. 48 and as will be described in greater detail below. As illustrated in FIGS. 5, 6, 13, 14, 17, 18, 20, 25-34 and 37-40, adapter assembly 200 includes a proximal inner housing assembly 204 rotatably supporting a first rotatable proximal drive shaft 212, a second rotatable proximal drive shaft 214, and a third rotatable proximal drive shaft 216 therein. Each proximal drive shaft 212, 214, 216 functions as a rotation receiving member to receive rotational forces from respective drive shafts of surgical device 100, as described in greater detail below.

As described briefly above, inner housing assembly 210 of shaft assembly 200 is also configured to rotatably support first, second and third connector sleeves 218, 220 and 222, respectively, arranged in a common plane or line with one another. Each of connector sleeves 218, 220, 222 is configured to mate with respective first, second and third drive connectors 118, 120, 122 of surgical device 100, as described above. Each of connector sleeves 218, 220, 222 is further configured to mate with a proximal end of respective first, second and third proximal drive shafts 212, 214, 216.

Inner housing assembly 210 also includes, as illustrated in FIGS. 6, 17, 27 and 28, a first, a second and a third biasing member 224, 226 and 228 disposed distally of respective first, second and third connector sleeves 218, 220, 222. Each of biasing members 224, 226 and 228 is disposed about respective first, second and third rotatable proximal drive shaft 212, 214 and 216. Biasing members 224, 226 and 228 act on respective connector sleeves 218, 220 and 222 to help maintain connector sleeves 218, 220 and 222 engaged with the distal end of respective drive rotatable drive connectors 118, 120, 122 of surgical device 100 when adapter assembly 200 is connected to surgical device 100.

In particular, first, second and third biasing members 224, 226 and 228 function to bias respective connector sleeves 218, 220 and 222 in a proximal direction. In this manner, during assembly of adapter assembly 200 to surgical device 100, if first, second and or third connector sleeves 218, 220 and/or 222 is/are misaligned with the drive connectors 118, 120, 122 of surgical device 100, first, second and/or third biasing member(s) 224, 226 and/or 228 are compressed. Thus, when surgical device 100 is operated, drive connectors 118, 120, 122 of surgical device 100 will rotate and first, second and/or third biasing member(s) 224, 226 and/or 228 will cause respective first, second and/or third connector sleeve(s) 218, 220 and/or 222 to slide back proximally, effectively coupling drive connectors 118, 120, 122 of surgical device 100 to first, second and/or third proximal drive shaft(s) 212, 214 and 216 of inner housing assembly 210.

Adapter assembly 200 includes a plurality of force/rotation transmitting/converting assemblies, each disposed within inner housing assembly 204 and outer tube 206. Each force/rotation transmitting/converting assembly is configured and adapted to transmit/convert a speed/force of rotation (e.g., increase or decrease) of first, second and third rotatable drive connectors 118, 120 and 122 of surgical instrument 100 before transmission of such rotational speed/force to loading unit 300.

Figure 6:
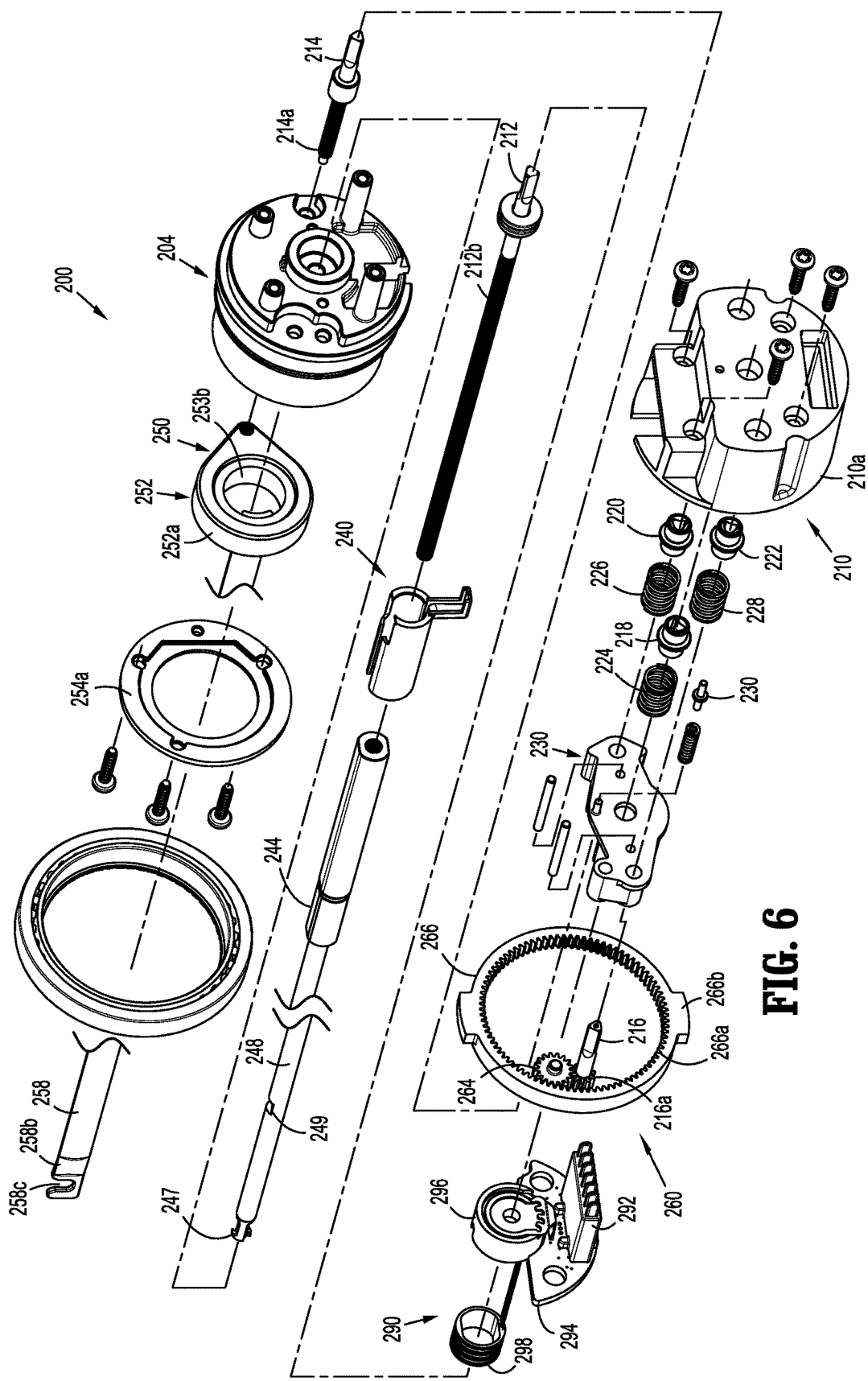
FIG. 6 is a rear, perspective view of the adapter assembly of FIGS. 2A and 2B, with most parts thereof separated.
Figure 7:
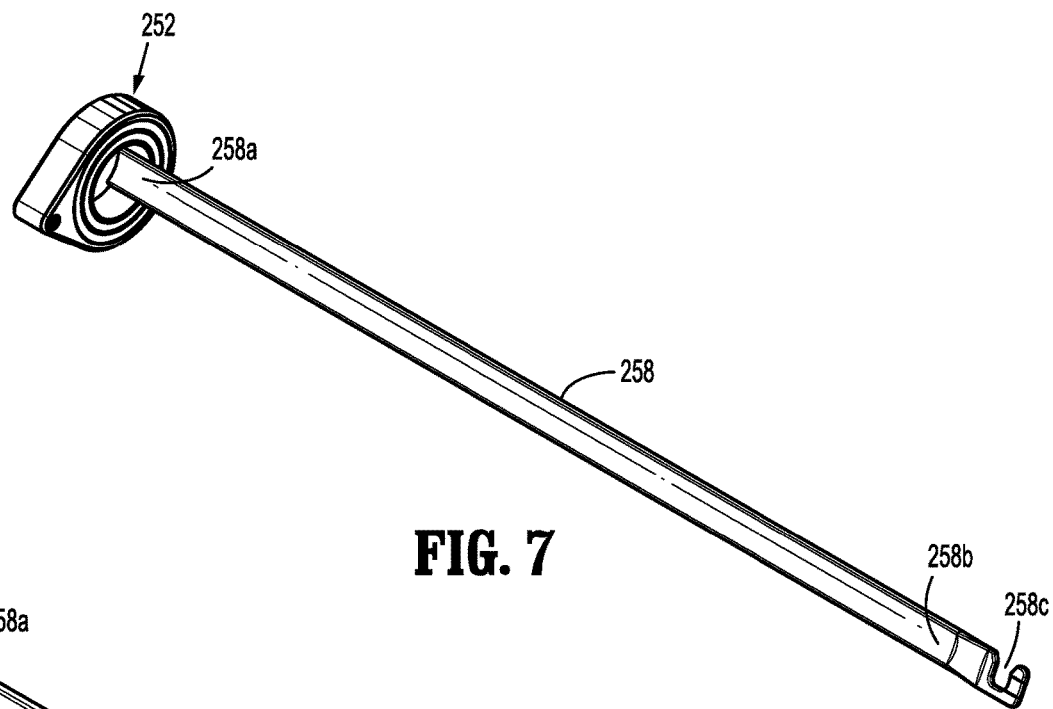
FIG. 7 is a perspective view of an articulation assembly of the adapter assembly of FIGS. 2A and 2B.
Figure 8:
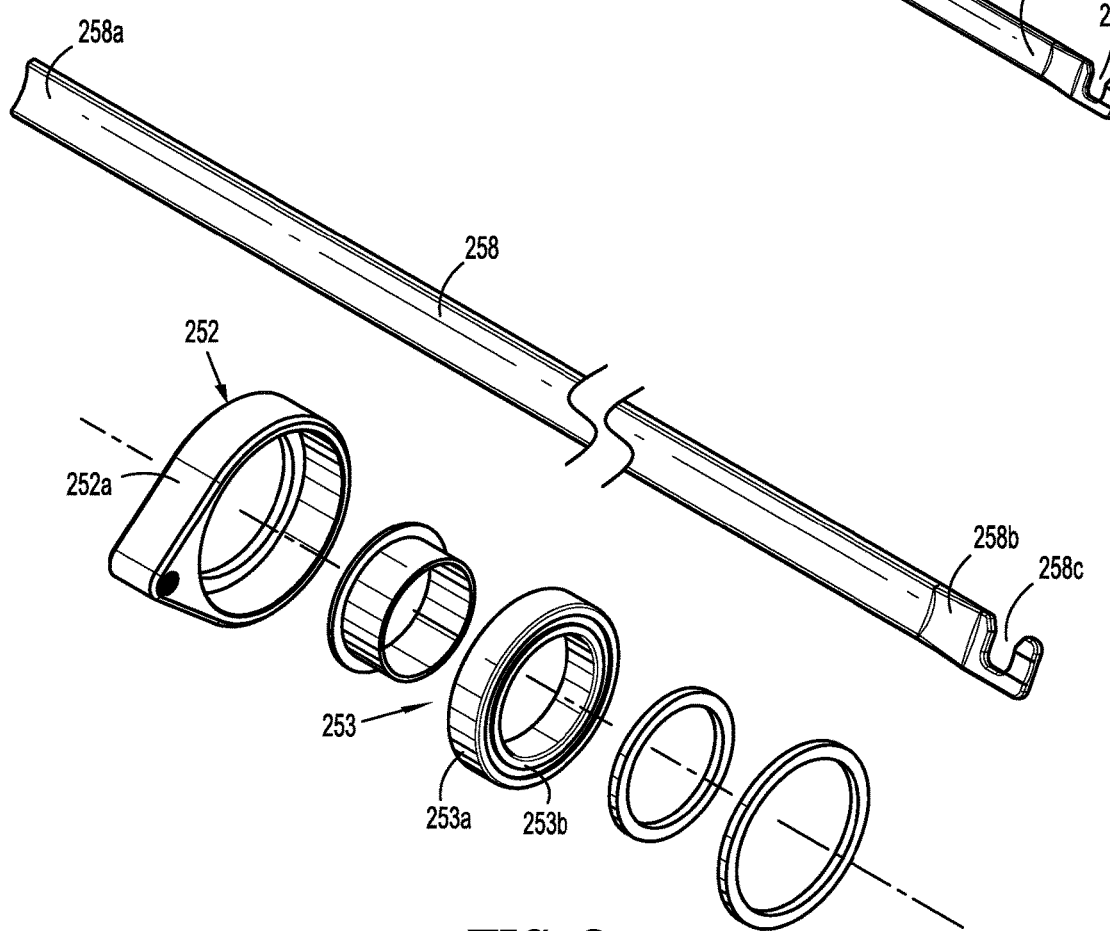
FIG. 8 is an enlarged, perspective view, with parts separated, of the articulation assembly of FIG. 7.
Figure 9:
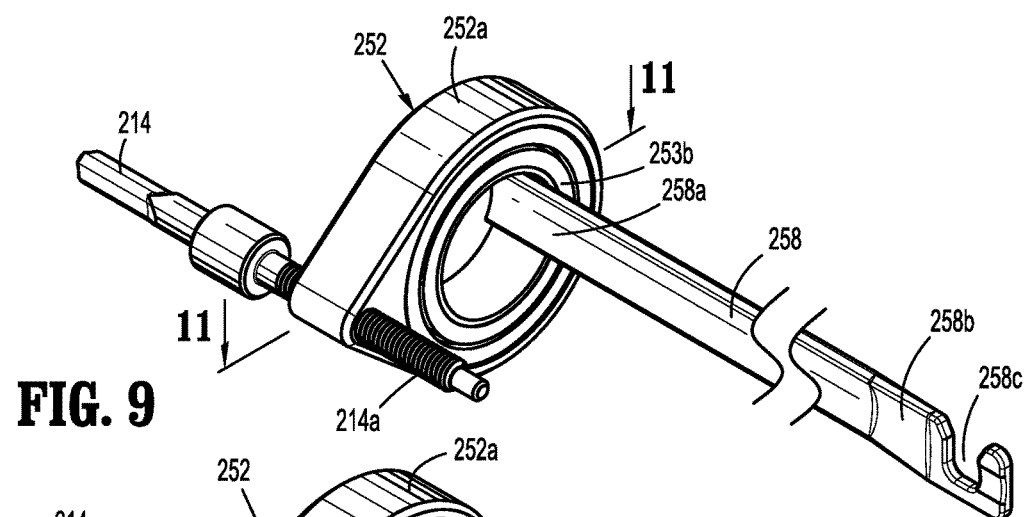
FIG. 9 is a perspective view of the articulation assembly of FIG. 7, shown in a first orientation.
Figure 10:
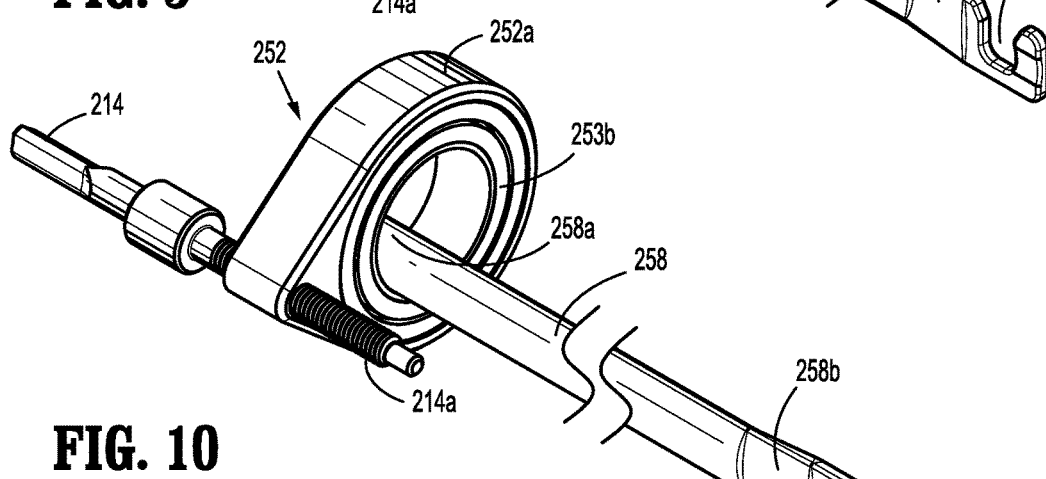
FIG. 10 is a perspective view of the articulation assembly of FIG. 7, shown in a second orientation.
Figure 11:
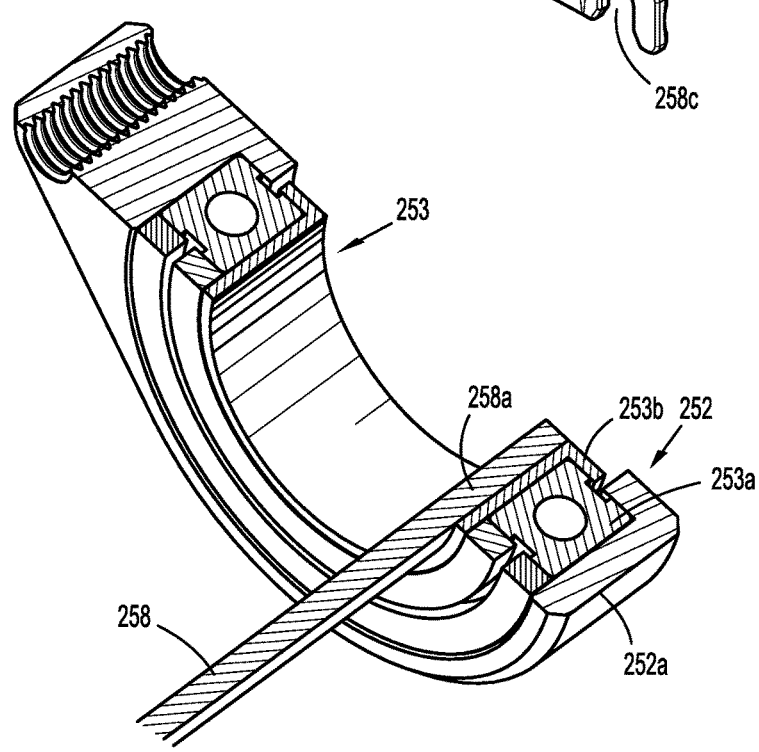
FIG. 11 is a cross-sectional view as taken along section line 11-11 of FIG. 9.
Figure 12A:
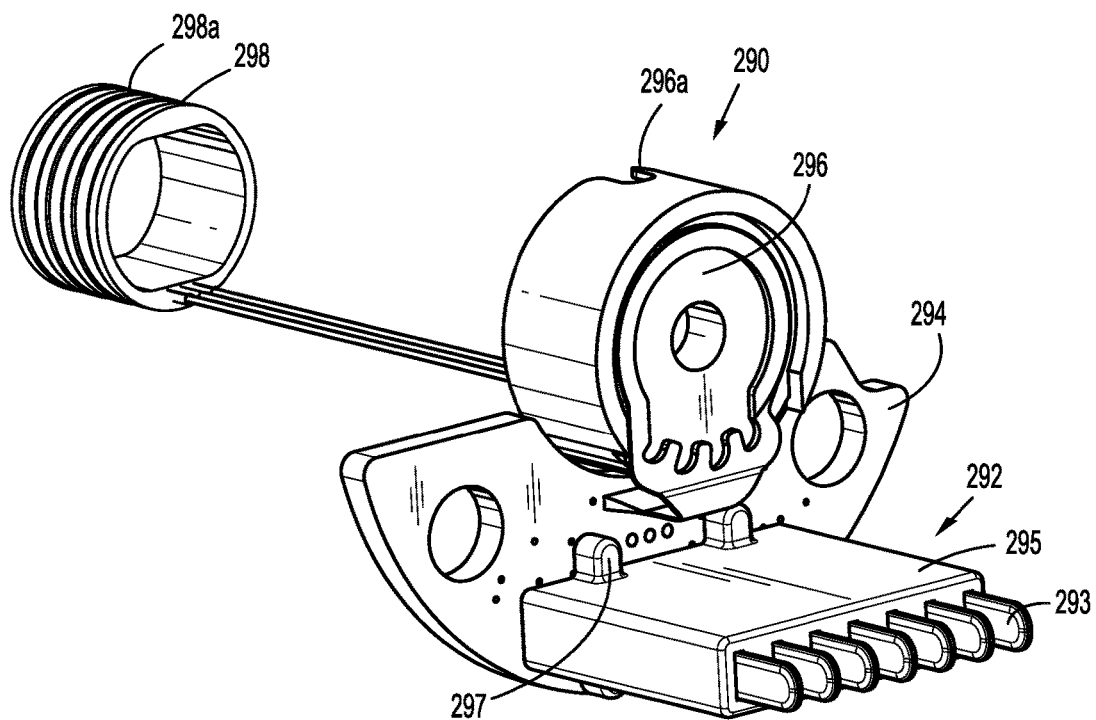
FIG. 12A is a perspective view of an electrical assembly of the adapter assembly of FIGS. 2A and 2B.
Figure 12B:
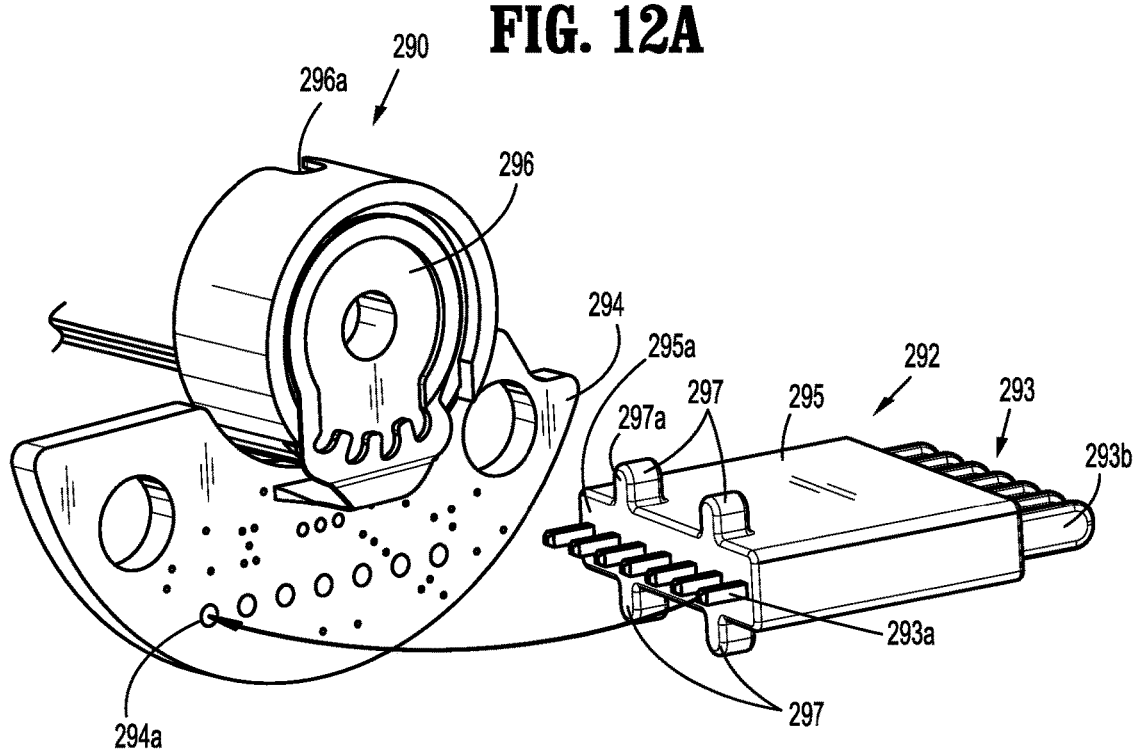
FIG. 12B is a perspective view of the electrical assembly of FIG. 12A showing a connector housing separated from a circuit board.
Figure 12C:
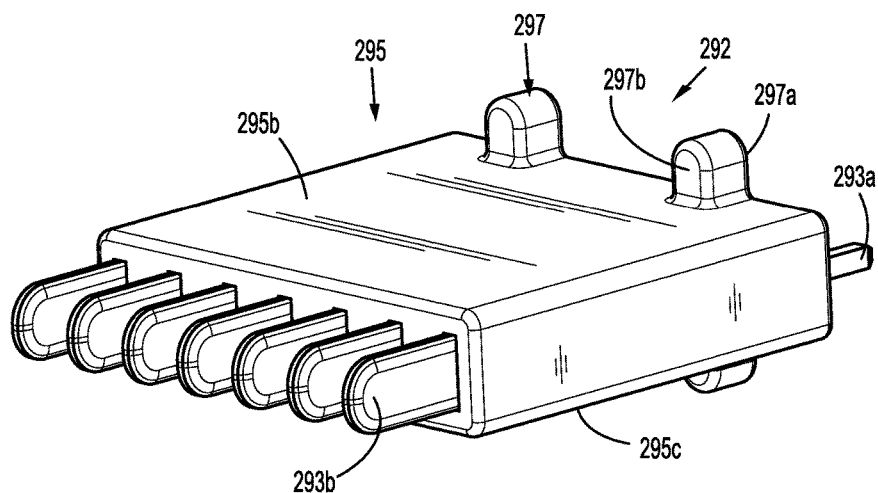
FIG. 12C is a perspective view of the connector housing of FIG. 12B.
Figure 12D:
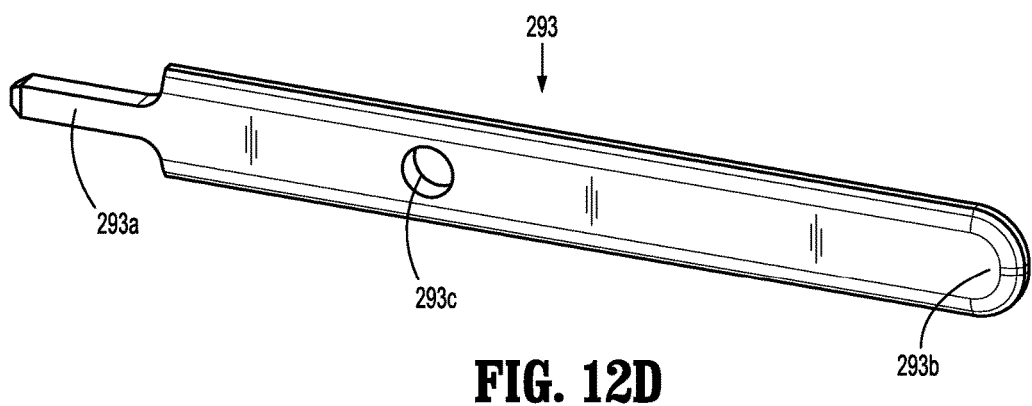
FIG. 12D is a perspective view of an electrical contact pin of the connector housing of FIGS. 12B-12C.
Figure 13:
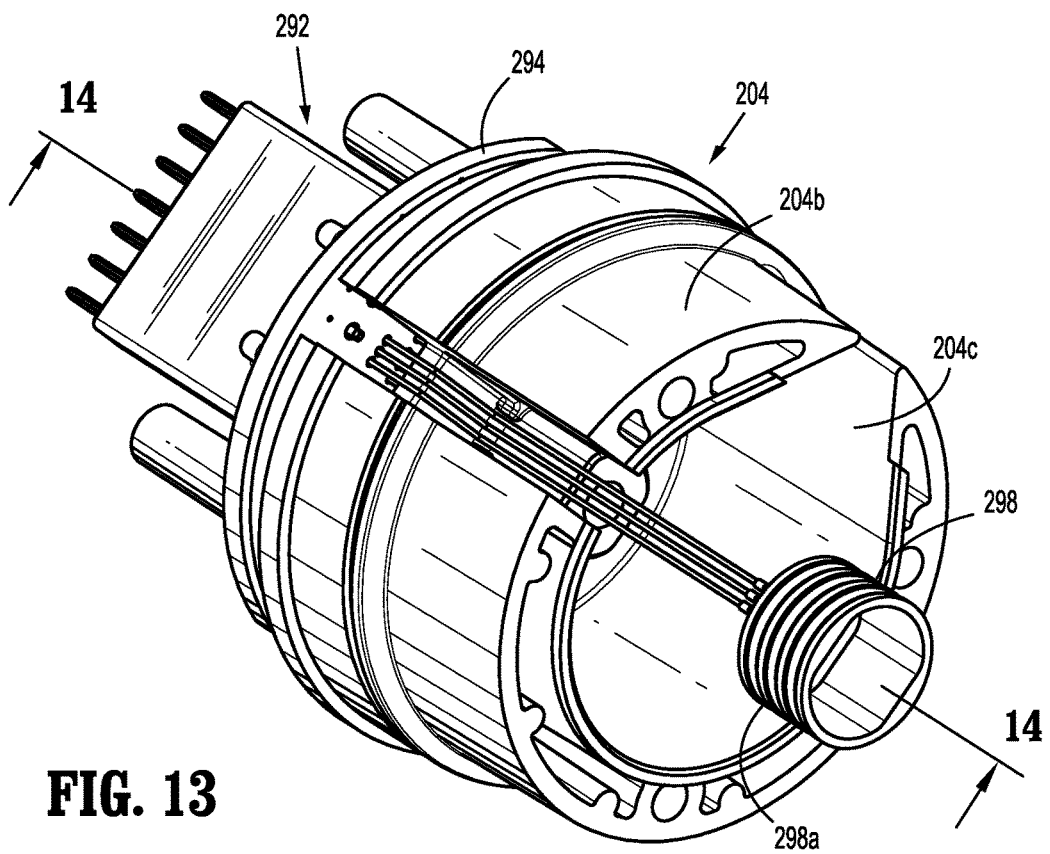
FIG. 13 is a perspective view of the electrical assembly of FIG. 12 shown connected to the core housing of the adapter assembly of FIGS. 2A and 2B.
Figure 14:
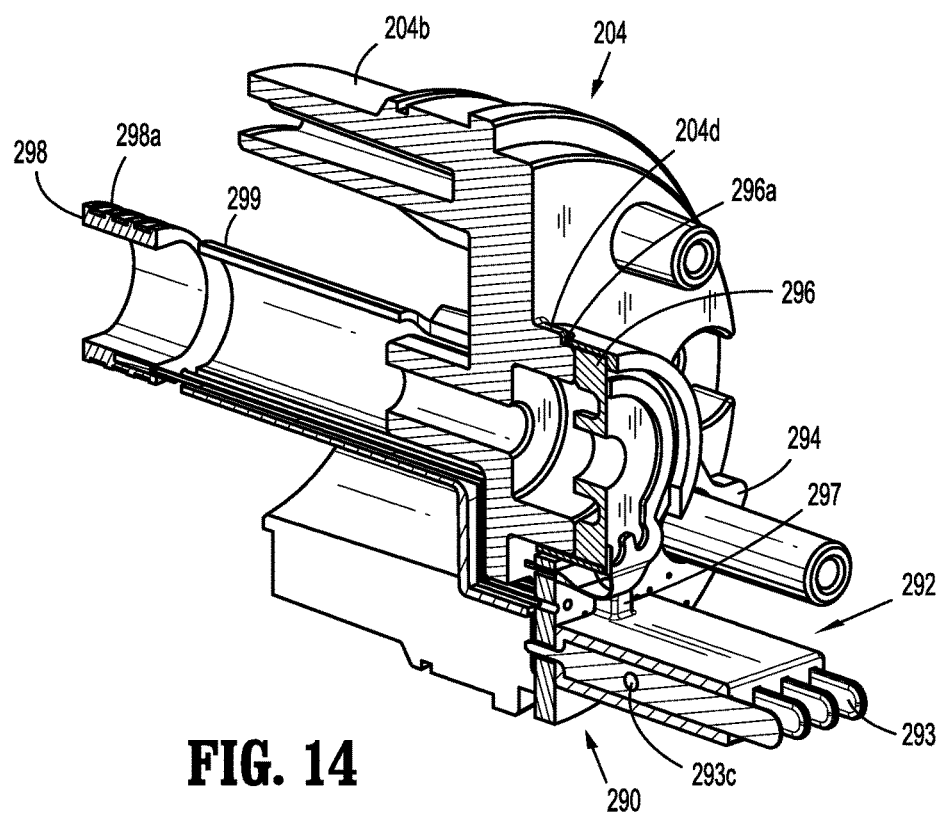
FIG. 14 is a cross-sectional view as taken along section line 14-14 of FIG. 13.

Specifically, as illustrated in FIG. 6, adapter assembly 200 includes a first, a second and a third force/rotation transmitting/converting assembly 240, 250, 260, respectively, disposed within inner housing 208 and outer tube 206. Each force/rotation transmitting/converting assembly 240, 250, 260 is configured and adapted to transmit or convert a rotation of a first, second and third drive connector 118, 120, 122 of surgical device 100 into axial translation of articulation bar 258 of adapter assembly 200, to effectuate articulation of loading unit 300; a rotation of a ring gear 266 of adapter assembly 200, to effectuate rotation of adapter assembly 200; or axial translation of a distal drive member 248 of adapter assembly 200 to effectuate closing, opening and firing of loading unit 300.

As shown in FIGS. 5, 6 and 24-31, first force/rotation transmitting/converting assembly 240 includes first rotatable proximal drive shaft 212, which, as described above, is rotatably supported within inner housing assembly 204. First rotatable proximal drive shaft 212 includes a non-circular or shaped proximal end portion configured for connection with first connector 218 which is connected to respective first connector 118 of surgical device 100. First rotatable proximal drive shaft 212 includes a distal end portion 212b having a threaded outer profile or surface.

First force/rotation transmitting/converting assembly 240 further includes a drive coupling nut 244 rotatably coupled to threaded distal end portion 212b of first rotatable proximal drive shaft 212, and which is slidably disposed within outer tube 206. Drive coupling nut 244 is slidably keyed within proximal core tube portion of outer tube 206 so as to be prevented from rotation as first rotatable proximal drive shaft 212 is rotated. In this manner, as first rotatable proximal drive shaft 212 is rotated, drive coupling nut 244 is translated along threaded distal end portion 212b of first rotatable proximal drive shaft 212 and, in turn, through and/or along outer tube 206.

First force/rotation transmitting/converting assembly 240 further includes a distal drive member 248 that is mechanically engaged with drive coupling nut 244, such that axial movement of drive coupling nut 244 results in a corresponding amount of axial movement of distal drive member 248. The distal end portion of distal drive member 248 supports a connection member 247 configured and dimensioned for selective engagement with a drive member 374 of drive assembly 360 of loading unit 300 (FIG. 48). Drive coupling nut 244 and/or distal drive member 248 function as a force transmitting member to components of loading unit 300, as described in greater detail below.

In operation, as first rotatable proximal drive shaft 212 is rotated, due to a rotation of first connector sleeve 218, as a result of the rotation of the first respective drive connector 118 of surgical device 100, drive coupling nut 244 is caused to be translated axially along first distal drive shaft 242. As drive coupling nut 244 is caused to be translated axially along first distal drive shaft 242, distal drive member 248 is caused to be translated axially relative to outer tube 206. As distal drive member 248 is translated axially, with connection member 247 connected thereto and engaged with drive member 374 of drive assembly 360 of loading unit 300 (FIG. 48), distal drive member 248 causes concomitant axial translation of drive member 374 of loading unit 300 to effectuate a closure of tool assembly 304 and a firing of tool assembly 304 of loading unit 300.

With reference to FIGS. 5-11, 19 and 23-31, second drive converter assembly 250 of adapter assembly 200 includes second proximal drive shaft 214 rotatably supported within inner housing assembly 204. Second rotatable proximal drive shaft 214 includes a non-circular or shaped proximal end portion configured for connection with second connector or coupler 220 which is connected to respective second connector 120 of surgical device 100. Second rotatable proximal drive shaft 214 further includes a distal end portion 214b having a threaded outer profile or surface.

Distal end portion 214b of proximal drive shaft 214 is threadably engaged with an articulation bearing housing 252a of an articulation bearing assembly 252. Articulation bearing assembly 252 includes a housing 252a supporting an articulation bearing 253 having an inner race 253b that is independently rotatable relative to an outer race 253a. Articulation bearing housing 252a has a non-circular outer profile, for example tear-dropped shaped, that is slidably and non-rotatably disposed within a complementary bore 204c (FIGS. 25, 26, 29 and 33) of inner housing hub 204a.

Second drive converter assembly 250 of adapter assembly 200 further includes an articulation bar 258 having a proximal portion 258a secured to inner race 253b of articulation bearing 253. A distal portion 258b of articulation bar 258 includes a slot 258c therein, which is configured to accept a portion 366, e.g., a flag, articulation link (FIG. 48) of loading unit 300. Articulation bar 258 functions as a force transmitting member to components of loading unit 300, as described in greater detail below.

With further regard to articulation bearing assembly 252, articulation bearing assembly 252 is both rotatable and longitudinally translatable. Additionally, it is envisioned that articulation bearing assembly 252 allows for free, unimpeded rotational movement of loading unit 300 when its jaw members 306, 308 are in an approximated position and/or when jaw members 306, 308 are articulated (FIG. 48).

In operation, as second proximal drive shaft 214 is rotated due to a rotation of second connector sleeve 220, as a result of the rotation of the second drive connector 120 of surgical device 100, articulation bearing assembly 252 is caused to be translated axially along threaded distal end portion 214b of second proximal drive shaft 214, which in turn causes articulation bar 258 to be axially translated relative to outer tube 206. As articulation bar 258 is translated axially, articulation bar 258, being coupled to articulation link 366 of loading unit 300, causes concomitant axial translation of articulation link 366 of loading unit 300 to effectuate an articulation of tool assembly 304 (FIG. 48). Articulation bar 258 is secured to inner race 253b of articulation bearing 253 and is thus free to rotate about the longitudinal axis X-X relative to outer race 253a of articulation bearing 253.

As illustrated in FIGS. 6, 17, 18, 20-23, 25-28, 31 and 37-40 and as mentioned above, adapter assembly 200 includes a third force/rotation transmitting/converting assembly 260 supported in inner housing assembly 204. Third force/rotation transmitting/converting assembly 260 includes a rotation ring gear 266 fixedly supported in and connected to outer knob housing 202. Ring gear 266 defines an internal array of gear teeth 266a (FIG. 6). Ring gear 266 includes a pair of diametrically opposed, radially extending protrusions 266b (FIG. 6) projecting from an outer edge thereof. Protrusions 266b are disposed within recesses defined in outer knob housing 202, such that rotation of ring gear 266 results in rotation of outer knob housing 202, and vice a versa.

Third force/rotation transmitting/converting assembly 260 further includes third rotatable proximal drive shaft 216 which, as described above, is rotatably supported within inner housing assembly 204. Third rotatable proximal drive shaft 216 includes a non-circular or shaped proximal end portion configured for connection with third connector 222 which is connected to respective third connector 122 of surgical device 100. Third rotatable proximal drive shaft 216 includes a spur gear 216a keyed to a distal end thereof. A reversing spur gear 264 inter-engages spur gear 216a of third rotatable proximal drive shaft 216 to gear teeth 266a of ring gear 266.

In operation, as third rotatable proximal drive shaft 216 is rotated, due to a rotation of third connector sleeve 222, as a result of the rotation of the third drive connector 122 of surgical device 100, spur gear 216a of third rotatable proximal drive shaft 216 engages reversing gear 264 causing reversing gear 264 to rotate. As reversing gear 264 rotates, ring gear 266 also rotates thereby causing outer knob housing 202 to rotate. As outer knob housing 202 is rotated, outer tube 206 is caused to be rotated about longitudinal axis "X" of adapter assembly 200. As outer tube 206 is rotated, loading unit 300, that is connected to a distal end portion of adapter assembly 200, is also caused to be rotated about a longitudinal axis of adapter assembly 200.

Adapter assembly 200 further includes, as seen in FIGS. 1B, 3-5, 16, 17, 20 and 24-26, an attachment/detachment button 272 supported thereon. Specifically, button 272 is supported on drive coupling assembly 210 of adapter assembly 200 and is biased by a biasing member 274 to an un-actuated condition. Button 272 includes lip or ledge 272a formed therewith that is configured to snap behind a corresponding lip or ledge 108b defined along recess 108a of connecting portion 108 of surgical device 100. In use, when adapter assembly 200 is connected to surgical device 100, lip 272a of button 272 is disposed behind lip 108b of connecting portion 108 of surgical device 100 to secure and retain adapter assembly 200 and surgical device 100 with one another. In order to permit disconnection of adapter assembly 200 and surgical device 100 from one another, button 272 is depresses or actuated, against the bias of biasing member 274, to disengage lip 272a of button 272 and lip 108b of connecting portion 108 of surgical device 100.

With reference to FIGS. 1A, 2A, 2B, 3-5 and 24-26, adapter assembly 200 further includes a lock mechanism 280 for fixing the axial position and radial orientation of distal drive member 248. Lock mechanism 280 includes a button 282 slidably supported on outer knob housing 202. Lock button 282 is connected to an actuation bar 284 that extends longitudinally through outer tube 206. Actuation bar 284 moves upon a movement of lock button 282. Upon a predetermined amount of movement of lock button 282, a distal end of actuation bar 284 may move into contact with a lock out (not shown), which causes the lock out to cam a camming member 288 (FIG. 24) from a recess 249 in distal drive member 248. When camming member 288 is in engagement with recess 249 (e.g., at least partially within recess 249, see FIGS. 6 and 24), the engagement between camming member 288 and distal drive member 248 effectively locks the axial and rotational position of end effector 300 that is engaged with connection member 247.

In operation, in order to lock the position and/or orientation of distal drive member 248, a user moves lock button 282 from a distal position to a proximal position (FIGS. 25 and 26), thereby causing the lock out (not shown) to move proximally such that a distal face of the lock out moves out of contact with camming member 288, which causes camming member 288 to cam into recess 249 of distal drive member 248. In this manner, distal drive member 248 is prevented from distal and/or proximal movement. When lock button 282 is moved from the proximal position to the distal position, the distal end of actuation bar 284 moves distally into the lock out, against the bias of a biasing member (not shown), to force camming member 288 out of recess 249, thereby allowing unimpeded axial translation and radial movement of distal drive member 248.

Reference may be made to U.S. patent application Ser. No. 13/875,571, filed on May 2, 2013, the entire content of which is incorporated herein by reference, for a more detailed discussion of the construction and operation of lock mechanism 280.

With reference to FIGS. 1B, 6, 12A-15 and 25-28, adapter assembly 200 includes a proximal electrical assembly 290 supported on and in outer knob housing 202 and inner housing assembly 204. Proximal electrical assembly 290 includes an electrical connector 292 supported on a circuit board 294, for electrical connection to a corresponding electrical plug 190 disposed in connecting portion 108 of surgical device 100.

With particular reference to FIGS. 12A-12D, electrical connector 292 includes a plurality of electrical contact pins 293 and a housing or connector housing 295. Electrical contact pins 293 serve to allow for calibration and communication of life-cycle information to the circuit board of surgical device 100 via electrical plugs 190 that are electrically connected to the circuit board (not shown) of surgical device 100.

Each electrical contact pin 293 includes a distal portion 293a and a proximal portion 293b. Distal portion 293a of each contact pin 293 is configured to engage circuit board 294, e.g., via soldering. Proximal portion 293b of each contact pin 293 is configured to releasably engage corresponding electrical plug 190 disposed in connecting portion 108 of surgical device 100. With continued reference to FIGS. 12A-12D, distal portion 293a of each electrical contact pin 293 is tapered to facilitate insertion into holes 294a (FIG. 12B) of circuit board 294. Proximal portion 293b of each electrical contact pin 293 includes a rectangular cross-section, and is tapered and chamfered to facilitate engagement and disengagement with electrical plug 190.

Additionally, each electrical contact pin 293 includes a hole 293c extending laterally therethrough. Hole 293c is configured to facilitate the connection between electrical contact pins 293 and housing 295. It is envisioned that housing 295 is over-molded, such that portions of the over-mold extend through holes 293c in electrical contact pins 293. As can be appreciated, the engagement between electrical contact pins 293 and housing 295 helps maintain proper alignment of pins 293 to further facilitate engagement between electrical connector 292 and circuit board 294 and electrical plug 190, and to further facilitate engagement between electrical connector 292 and electrical plug 190. While seven electrical contact pins 293 are shown, it is envisioned that more or fewer electrical contact pins 293 are included with proximal electrical assembly 290.

With continued reference to FIGS. 12A-12D, housing 295 of electrical connector 292 includes a rectangular cross-section. The rectangular cross-section of housing 295 is configured to mate with a rectangular opening of proximal cap 210a (FIGS. 5 and 6) of drive coupling assembly 210 to prevent radial movement therebetween.

Housing 295 also includes a plurality of projections 297 extending therefrom. Projections 297 each include a distal face 297a and a proximal face 297b. Distal face 297a of each projection 297 is configured and positioned to contact circuit board 294 during insertion of electrical connector 292. Thus, distal face 297a of each projection 297 prevents electrical contact pins 293 of electrical connector 292 from being inserted too far distally into holes 294a of circuit board 294. While distal face 297a of each projection 297 is illustrated as being flush with a distal face 295a of housing 295 (FIG. 12D), it is envisioned that distal face 297a of each projection 297 is positioned farther proximally or distally than distal face 295a of housing 295. Proximal face 297b of each projection 297 is configured and positioned to prevent disengagement between electrical connector 292 and circuit board 294, e.g., during disengagement between surgical device 100 and adapter assembly 200. More particularly, the proximal cap 210 of proximal electrical assembly 290 is configured to abut proximal face 297b of at least one or all projections 297, thus preventing proximal movement of electrical connector 292 with respect to circuit board 294. In the illustrated embodiment, two projections 297 extend from a first surface 295b of housing 295, and two projections 297 extend from a second surface 295c of housing 295. However, housing 295 may include more or fewer projections 297.

Proximal electrical assembly 290 further includes a strain gauge 296 electrically connected to circuit board 294. Strain gauge 296 is provided with a notch 296a which is configured and adapted to receive stem 204d of hub 204a of inner housing assembly 204. Stem 204d of hub 204a functions to restrict rotational movement of strain gauge 296. As illustrated in FIGS. 25-28, first rotatable proximal drive shaft 212 extends through strain gauge 296. Strain gauge 296 provides a closed-loop feedback to a firing/clamping load exhibited by first rotatable proximal drive shaft 212.

Proximal electrical assembly 290 also includes a slip ring 298 disposed within outer tube 206. Slip ring 298 is in electrical connection with circuit board 294 via a plurality of proximal wires 299. Slip ring 298 functions to permit rotation of first rotatable proximal drive shaft 212 and axial translation of drive coupling nut 244 while still maintaining electrical contact between electrical contact rings 298a thereof and a distal electrical assembly 400 (see FIGS. 49-55) within adapter assembly 200, and while permitting the other electrical components to rotate about first rotatable proximal drive shaft 212 and drive coupling nut 244

Turning now to FIGS. 6, 11, 14, 32 and 33, inner housing assembly 204 has been designed to reduce incidents of racking of second proximal drive shaft 214 as drive shaft 214 rotates to axially translate articulation bearing assembly 252. Inner housing assembly 204 includes a hub 204a having a distally oriented annular wall 204b defining a substantially circular outer profile, and defining a substantially tear-drop shaped inner recess or bore 204c. Bore 204c of hub 204a is shaped and dimensioned to slidably receive articulation bearing assembly 252 therewithin.

Inner housing assembly 204 includes a ring plate 254a (FIG. 34) secured to a distal face of distally oriented annular wall 204b of hub 204a. Plate 254a defines an aperture 254e therethrough that is sized and formed therein so as to be aligned with second proximal drive shaft 214 and to rotatably receive a distal tip 214c of second proximal drive shaft 214. In this manner, distal tip 214c of second proximal drive shaft 214 is supported and prevented from moving radially away from a longitudinal rotational axis of second proximal drive shaft 214 as second proximal drive shaft 214 is rotated to axially translate articulation bearing assembly 252.

As illustrated in FIGS. 14, 32, 39 and 40, hub 204a defines a feature (e.g., a stem or the like) 204d projecting therefrom which functions to engage notch 296a of strain gauge 296 of proximal electrical assembly 290 to measure forces experienced by shaft 212 as surgical device 100 is operated.

With reference to FIGS. 35-40, a plate bushing 230 of inner housing assembly 204 is shown and described. Plate bushing 230 extends across hub 204a of inner housing assembly 204 and is secured to hub 204a by fastening members. Plate bushing 230 defines three apertures 230a, 230b, 230c that are aligned with and rotatably receive respective first, second and third proximal drive shafts 212, 214, 216 therein. Plate bushing 230 provides a surface against which first, second and third biasing members 224, 226 and 228 come into contact or rest against.

Figure 40:
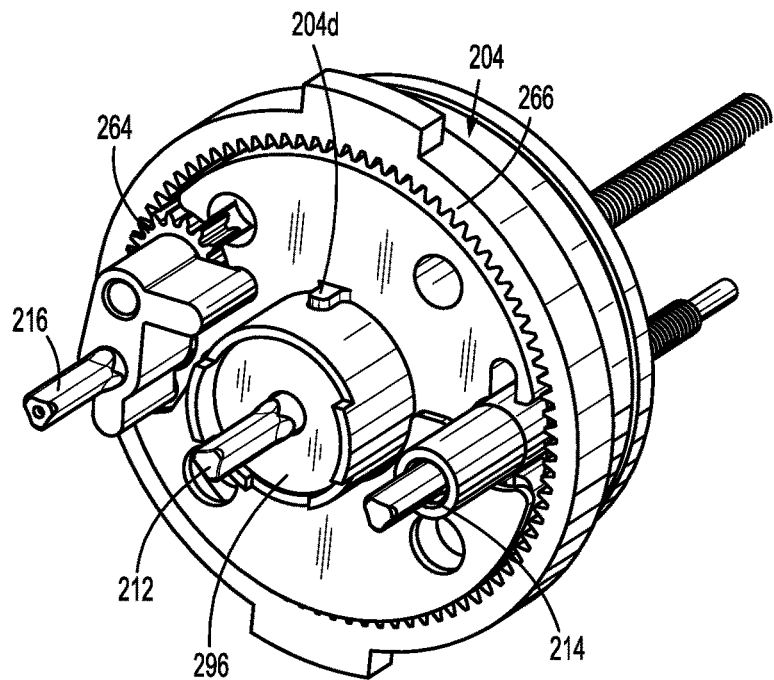
FIG. 40 is a rear, perspective view of the proximal inner housing assembly of FIG. 37 with connector sleeves removed therefrom.
Figure 41:
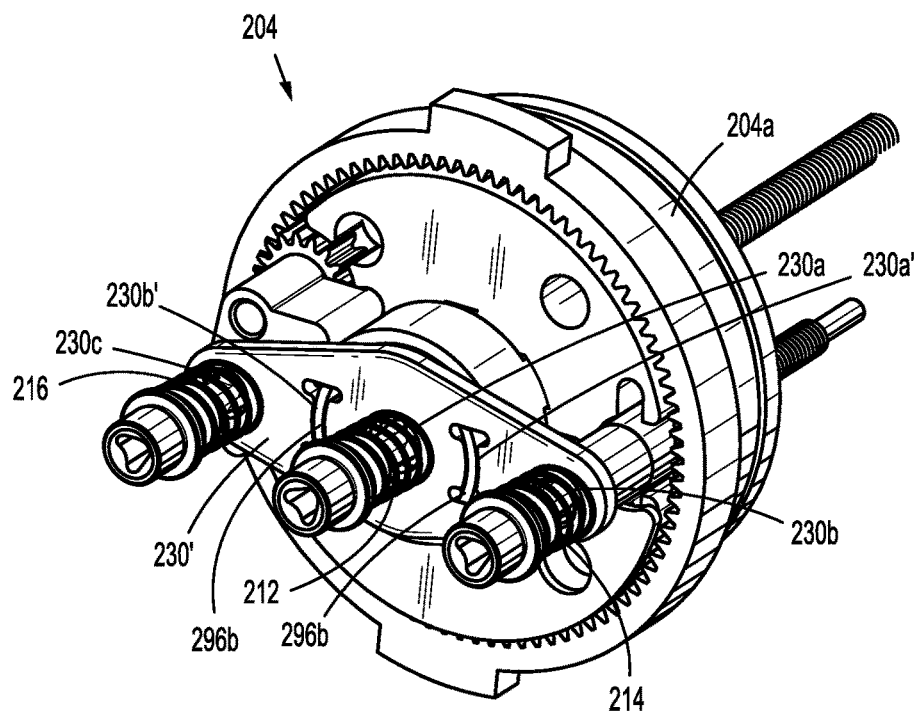
FIG. 41 is a rear, perspective of the inner housing assembly of FIG. 37 illustrating a support plate, according to another embodiment of the present disclosure, coupled thereto.
Figure 42:
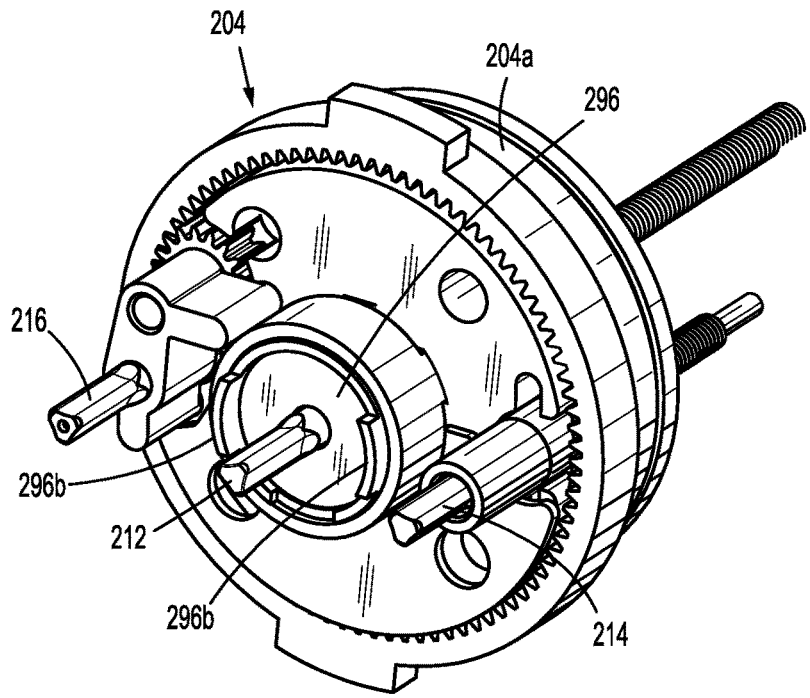
FIG. 42 is a rear, perspective of the inner housing assembly of FIG. 41 with the support plate removed therefrom.
Figure 43:
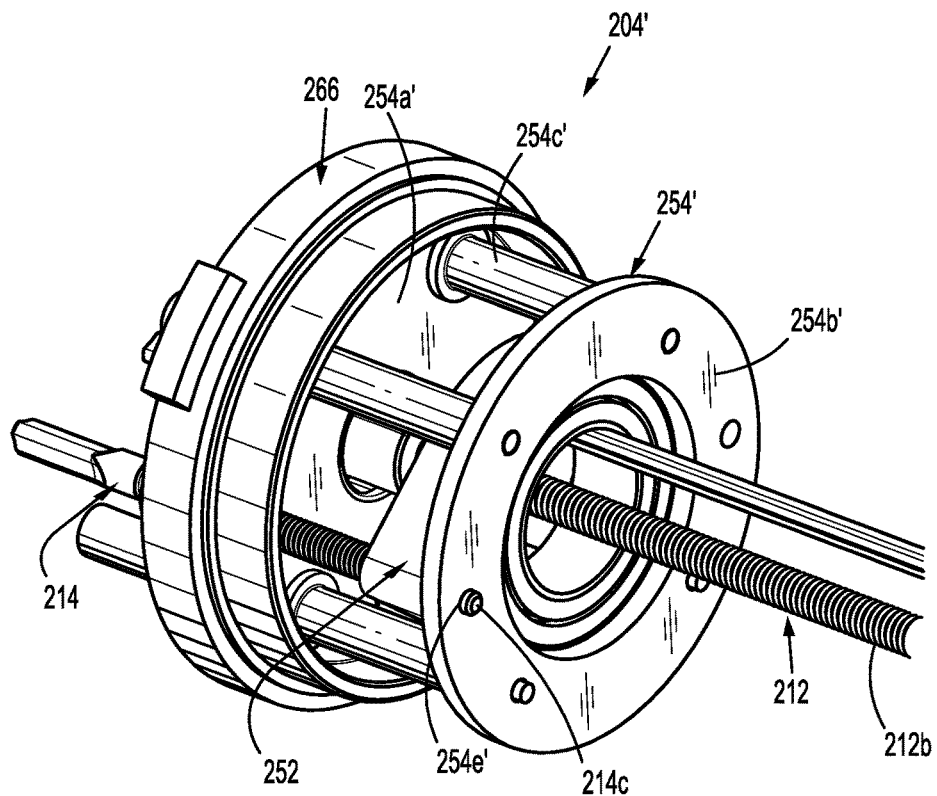
FIG. 43 is a front, perspective view of an inner housing assembly according to another embodiment of the present disclosure with the outer knob housing, the proximal inner housing removed therefrom.
Figure 44:
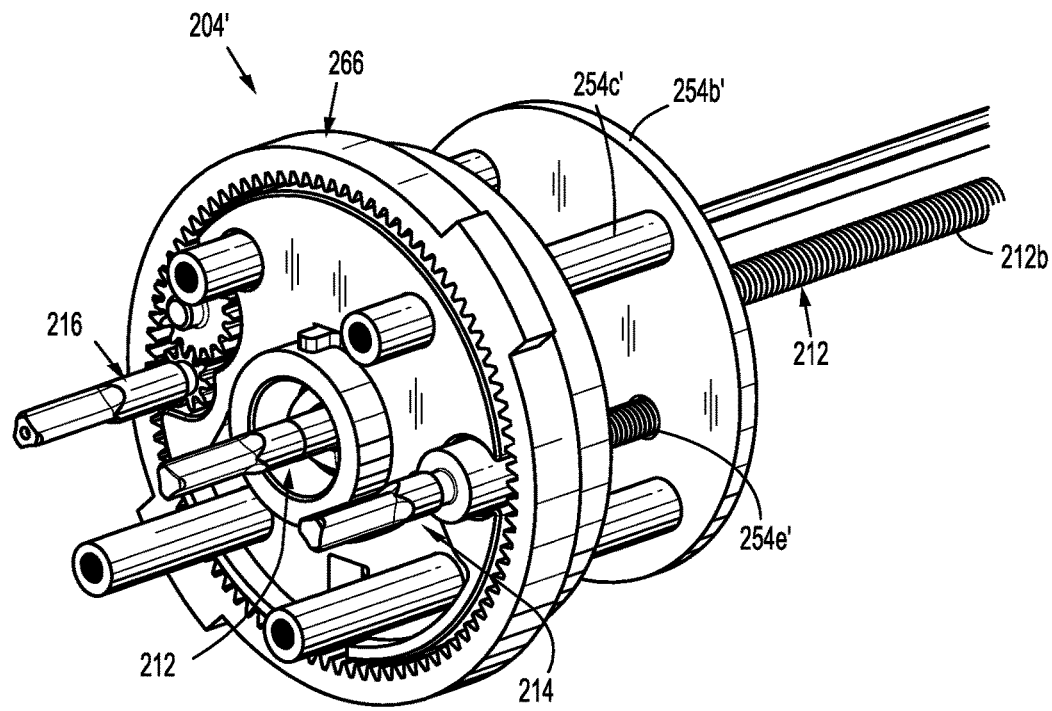
FIG. 44 is a rear, perspective view of the inner housing assembly of FIG. 43 with the outer knob housing, the proximal inner housing and the articulation assembly removed therefrom.

While plate bushing 230 has been shown and described as being a unitary monolithic piece, as illustrated in FIGS. 6 and 37-40, it is envisioned and within the scope of the present application that plate bushing 230 may be separated into several parts including, and not limited to, as seen in FIGS. 40-42, a support plate 230' extending across drive shafts 212, 214, 216, and a separate bushing for each of drive shafts 212, 214, 216 and disposed between the support plate 230' and hub 204a of inner housing assembly 204. Support plate 230' may include a pair of slots 230a', 230b' formed therein, which are configured and adapted to receive tabs 296b of strain gauge 296 that project axially therefrom.

Turning now to FIGS. 43-47, an inner housing assembly 204' according to another embodiment of the present disclosure is shown and will be described. In order to reduce incidents of racking (i.e., distal end 214b of second proximal drive shaft 214 moving radially away from a longitudinal rotational axis thereof) of second proximal drive shaft 214 as drive shaft 214 rotates to axially translate articulation bearing assembly 252, inner housing assembly 204' may include a reinforcement frame or bracket assembly 254'. Bracket assembly 254' includes a first plate 254a' and a second plate 254b' integrally connected to and spaced a distance from first plate 254a' by a plurality of connecting rods 254c' extending therebetween.

First plate 254a' is disposed adjacent to or in close proximity to ring gear 266 and defines an aperture 254d' therethrough. Aperture 254d' is sized and formed in first plate 254a' so as to be aligned with second proximal drive shaft 214 and to permit second proximal drive shaft 214 to freely rotate therewithin. Second plate 254b' is spaced from first plate 254a' so as to be disposed at a distal free end of second proximal drive shaft 214. Second plate 254b' defines an aperture 254e' therethrough. Aperture 254e' is sized and formed in second plate or flange 254b' so as to be aligned with second proximal drive shaft 214 and to rotatably receive a distal tip 214c of second proximal drive shaft 214.

In this manner, distal tip 214c of second proximal drive shaft 214 is supported and prevented from moving radially away from a longitudinal rotational axis of second proximal drive shaft 214 as second proximal drive shaft 214 is rotated to axially translate articulation bearing assembly 252.

Figure 38:
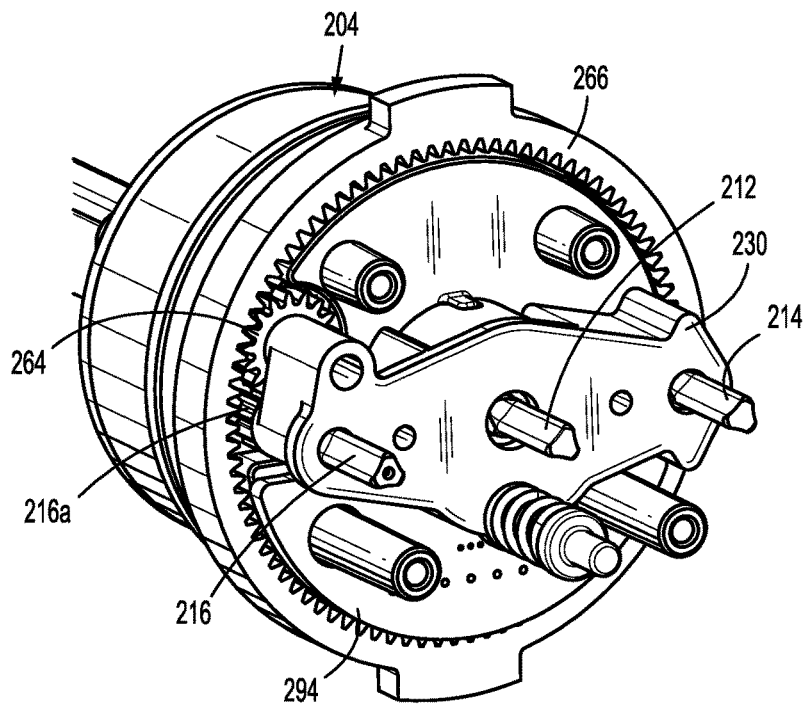
FIG. 38 is a rear, perspective view of the proximal inner housing assembly of FIG. 37 with connector sleeves removed therefrom.
Figure 39:
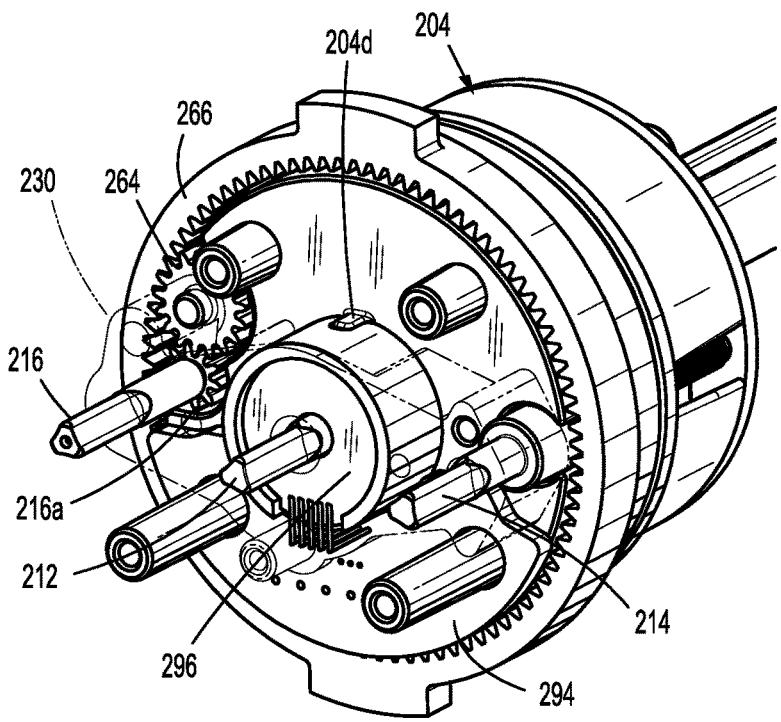
FIG. 39 is a rear, perspective view of the proximal inner housing assembly of FIG. 37 with connector sleeves removed therefrom and the plate bushing shown in phantom.

As illustrated in FIGS. 38, 46 and 47, inner housing assembly 204' may include a reinforcing sleeve 255' disposed about bracket assembly 254' to further reinforce bracket assembly 254'. It is contemplated in an embodiment that reinforcing sleeve 255' may be interposed between first plate 254a' and second plate 254b' of bracket assembly 254'. It is further contemplated that reinforcing sleeve 255' may be interposed between second plate 254b' and a distally oriented face of proximal inner housing assembly 204'.

With particular reference to FIGS. 49-60B, further details and embodiments of proximal electrical assembly 290, distal electrical assembly 400, and the engagement therebetween are illustrated. Proximal electrical assembly 290 and distal electrical assembly 400 are configured to permit rotation of outer tube 206 of adapter assembly 200 with respect to handle housing 102 (FIG. 1A), while maintaining electrical contact between proximal electrical assembly 290 and distal electrical assembly 400.

With reference to FIGS. 52 and 53, distal electrical assembly 400 is shown and includes a contact housing or housing 410, a plurality of electrical contacts 420 extending from housing 410, and a plurality of wires 430 which electrically connect electrical contacts 420 with distal portions of force/rotation transmitting/converting assemblies 240, 250, 260. For example, a first electrical contact 422 is connected to first force/rotation transmitting/converting assembly 240 via a first wire 430a, a second electrical contact 424 is connected to second force/rotation transmitting/converting assembly 250 via a second wire 430b, and a third electrical contact 426 is connected to third force/rotation transmitting/converting assembly 250 via a third wire 430c. Additionally, wires 430 include a first portion 432 which extends from a radially outer portion 412 of housing 410 in a curved manner and in a direction that is generally perpendicular to longitudinal axis "X." A second portion 434 of each wire 430 is electrically coupled to first portion 432 of wires 430 and extends generally distally and longitudinally therefrom.

Figure 54:
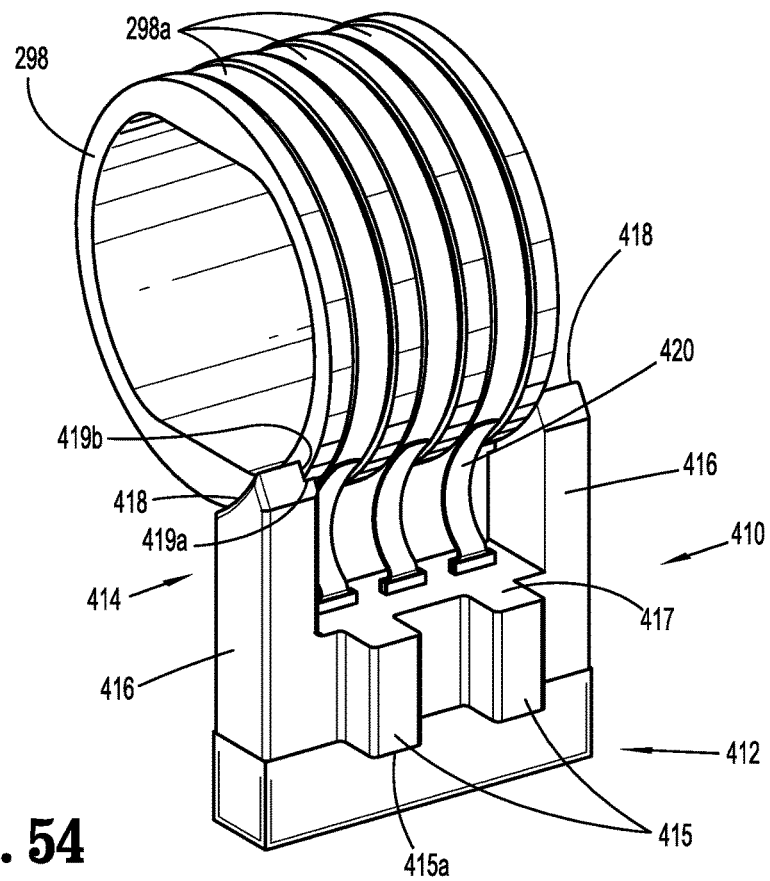
FIG. 54 is a perspective view illustrating the engagement between portions of the proximal and distal electrical assemblies of FIGS. 49-53.
Figure 55:
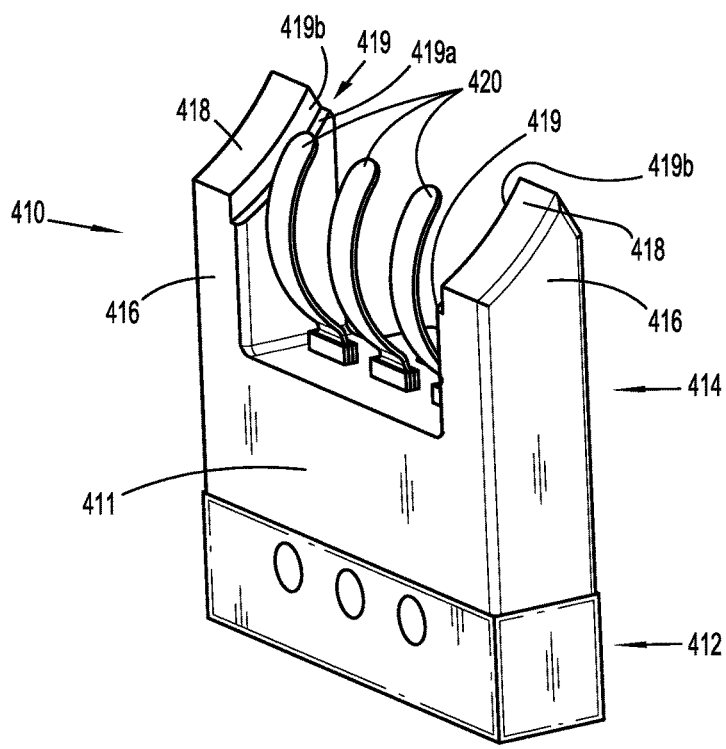
FIG. 55 is a perspective view of the portion of the distal electrical assembly shown in FIG. 54.

With particular reference to FIGS. 54 and 55, a radially inner portion 414 of housing 410 includes a pair of legs 416. Each leg 416 includes a curved portion 418 that is configured to mirror the curvature of slip ring 298. Additionally, each leg 416 includes a curved stepped portion 419. Housing 410 and slip ring 298 are dimensioned and configured such that slip ring 298 is positionable on a surface 419a of stepped portions 419 and between sidewalls 419b of stepped portions 419. This arrangement helps housing 410 maintain contact with slip ring 298 during rotation therebetween, for example.

With continued reference to FIGS. 54 and 55, a plurality of electrical contacts 420 is shown extending from housing 410. Each electrical contact 420 is configured to engage a single electrical contact ring 298a of slip ring 298 (FIG. 54) to transmit electrical signals from that electrical contact ring 298a to a respective wire 430 of distal electrical assembly 400. In the embodiment shown in FIGS. 54 and 55, for example, electrical contacts 420 extend in a cantilevered manner from housing 410 and are curved along a majority of their lengths. Further, the curvature of electrical contacts 420 is opposite from the curvature of slip ring 298 and is opposite from the curvature of curved portion 418 and stepped portion 419 of each leg 416 of housing 410. Additionally, each electrical contact 420 is configured to flex to help maintain contact with electrical contact rings 298a of slip ring 298 upon rotation therebetween, for example. Further, the curvature of electrical contacts 420 enables uninterrupted contact between electrical contacts 420 and electrical contact rings 298a upon rotation of housing 410 in either direction (i.e., clockwise and counter-clockwise) with respect to slip ring 298.

Referring now to FIGS. 56A-60B, other embodiments of electrical contacts 420 are shown. In FIGS. 56A-60B, portions of slip ring 298 and/or electrical contact rings 298a are omitted and/or out of scale for clarity purposes. FIGS. 56A and 56B illustrate electrical contacts 420a which include a leg 422a and a foot 424a. Each of leg 422a and foot 424a is generally linear. Foot 424a extends from leg 422a at an angle $\alpha_a$. It is envisioned that angle $\alpha_a$ is between about 100° and about 160°, or equal to about 135°. In this embodiment, an electrical connection is made at one location "EC1" where foot 424a contacts electrical contact ring 298a.

With reference to FIGS. 57A and 57B, another embodiment of an electrical contact 420b is shown. Each electrical contact 420b includes a pair of legs 422b, and a foot 424b extending from each leg 422b such that each foot 424b extends in an opposite direction from the other foot 424b. It is also envisioned that each electrical contact 420b includes a single leg 422b with two feet 424b extending therefrom in opposite directions. Each foot 424b extends from its respective leg 422b at an angle $\alpha_b$. It is envisioned that angle $\alpha_b$ is between about 100° and about 160°, or equal to about 135°. It is further envisioned that each foot 424b extends from its respective leg 422b at the same angle as the opposite foot 424b or at a different angle from the opposite foot 424b. In this embodiment, an electrical connection is made at two locations "EC1" and "EC2"—one where each foot 424b contacts electrical contact ring 298a. EC1 and EC2 provide redundant contacts to maintain electrical connections, for instance due to imperfection in surface 298a.

With reference to FIGS. 58A and 58B, another embodiment of an electrical contact 420c is shown. Electrical contact 420c includes a leg 422c, an ankle 423c, and a foot 424c. Ankle 423c extends from leg 422c at a first angle $\alpha_{c1}$, and foot 424c extends from ankle 423c at a second angle $\alpha_{c2}$. It is envisioned that first angle $\alpha_{c1}$ is between about 150° and about 175°, or equal to about 165°. And it is envisioned that second angle $\alpha_{c2}$ is between about 10° and about 60°, or equal to about 30°. Additionally, foot 424c is curved along its length, e.g., its entire length. It is envisioned that the curvature of foot 424c is equal to or greater than the curvature of electrical contact rings 298a and/or slip ring 298. In this embodiment where the curvature of foot 424c is greater than the curvature of electrical contact ring 298a (FIG. 58a), an electrical connection is made at two locations "EC1" and "EC2"—one where each foot 424c contacts electrical contact ring 298a. In this embodiment, the foot 424c opens and conforms to ring 298a maintaining multiple points of contact.

Referring to FIGS. 59A and 59B, another embodiment of an electrical contact 420d is shown. Electrical contact 420d includes a yoke 422d including two legs 424d, and a flexible contact 426d spanning between legs 424d. Each leg 424d of yoke 422d includes an opening 425d configured to allow a portion of flexible contact 426d to extend therethrough. Flexible contact 426d includes an elongated portion 427d with an enlarged portion 428d at each end thereof. Elongated portion 427d of flexible contact 426d includes a smaller dimension than opening 425d of leg 424d, thus allowing elongated portion 427d to extend through openings 425d. Enlarged portions 428d of flexible contact 426d include a larger dimension than opening 425d of leg 424d, thus preventing enlarged portions 428d from being able to extend through openings 425d. Accordingly, flexible contact 426d is maintained between legs 424d of yoke 422d. In this embodiment, an electrical connection is made at one location "EC1" where flexible contact 426d contacts electrical contact ring 298a. Additionally, it is envisioned that since flexible contact 426d has the ability to flex with respect to yoke 422d, electrical contact 420d enables tolerances of electrical contact 420d and/or slip ring 298 to be reduced.

With reference to FIGS. 60A and 60B, another embodiment of an electrical contact 420e is shown. Electrical contact 420e includes a leg 422e and a ring 424e extending therefrom. Ring 424e is configured to wrap at least partially around electrical contact ring 298a, and to have approximately the same radius of curvature of electrical contact ring 298a along at least a portion of its length, thus maintaining an infinite amount of electrical connections therebetween. It is envisioned that ring 424e and electrical contact ring 298a contact each other for greater than 180°. It is further envisioned that ring 424e forms between about 180° and about 360° of a circle. In embodiments where ring 424e forms greater than about 180° of a circle, it is disclosed that ring 424e is flexible enough to flex a sufficient amount during assembly to allow ring 424e to be installed on electrical contact ring 298a. That is, it is disclosed that a first end 425e of ring 424e and a second end 426e of ring 424e can be separated by a distance that is greater than the diameter of electrical contact ring 298a.

Referring now to FIGS. 61-74, various embodiments of a guide 500 are shown. Generally, guide 500 is configured to help maintain engagement between housing 410 and slip ring 298 during assembly. In each of the embodiments, guide 500 includes a holder portion 510 and a spacer 550. Spacer 550 is immovably affixed to holder portion 510 and extends distally therefrom. Spacer 550 is configured to maintain slip ring 298 a predetermined distance proximally from slip ring cannula 700. Additionally, spacer 550 includes a plurality of arcuate, longitudinal passageways 552 which are configured to allow the plurality of wires 430 to pass therethrough.

Figure 61:
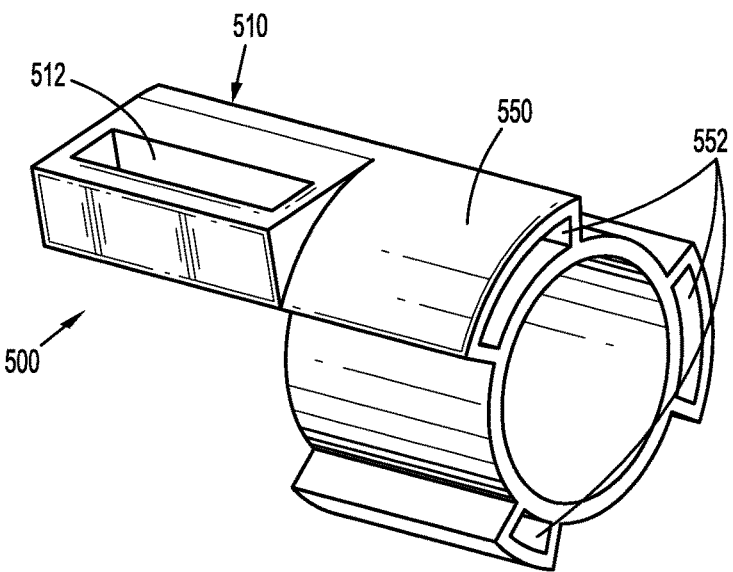
FIG. 61 is a perspective view of a guide in accordance with an embodiment of the present disclosure.
Figure 62:
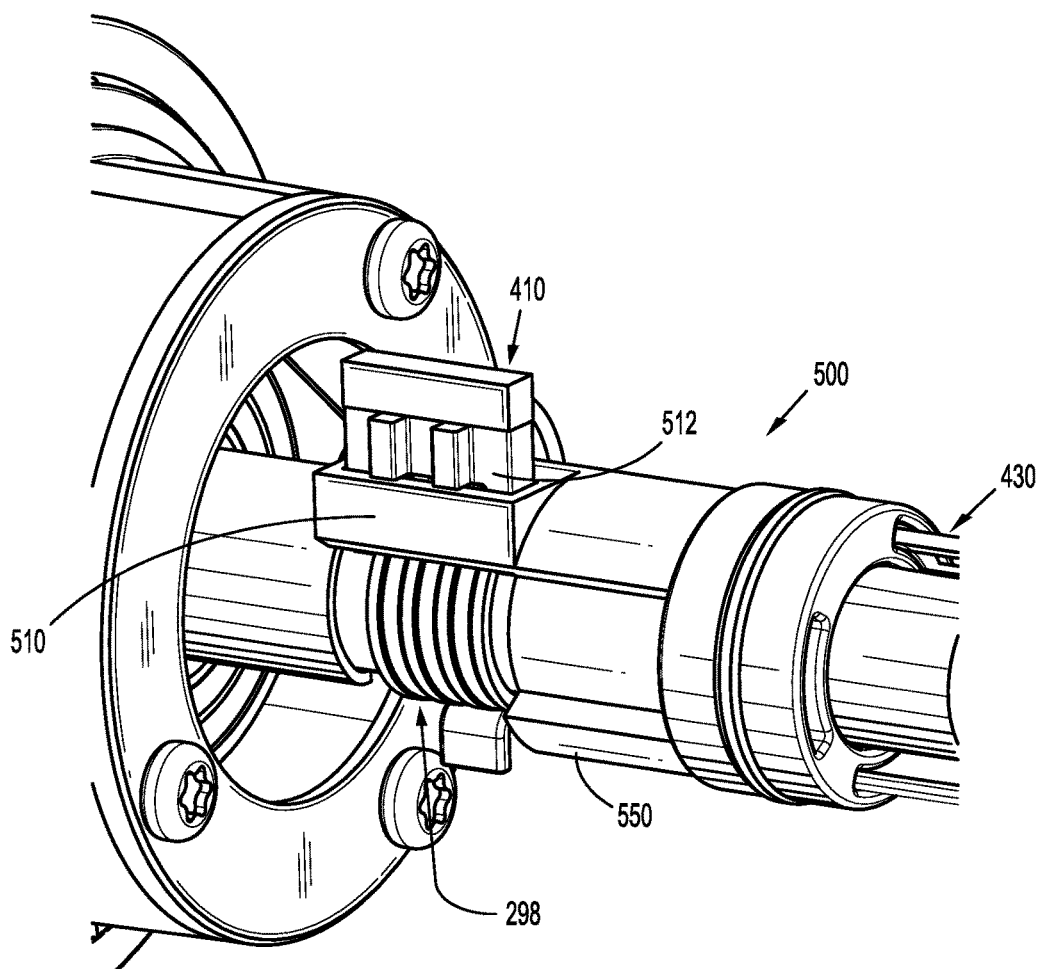
FIG. 62 is a perspective view of a portion of the surgical device of the present disclosure including the guide of FIG. 61.

With particular reference to FIGS. 61 and 62, a first embodiment of a guide is shown and is indicated as reference character 500. A holder portion 510 of guide 500 includes a rectangular aperture 512 extending therethrough. As shown in FIG. 62, rectangular aperture 512 is configured to allow a portion of housing 410 to extend therethrough. For instance, it is envisioned that legs 416 (obscured from view in FIG. 62) of housing 410 are insertable through rectangular aperture 512, and that a ledge 417 (see FIG. 54) of housing 410 abuts holder portion 510, thus preventing additional insertion of housing 410 through rectangular aperture 512. The perimeter of rectangular aperture 512 is slightly larger than the perimeter of the portion of housing 410 that extends therethrough, thus enabling a friction fit engagement therebetween.

Figure 63:
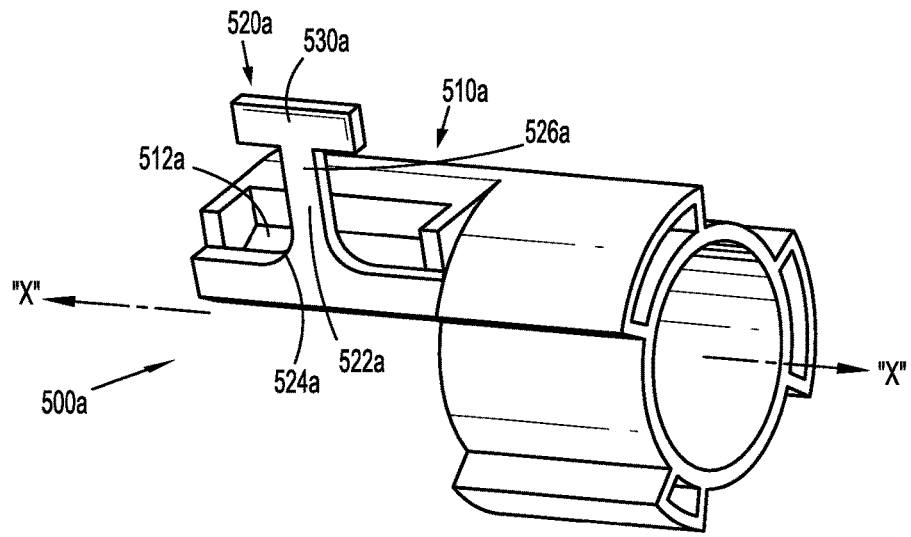
FIG. 63 is a perspective view of a guide in accordance with an embodiment of the present disclosure.
Figure 64:
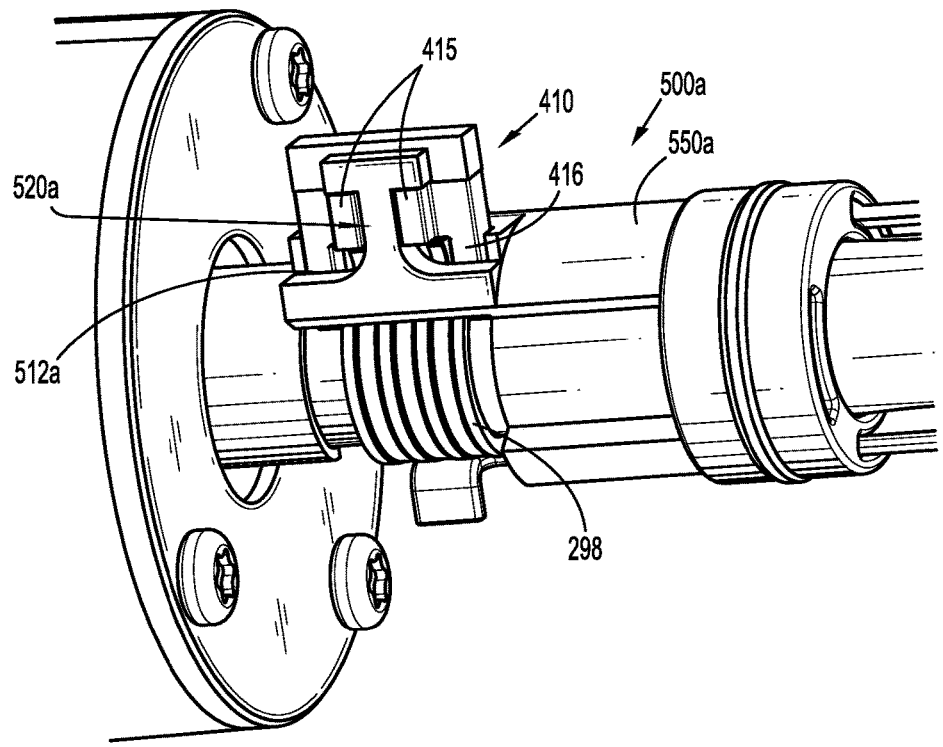
FIG. 64 is a perspective view of a portion of the surgical device of the present disclosure including the guide of FIG. 63.

Referring to FIGS. 63 and 64, another embodiment of a guide is shown and is referenced by character 500a. A holder portion 510a of guide 500a includes a rectangular aperture 512a extending therethrough. Additionally, holder portion 510a of guide 500a includes a flexible tee 520a extending adjacent rectangular aperture 512a and extending radially away from the longitudinal axis "X." Flexible tee 520a includes a shaft 522a and crown 530a. A first portion 524a of shaft 522a is flared and is in contact with remainder of holder portion 510a, and a second portion 526a of shaft 522a engages crown 530a.

As shown in FIG. 64, rectangular aperture 512a is configured to allow a portion of housing 410 to extend therethrough. For instance, it is envisioned that legs 416 of housing 410 are insertable through rectangular aperture 512a, and that ledge 417 (see FIG. 54) of housing 410 abuts holder portion 510a, thus preventing additional insertion of housing 410 through rectangular aperture 512a. To further maintain guide 500a in contact with housing 410, shaft 522a of flexible tee 520a is configured to extend between a pair of projections 415 of housing 410, and crown 530a is configured to abut a radially-outer surface 415a of projections 415 (see FIG. 54). During installation between guide 500a and housing 410, flexible tee 520a is configured to flex away from housing 410 to allow housing 410 to be partially inserted into rectangular aperture 512a of holder portion 510a. Subsequently, flexible tee 520a is configured to return to its non-flexed position to the location shown in FIG. 64.

Figure 65:
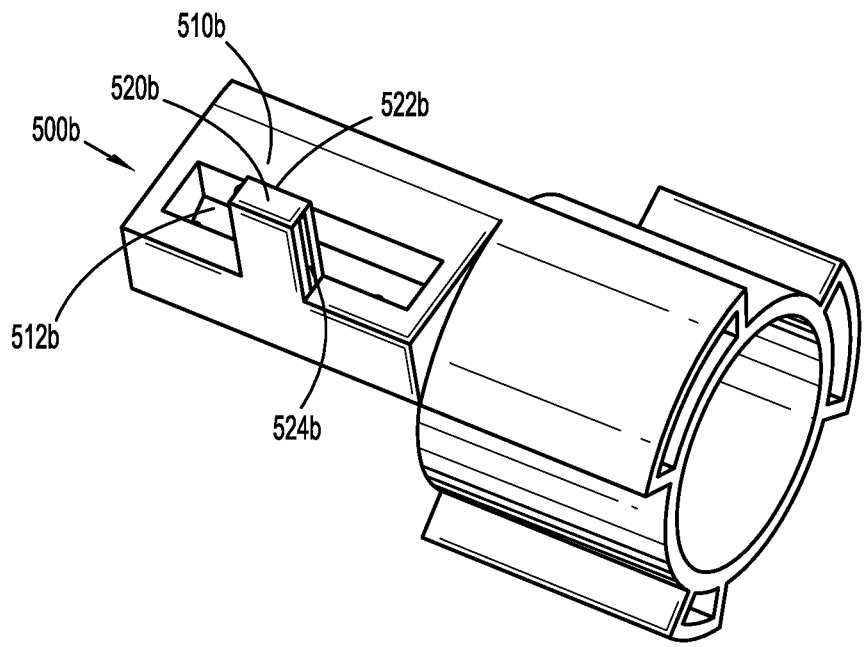
FIG. 65 is a perspective view of a portion of a guide in accordance with an embodiment of the present disclosure.
Figure 66:
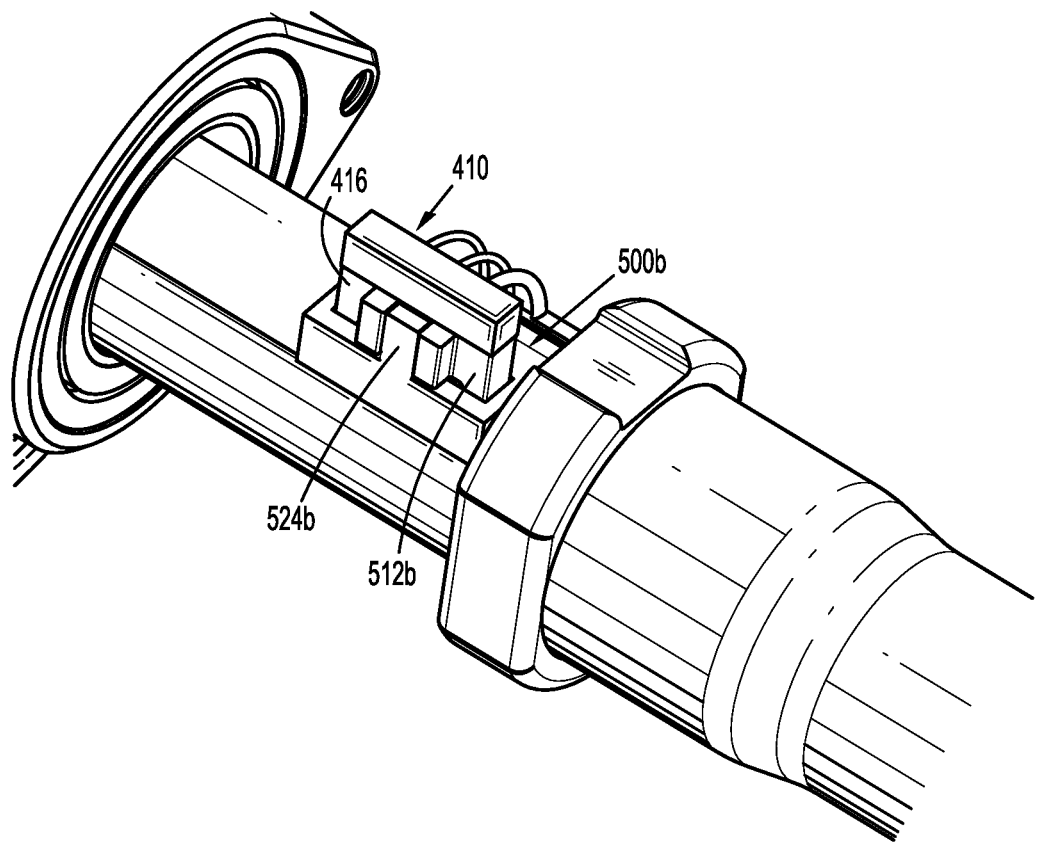
FIG. 66 is a perspective view of a portion of the surgical device of the present disclosure including the guide of FIG. 65.

With reference to FIGS. 65 and 66, another embodiment of a guide is shown and is referred to by reference character 500b. A holder portion 510b of guide 500b includes a rectangular aperture 512b extending therethrough. Additionally, holder portion 510b of guide 500b includes a post 520b extending adjacent rectangular aperture 512b and extending radially away from the longitudinal axis "X." In disclosed embodiments, post 520b includes a plurality of ribs 524b extending along an inner surface 522b of post 520b and extending radially away from the longitudinal axis "X."

As shown in FIG. 66, rectangular aperture 512b is configured to allow a portion of housing 410 to extend therethrough. For instance, it is envisioned that legs 416 of housing 410 are insertable through rectangular aperture 512c, and that ledge 417 (see FIG. 54) of housing 410 abuts holder portion 510b, thus preventing additional insertion of housing 410 through rectangular aperture 512b. To further maintain guide 500b in contact with housing 410, post 520b of holder portion 510b is configured to extend between pair of projections 415 of housing 410 (see FIG. 54). Additionally, ribs 524b on post 520b are designed to be crushed during installation between guide 500b and housing 410, thus providing an increased frictional engagement therebetween.

Figure 67:
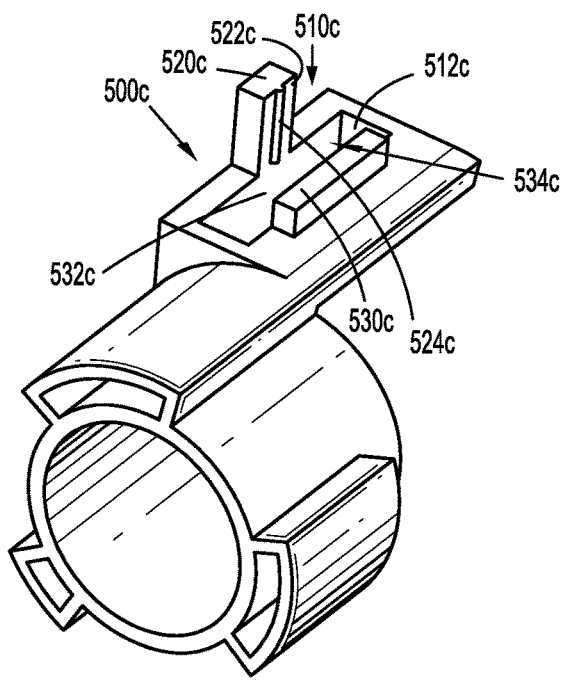
FIG. 67 is a perspective view of a portion of a guide in accordance with another embodiment of the present disclosure.
Figure 68:
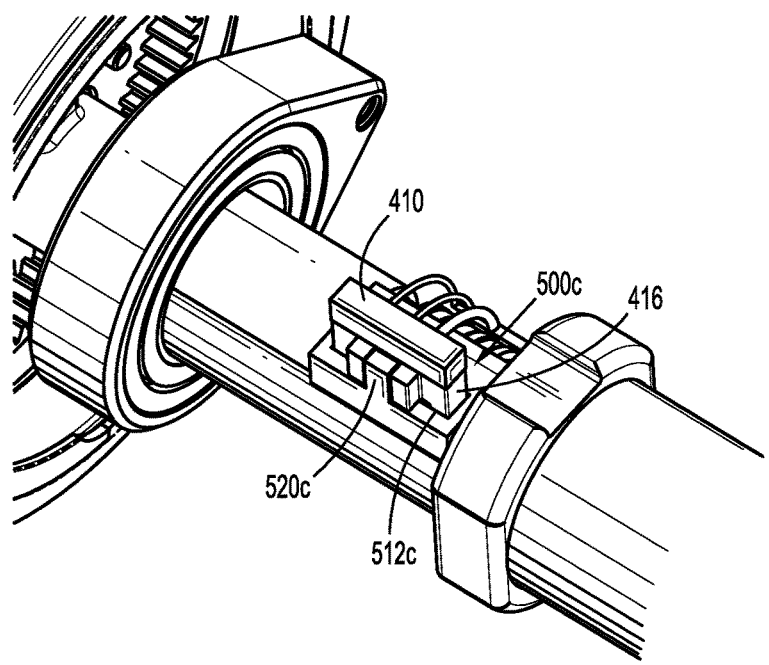
FIG. 68 is a perspective view of a portion of the surgical device of the present disclosure including the guide of FIG. 67.

With reference to FIGS. 67-68, another embodiment of a guide is shown and is referred to by reference character 500c. A holder portion 510c of guide 500c includes a rectangular aperture 512c extending therethrough. Additionally, holder portion 510c of guide 500c includes a first post 520c and a second post 530c extending adjacent rectangular aperture 512c and extending radially away from the longitudinal axis "X." In disclosed embodiments, at least one of first post 520c and second post 530c includes a plurality of ribs 524c, 534c extending along an inner surface 522c, 532c of the respective first post 520c and/or second post 530c, and extending radially away from the longitudinal axis "X."

As shown in FIG. 68, rectangular aperture 512c is configured to allow a portion of housing 410 to extend therethrough. For instance, it is envisioned that legs 416 of housing 410 are insertable through rectangular aperture 512c, and that ledge 417 (see FIG. 54) of housing 410 abuts holder portion 510c, thus preventing additional insertion of housing 410 through rectangular aperture 512c. To further maintain guide 500c in contact with housing 410, first post 520c of holder portion 510c is configured to extend between the pair of projections 415 of housing 410 (see FIG. 54), and second post 530c is configured to abut a rear wall 411 of housing 410 (see FIG. 55). Additionally, ribs 524c, 534c on first post 520c and/or second post 530c, respectively, are designed to be crushed during installation between guide 500c and housing 410, thus providing an increased frictional engagement therebetween.

Figure 69:
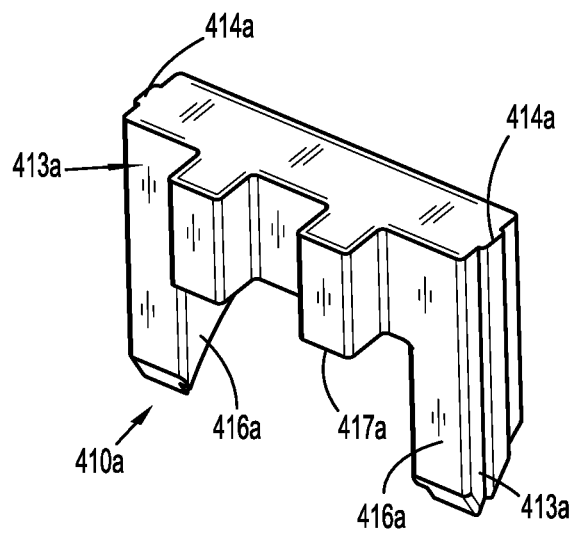
FIG. 69 is a perspective view of a housing in accordance with an embodiment of the present disclosure.
Figure 70:
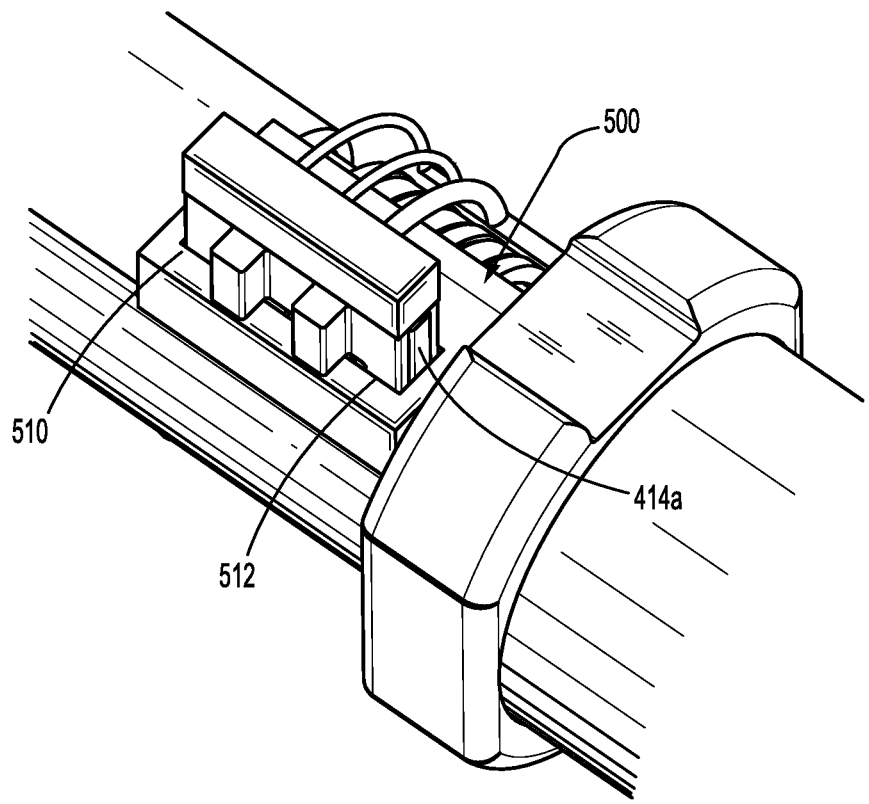
FIG. 70 is a perspective view of a portion of the surgical device of the present disclosure including the housing of FIG. 69 engaged with the guide of FIG. 60.

With reference to FIGS. 69 and 70, a second embodiment of housing 410a is shown, which is configured to engage first embodiment of guide 500 (FIG. 70). As discussed above, holder portion 510 of guide 500 includes a rectangular aperture 512 extending therethrough. Rectangular aperture 512 is configured to allow a portion of housing 410a to extend therethrough. For instance, it is envisioned that legs 416a of housing 410a are insertable through rectangular aperture 512, and that a ledge 417a (see ledge 417 in FIG. 54) of housing 410a abuts holder portion 510, thus preventing additional insertion of housing 410a through rectangular aperture 512. The perimeter of rectangular aperture 512 is slightly larger than the perimeter of the portion of housing 410a that extends therethrough, thus enabling a friction fit engagement therebetween. Additionally, housing 410a includes a plurality of ribs 414a extending along at least one lateral side 413a of housing 410a. Ribs 414a are designed to fill any voids between lateral sides 413a of housing 410a and guide 500 to increase frictional engagement therebetween.

Figure 71:
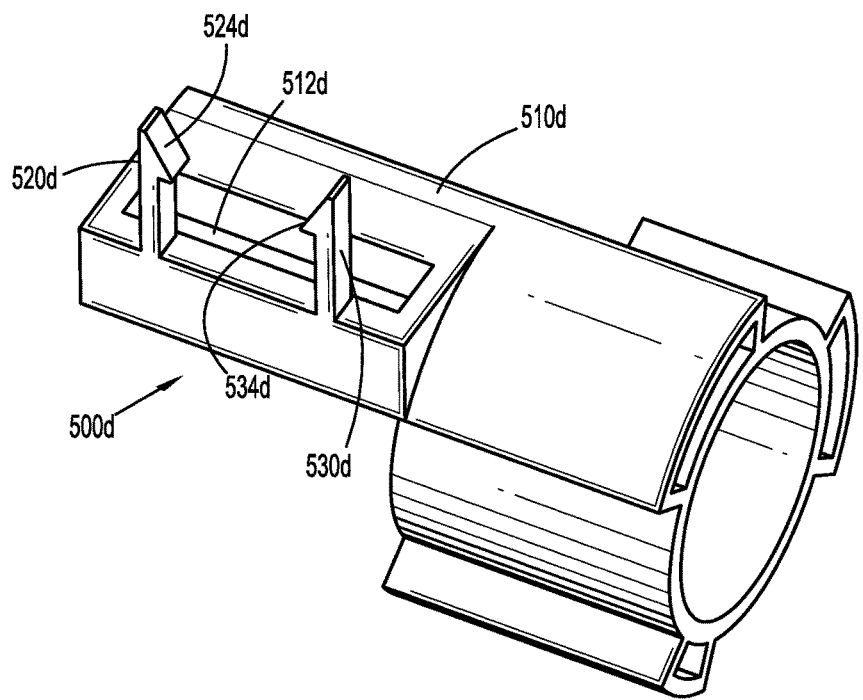
FIG. 71 is a perspective view of a guide in accordance with yet another embodiment of the present disclosure.
Figure 72:
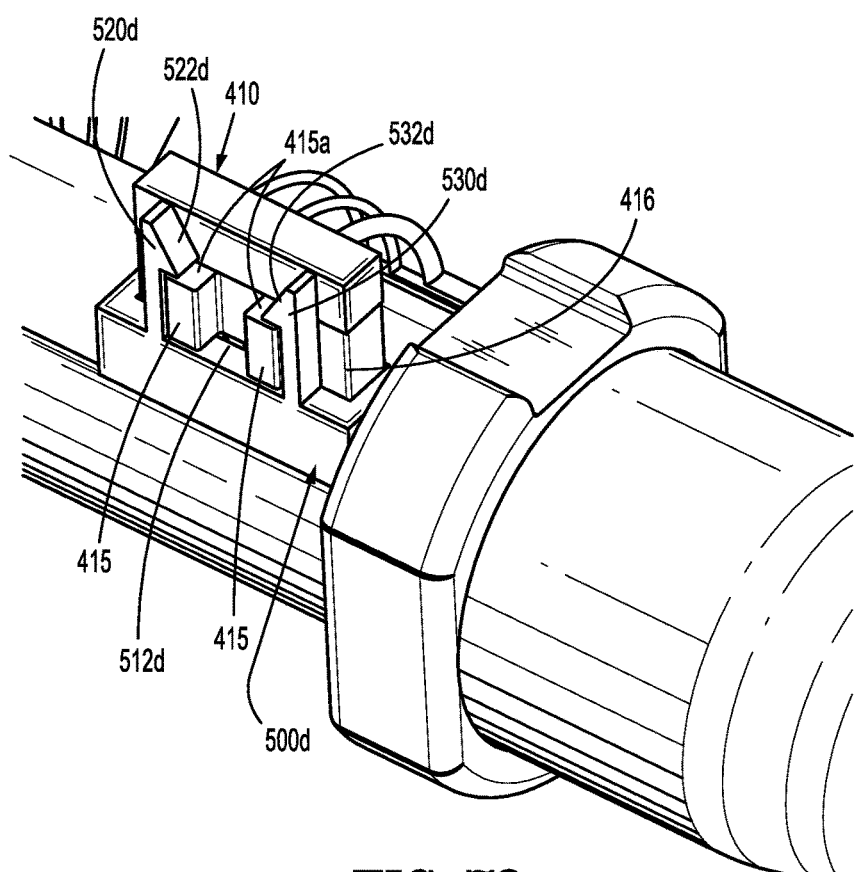
FIG. 72 is a perspective view of a portion of the surgical device of the present disclosure including the guide of FIG. 71.

With reference to FIGS. 71-72, another embodiment of a guide is shown and is referred to by reference character 500d. A holder portion 510d of guide 500d includes a rectangular aperture 512d extending therethrough. Additionally, holder portion 510d of guide 500d includes a first flexible tab 520d and a second flexible tab 530d extending adjacent rectangular aperture 512d and extending radially away from the longitudinal axis "X." In the illustrated embodiment, each of first flexible tab 520d and second flexible tab 530d includes a one-way ratchet tooth 524d, 534d, respectively, thereon.

As shown in FIG. 72, rectangular aperture 512d is configured to allow a portion of housing 410 to extend therethrough. For instance, it is envisioned that legs 416 of housing 410 are insertable through rectangular aperture 512d, and that ledge 417 (see FIG. 54) of housing 410 abuts holder portion 510d, thus preventing additional insertion of housing 410 through rectangular aperture 512d. To further maintain guide 500d in contact with housing 410, ratchet teeth 524d, 534d of first and second flexible tabs 520d, 530d, respectively, are configured to engage radially-outer surfaces 415a of projections 415 (see FIGS. 54 and 72). During installation between guide 500d and housing 410, flexible tabs 520d and 530d are configured to flex away from housing 410 in response to engagement between ratchet teeth 524d, 534d and ledge 417 to allow housing 410 to be partially inserted into rectangular aperture 512d of holder portion 510d. Subsequently, flexible tabs 520d and 530d are configured to return to their non-flexed position to the location shown in FIG. 72.

Figure 73:
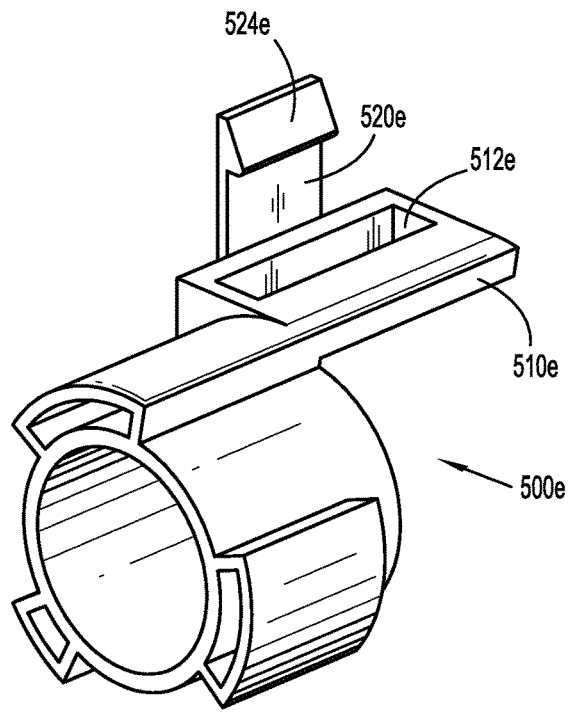
FIG. 73 is a perspective view of a portion of a guide in accordance with still another embodiment of the present disclosure.
Figure 74:
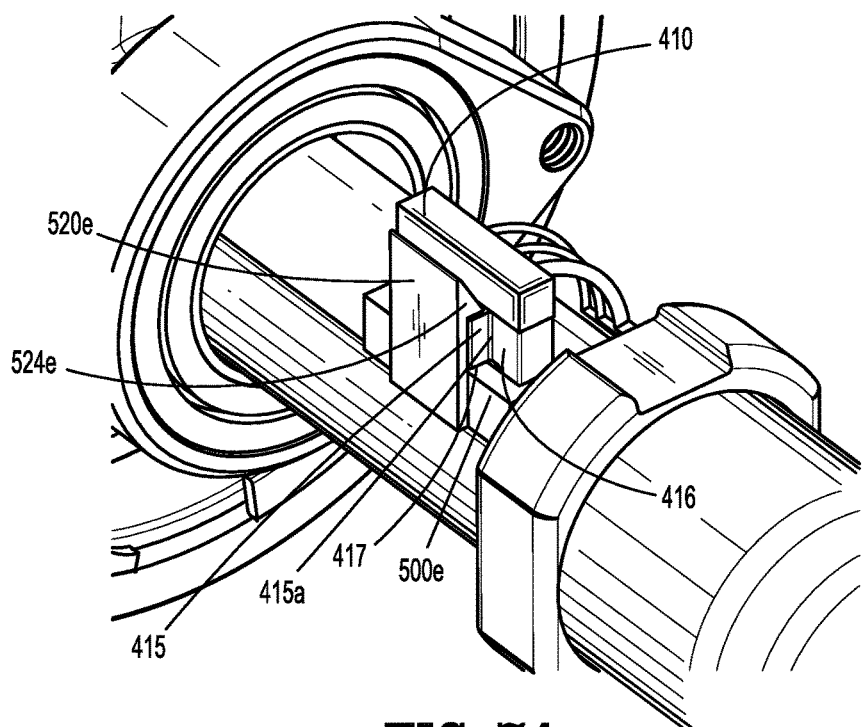
FIG. 74 is a perspective view of a portion of the surgical device of the present disclosure including the guide of FIG. 73.

With reference to FIGS. 73-74, another embodiment of a guide is shown and is referred to by reference character 500e. A holder portion 510e of guide 500e includes a rectangular aperture 512e extending therethrough. Additionally, holder portion 510e of guide 500e includes a flexible tab 520e extending adjacent rectangular aperture 512e and extending radially away from the longitudinal axis "X." In the illustrated embodiment, flexible tab 520e includes a one-way ratchet tooth 524e thereon.

As shown in FIG. 74, rectangular aperture 512e is configured to allow a portion of housing 410 to extend therethrough. For instance, it is envisioned that legs 416 of housing 410 are insertable through rectangular aperture 512e, and that ledge 417 (see FIG. 54) of housing 410 abuts holder portion 510e, thus preventing additional insertion of housing 410 through rectangular aperture 512e. To further maintain guide 500e in contact with housing 410, ratchet tooth 524e of flexible tab 520e is configured to engage radially-outer surfaces 415a of projections 415 (see FIGS. 54 and 74). During installation between guide 500e and housing 410, flexible tab 520e is configured to flex away from housing 410 in response to engagement between ratchet tooth 524e and ledge 417 to allow housing 410 to be partially inserted into rectangular aperture 512e of holder portion 510e. Subsequently, flexible tab 520e is configured to return to its non-flexed position to the location shown in FIG. 74.

Referring now to FIGS. 75-79, a spacer 600 and a slip ring contact holder 650 are shown in accordance with disclosed embodiments. Generally, spacer 600 and slip ring contact holder 650 are configured for mechanical engagement with one another and are configured to help maintain engagement between housing slip ring contact holder 650 and slip ring 298 during assembly. Further, in this embodiment, slip ring contact holder 650 combines some features of housings 410, 410a and guides 500-500e of previous embodiments. That is, in the embodiments disclosed in FIGS. 75-79, only one feature (i.e., slip ring contact holder 650) is necessary instead of two features (i.e., housing 410, 410a and guides 500-500e).

Figure 75:
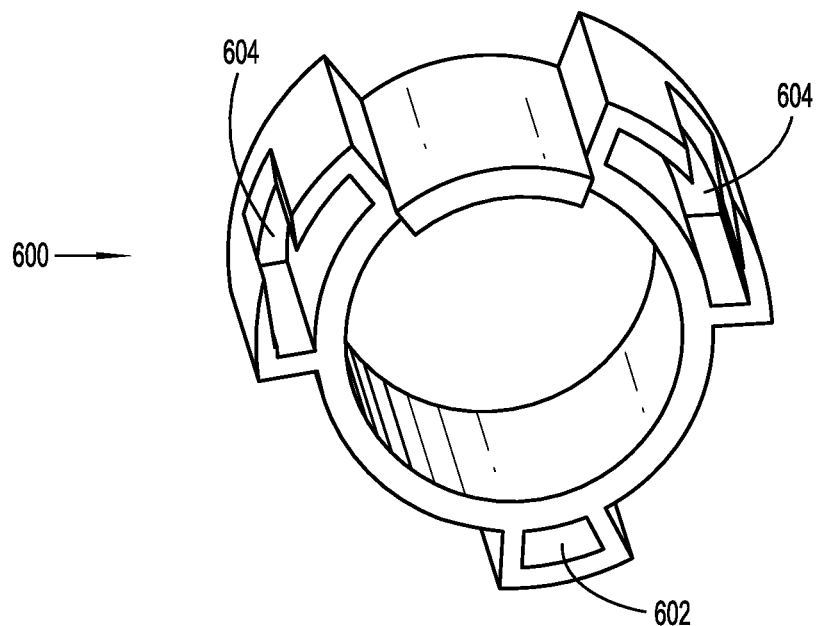
FIG. 75 is a perspective view of a spacer of the surgical device in accordance with an embodiment of the present disclosure.

With reference to FIG. 75, spacer 600 is configured to maintain slip ring 298 a predetermined distance proximally from slip ring cannula 700. Additionally, spacer 600 includes an arcuate, longitudinal passageway 602, and a pair of slots 604. Passageway 602 is configured to allow the plurality of wires 430 (see FIG. 53) to pass therethrough, and each slot 604 is configured to mechanically engage one of two arms 660 of slip ring contact holder 650 for coupling spacer 600 and slip ring contact holder 650 (see FIGS. 76A and 76B).

Figure 76A:
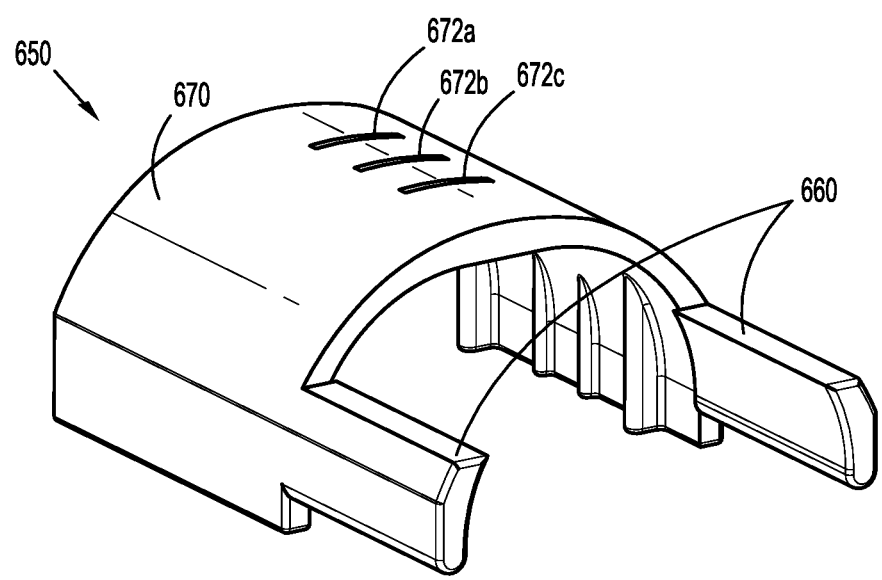
FIGS. 76A and 76B are perspective views of a slip ring contact holder for use with the spacer of FIG. 75 in accordance with embodiments of the present disclosure.
Figure 76B:
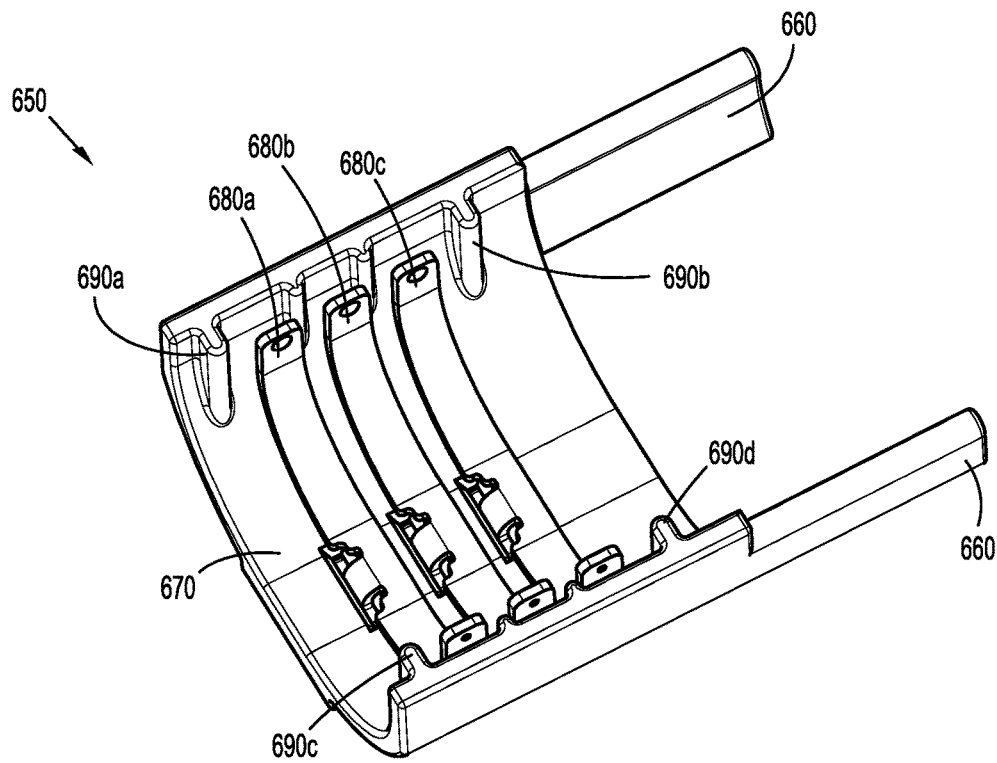

Referring now to FIGS. 76A and 76B, slip ring contact holder 650 includes a body portion 670 and two arms 660 extending longitudinally therefrom. Body portion 670 is generally C-shaped and houses or is configured to house a plurality of contacts 680a, 680b, 680c therein. Body portion 670 is configured to be positioned over slip ring 298 such that each contact 680a, 680b, 680c engages a single contact ring 298a of slip ring 298. Additionally, body portion 670 is rotatable about the longitudinal axis "X" with respect to slip ring 298, thus permitting rotation therebetween while maintaining electrical contact therebetween.

With continued reference to FIGS. 76A and 76B, slip ring contact holder 650 also includes apertures 672a, 672b, 672c extending through body potion 670. Apertures 672a, 672b, 672c are each configured to allow one extension portion 682a, 682b, 682c (see FIG. 77) of contacts 680a, 680b, 680c, respectively to pass therethrough. Each extension portion 682a, 682b, 682c is configured to electrically connect to one of wires 430a, 430b, 430c (see FIG. 53) to electrically connect contacts 680a, 680b, 680c with distal portions of force/rotation transmitting/converting assemblies 240, 250, 260.

Additionally, slip ring contact holder 650 includes alignment tabs 690a, 690b, 690c, 690d configured to engage proximal and distal walls of slip ring 298, and help maintain contact with slip ring 298 during rotation of slip ring contact holder 650, for example.

Figure 77:
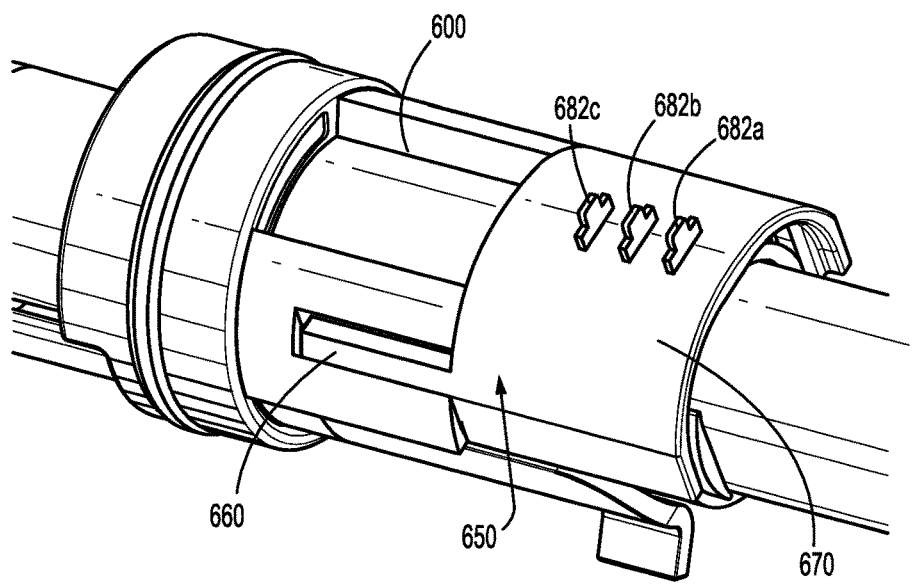
FIGS. 77 and 78 are perspective views of the slip ring contact holder of FIGS. 76A and 76B engaged with the spacer of FIG. 75.
Figure 78:
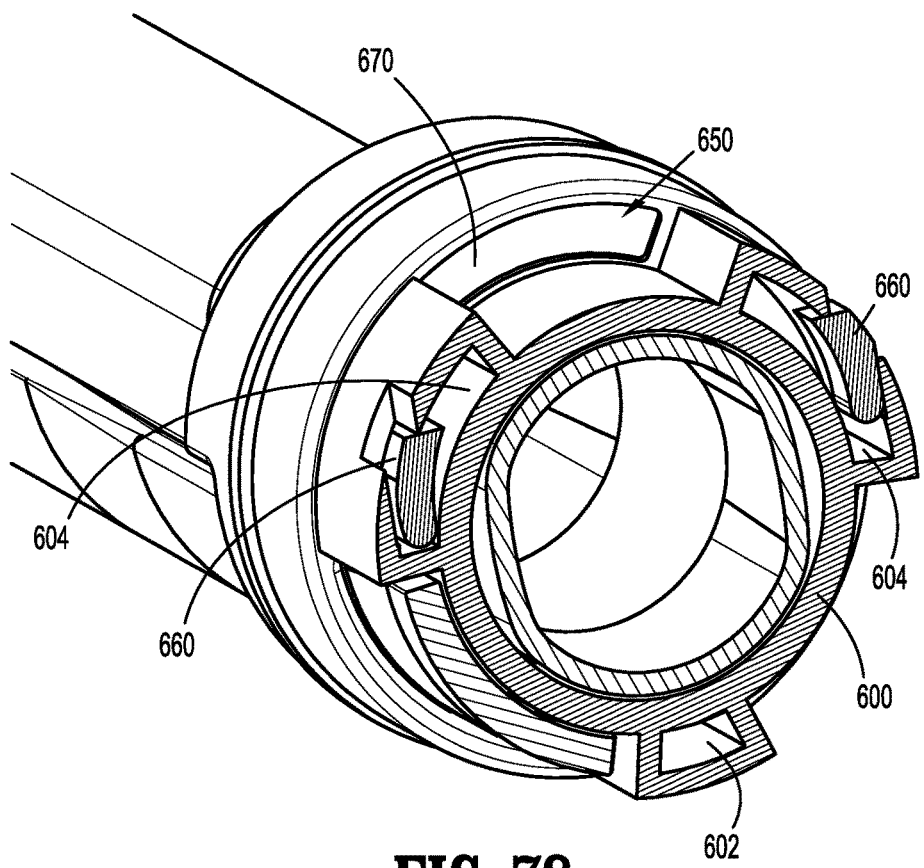
Figure 79:
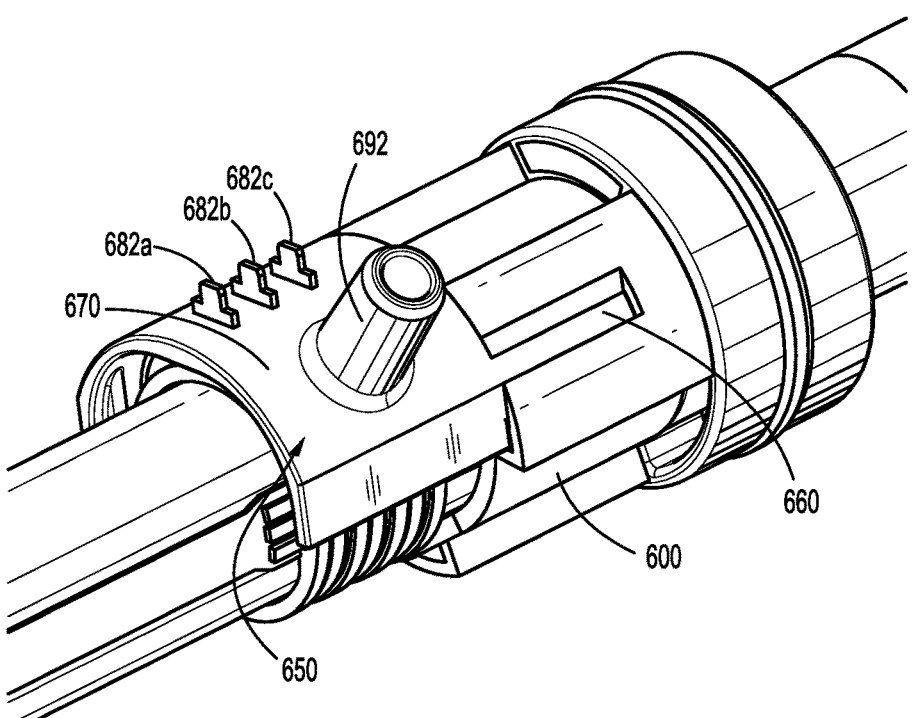
FIG. 79 is a perspective view of a disclosed embodiment of a slip ring contact holder engaged with the spacer of FIG. 75.
Figure 80:
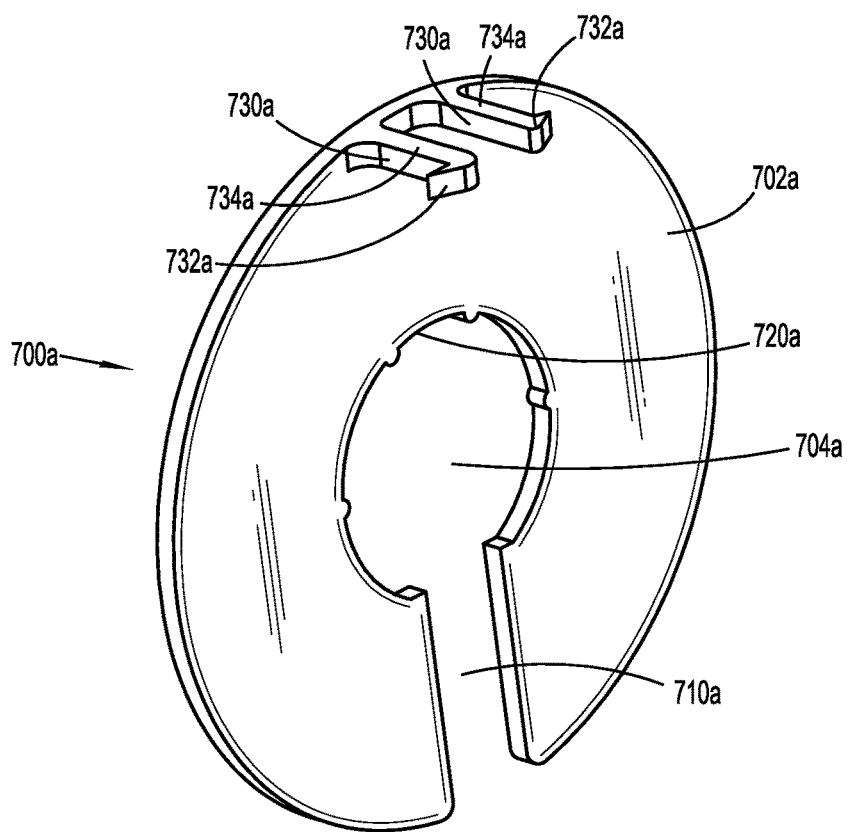
FIG. 80 is a perspective view of a slip ring cannula in accordance with an embodiment of the present disclosure.
Figure 81:
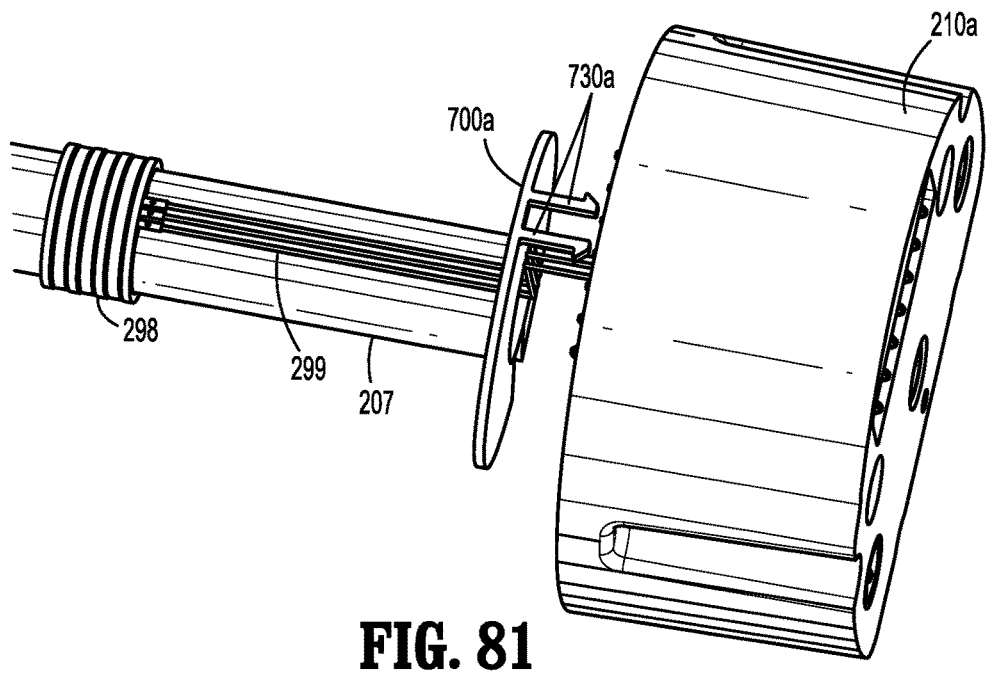
FIG. 81 is a perspective view of the slip ring cannula of FIG. 80 shown over an outer tube of the adapter assembly.
Figure 82:
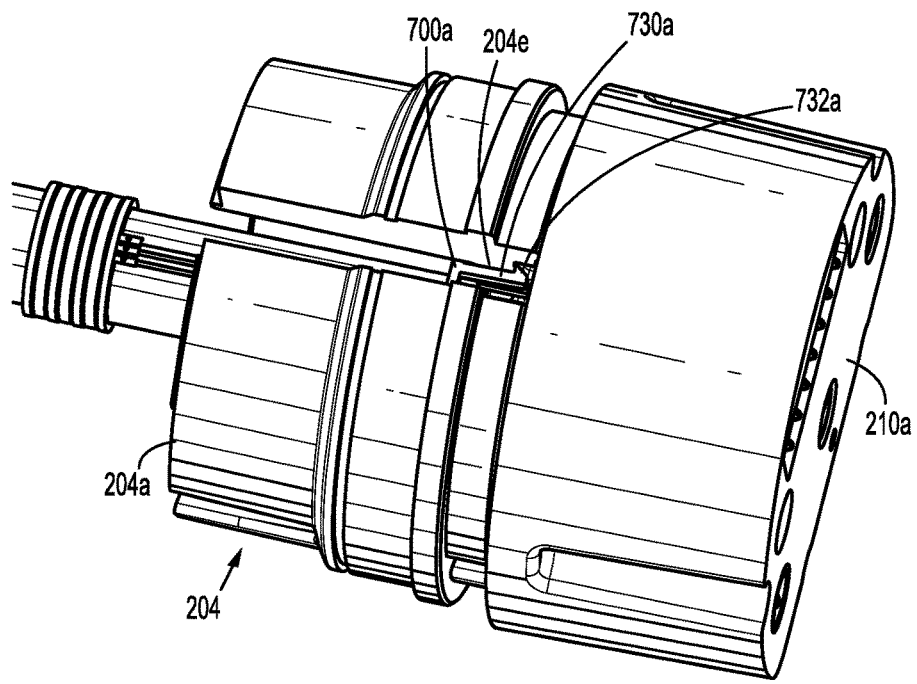
FIGS. 82 and 83 are perspective views of the slip ring cannula of FIGS. 80 and 81 shown over the outer tube of the adapter assembly and engaged with a portion of the inner housing assembly.
Figure 83:
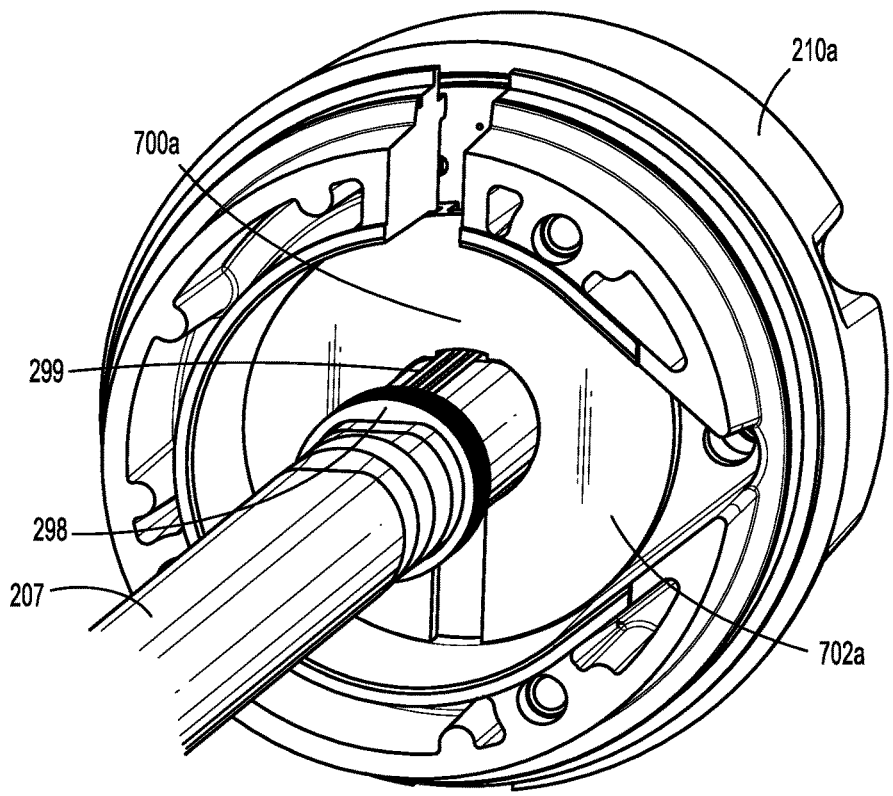

With particular reference to FIGS. 77-79, spacer 600 and slip ring contact holder 650 are shown mechanically engaged. Here, each of the two arms 660 of slip ring contact holder 650 are mated with one slot 604 of spacer 600, thus mechanically coupling spacer 600 and slip ring contact holder 650. It is envisioned that a user can separate spacer 600 from slip ring contact holder 650 by forcing arms 660 toward body portion 670 and out of slots 604. Additionally, the embodiment of slip ring contact holder 650 illustrated in FIG. 79 includes a post 692 extending radially outwardly from body portion 670. It is envisioned that post 692 is configured to engage an inner wall of core tube 207 to help maintain proper radial and/or axial alignment therebetween, for example.

Referring now to FIGS. 15 and 80-85, various embodiments of a sleeve or slip ring cannula 700, 700a, 700b are shown. In general, slip ring cannula 700, 700a, 700b is included as a part of proximal electrical assembly 290 and is positioned on a portion of core tube 207 to protect and/or shield wires 299 extending between slip ring 298 and circuit board 294.

Figure 15:
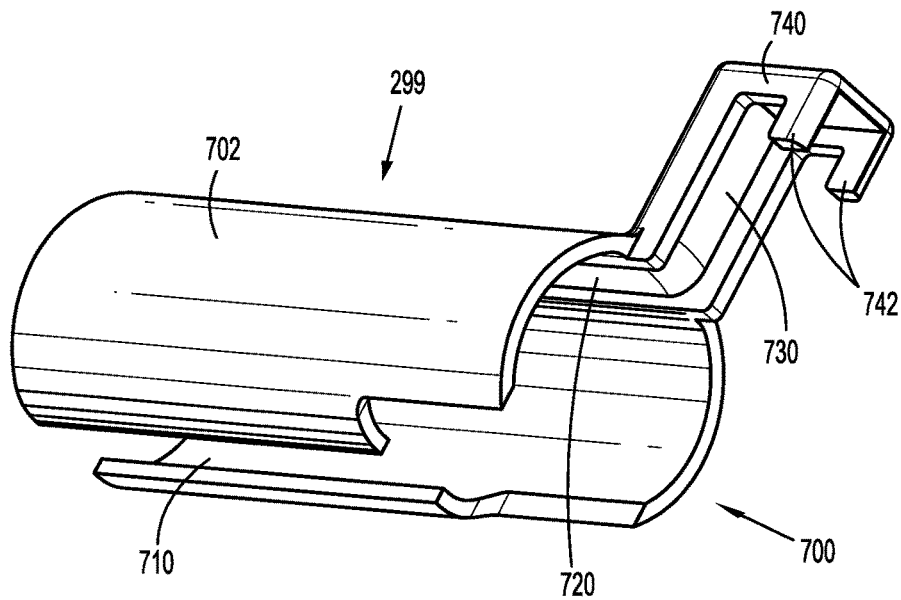
FIG. 15 is a perspective view of a slip ring cannula or sleeve of the adapter assembly of FIGS. 2A and 2B.
Figure 16:
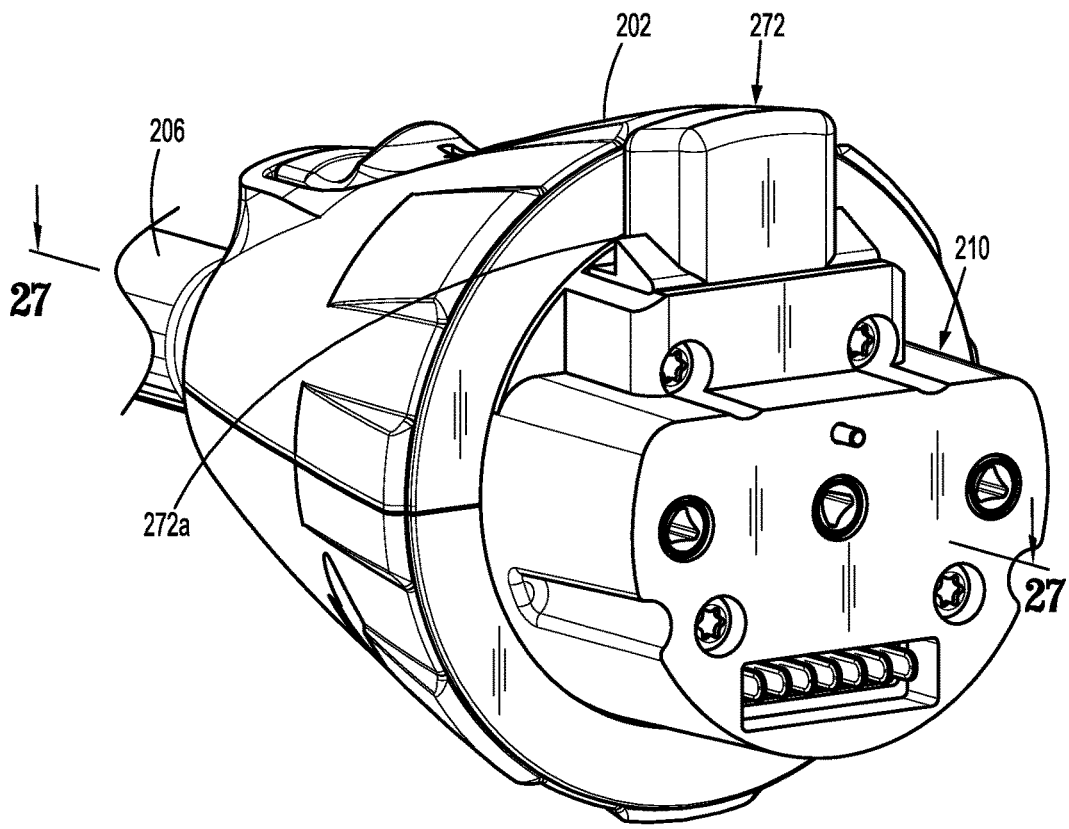
FIG. 16 is an enlarged view of the indicated area of detail of FIG. 2B, illustrating an inner housing assembly of the adapter assembly of FIGS. 2A and 2B.
Figure 17:
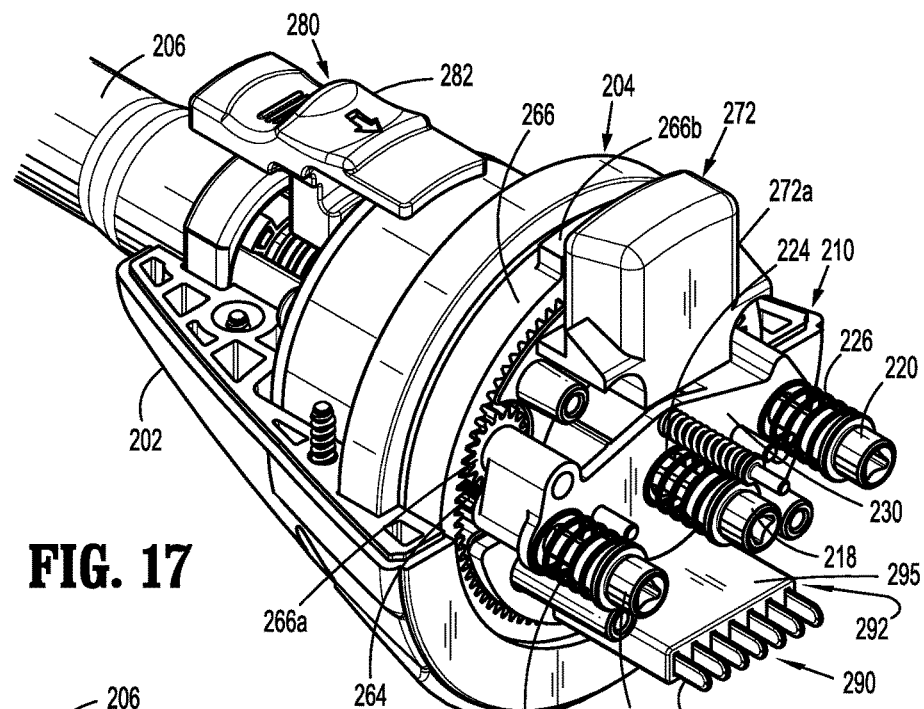
FIG. 17 is a rear, perspective view of the inner housing assembly of FIG. 16 with an outer knob housing half-section and a proximal cap removed therefrom.
Figure 18:
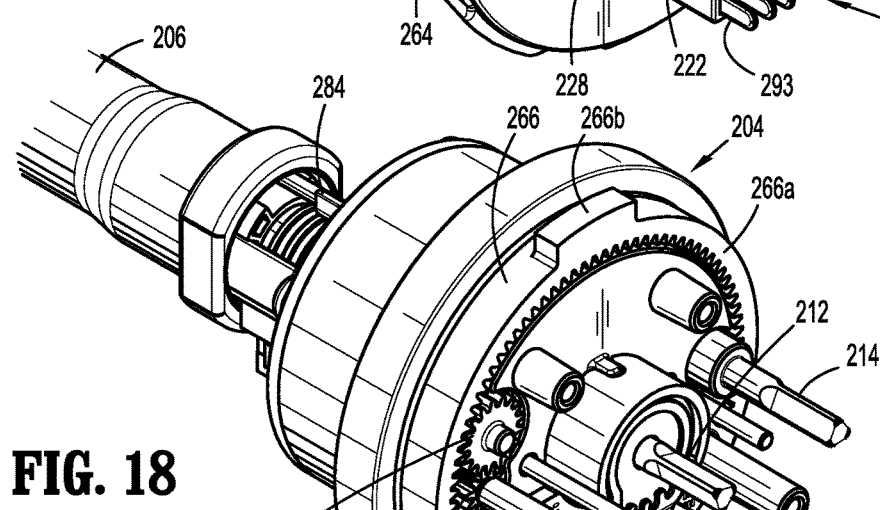
FIG. 18 is a rear, perspective view of the inner housing assembly of FIG. 16 with the outer knob housing, the proximal cap and a bushing plate removed therefrom.
Figure 19:
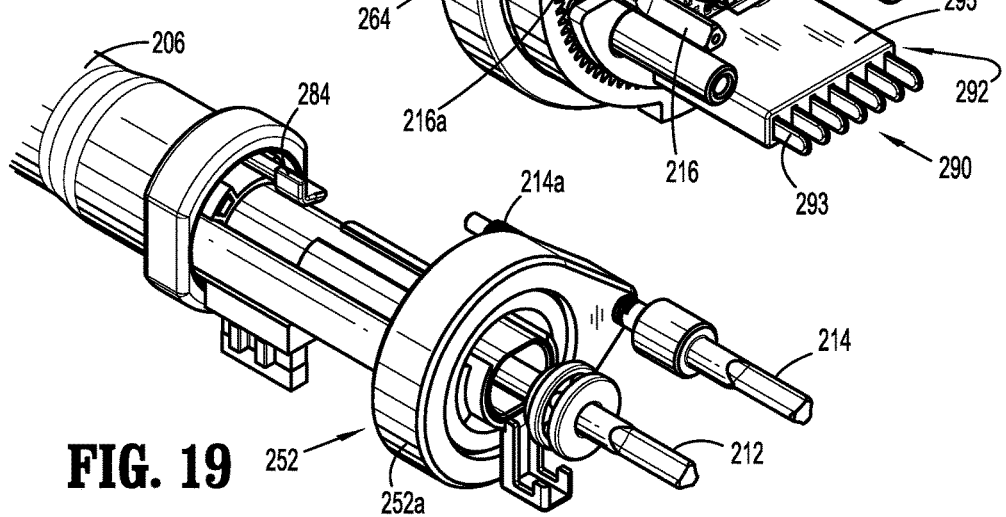
FIG. 19 is a rear, perspective view of the inner housing assembly of FIG. 16 with the outer knob housing, the proximal cap, the bushing plate and an inner housing removed therefrom.
Figure 20:
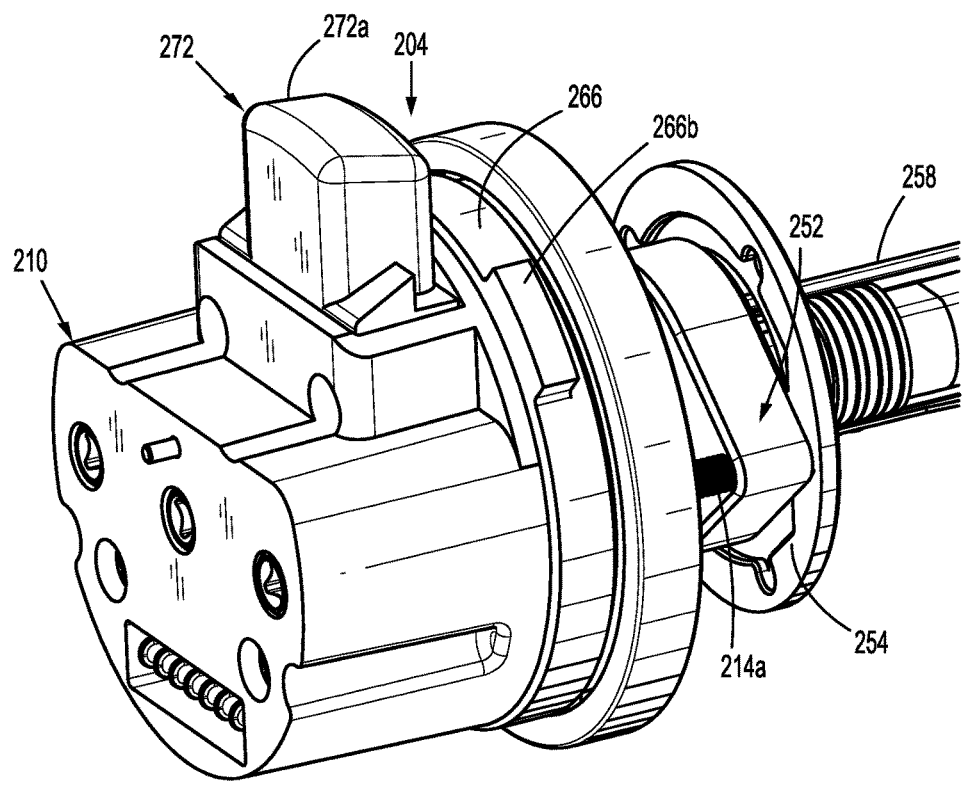
FIG. 20 is a rear, perspective view of the an alternative embodiment of inner housing assembly similar to that shown in FIG. 16 with the outer knob housing and the proximal inner housing removed therefrom.
Figure 21:
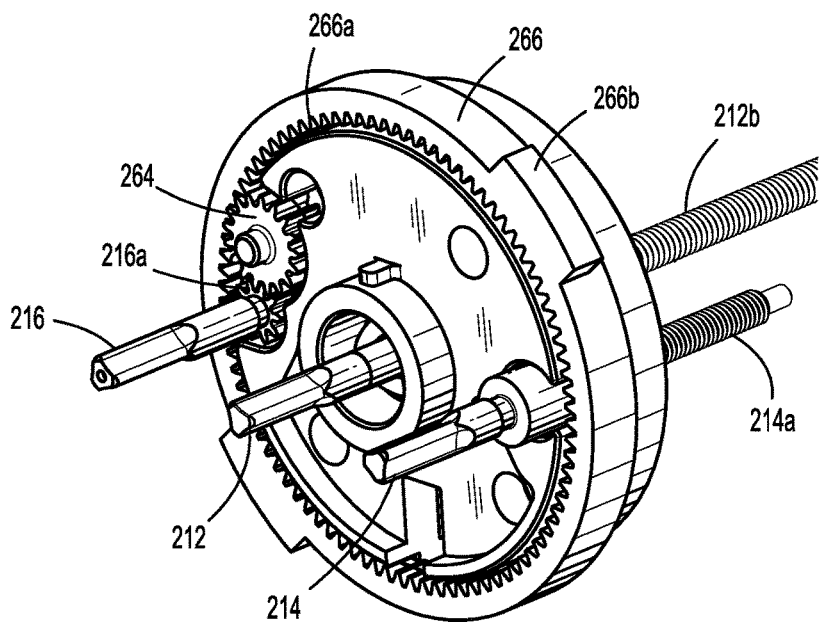
FIG. 21 is a rear, perspective view of the inner housing assembly of FIG. 20 with the outer knob housing, the proximal inner housing and the articulation assembly removed therefrom.
Figure 22:
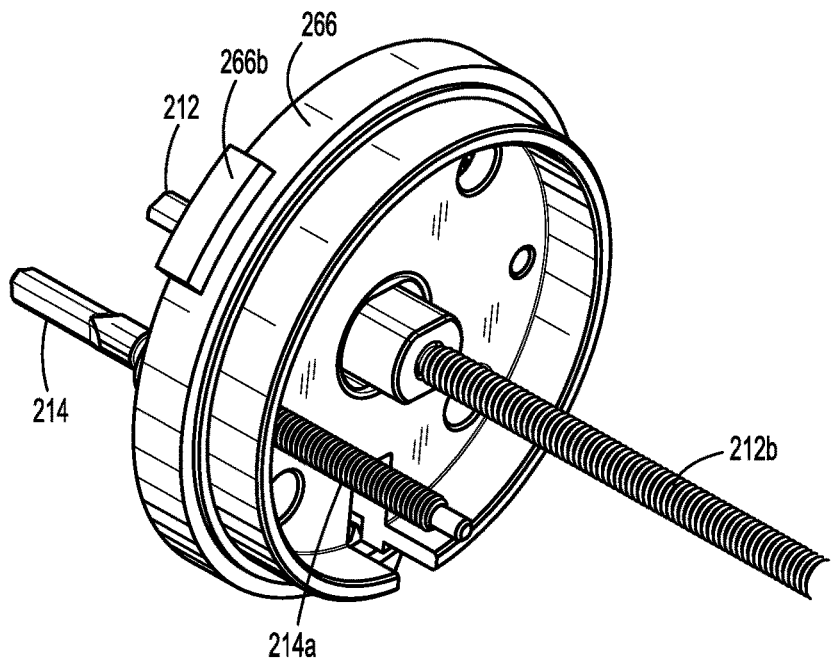
FIG. 22 is a front, perspective view of the inner housing assembly of FIG. 20 with the outer knob housing, the proximal inner housing and the articulation assembly removed therefrom.
Figure 23:
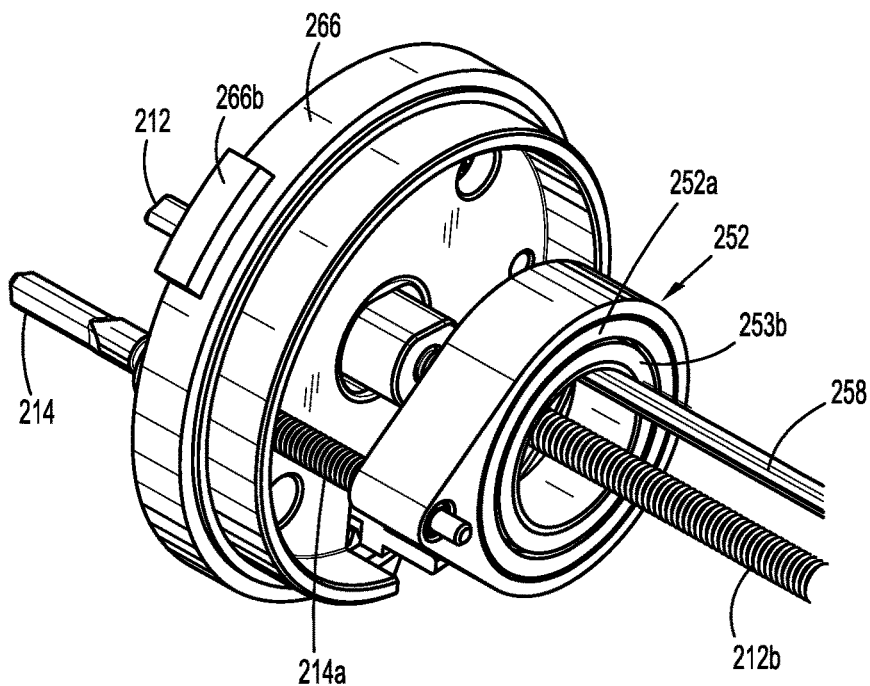
FIG. 23 is a front, perspective view of the inner housing assembly of FIG. 20 with the outer knob housing and the proximal inner housing removed therefrom.
Figure 24:
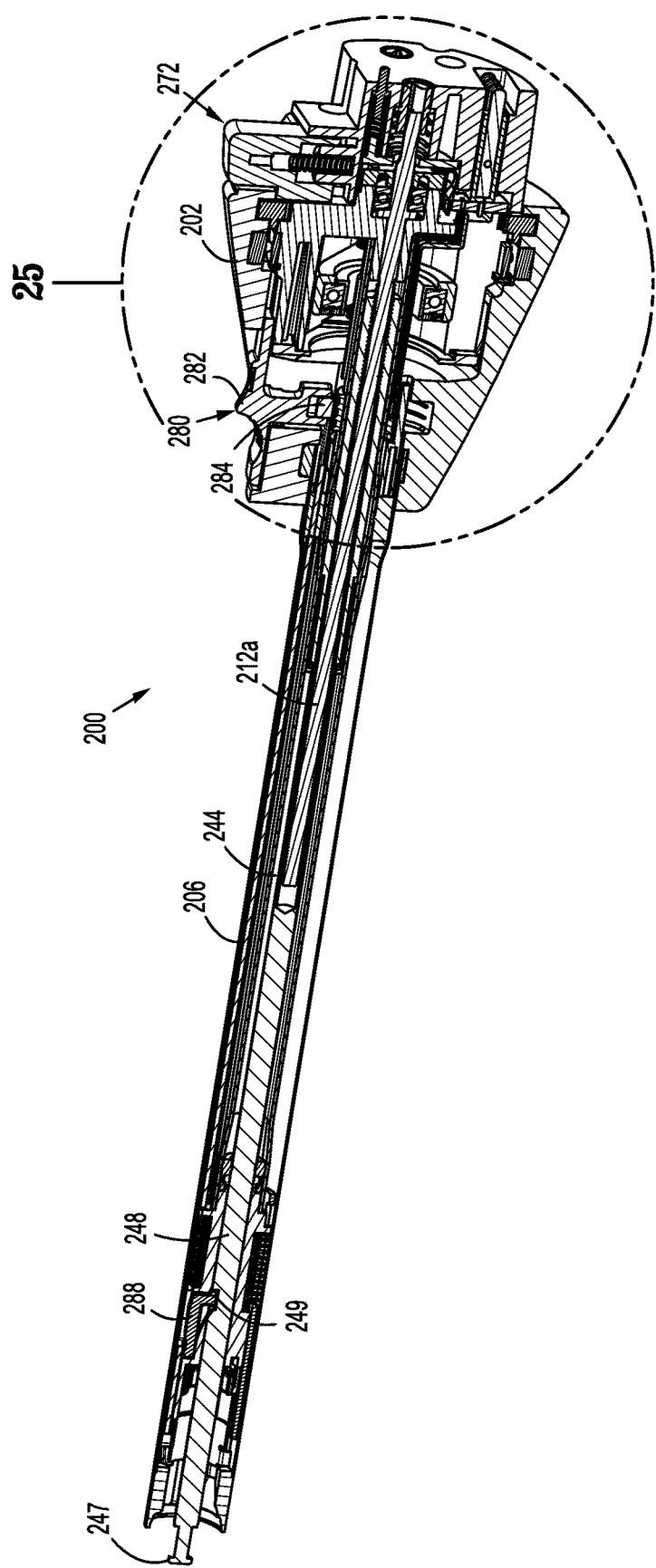
FIG. 24 is a cross-sectional view as taken along section line 24-24 of FIG. 2B.
Figure 25:
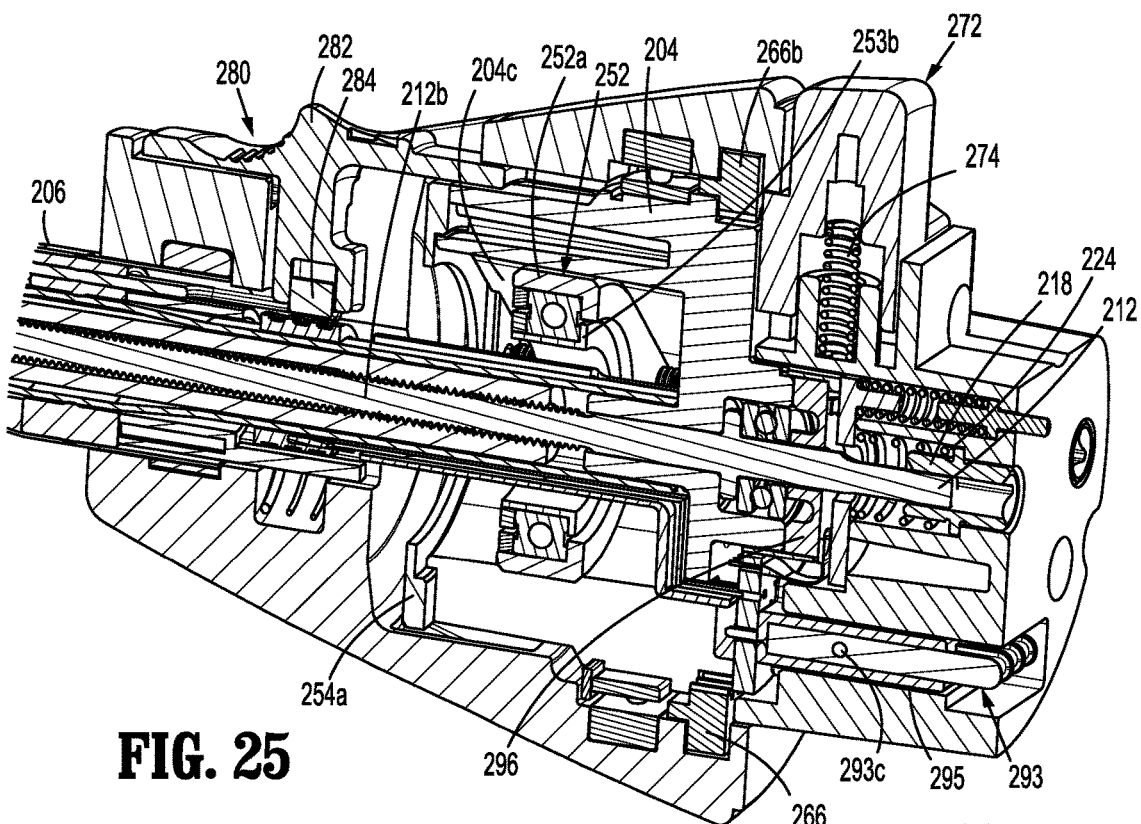
FIG. 25 is an enlarged view of the indicated area of detail of FIG. 24.
Figure 26:
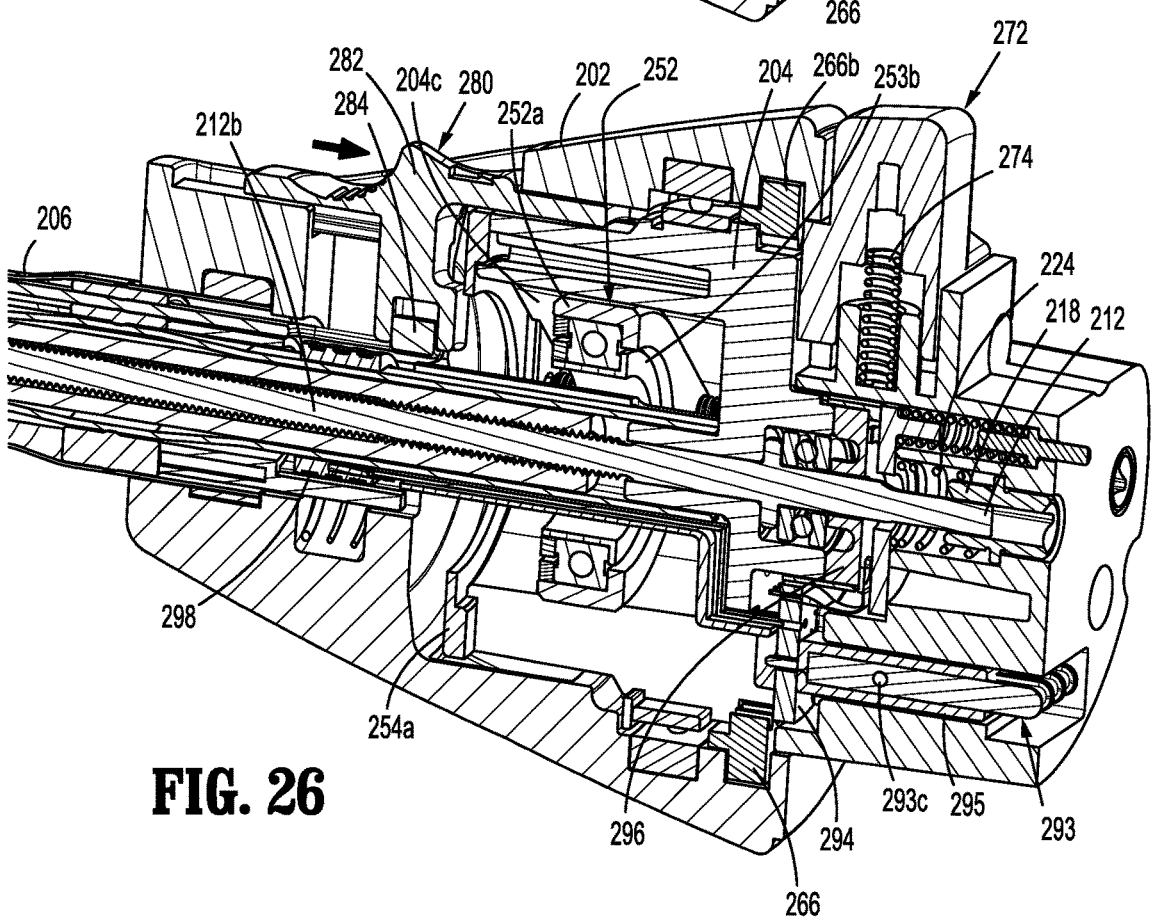
FIG. 26 is an enlarged view of the indicated area of detail of FIG. 24, illustrating a lock button being actuated in a proximal direction.
Figure 27:
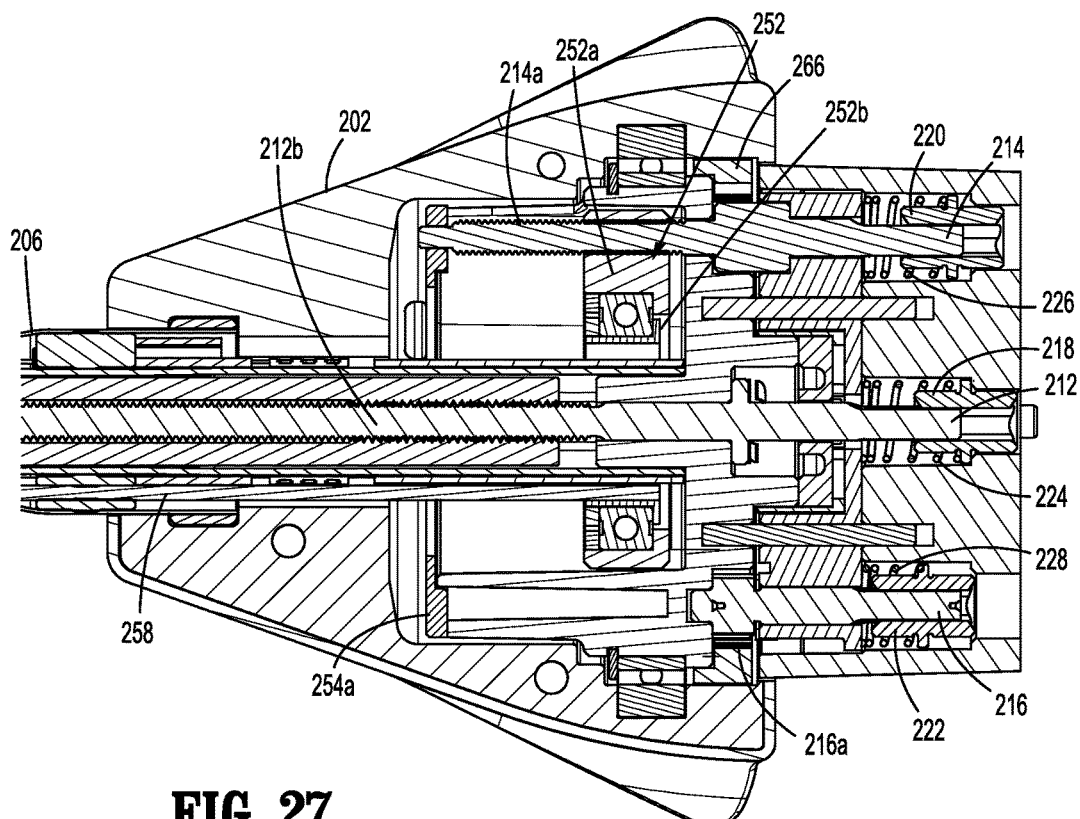
FIG. 27 is a cross-sectional view as taken along section line 27-27 of FIG. 2B.
Figure 28:
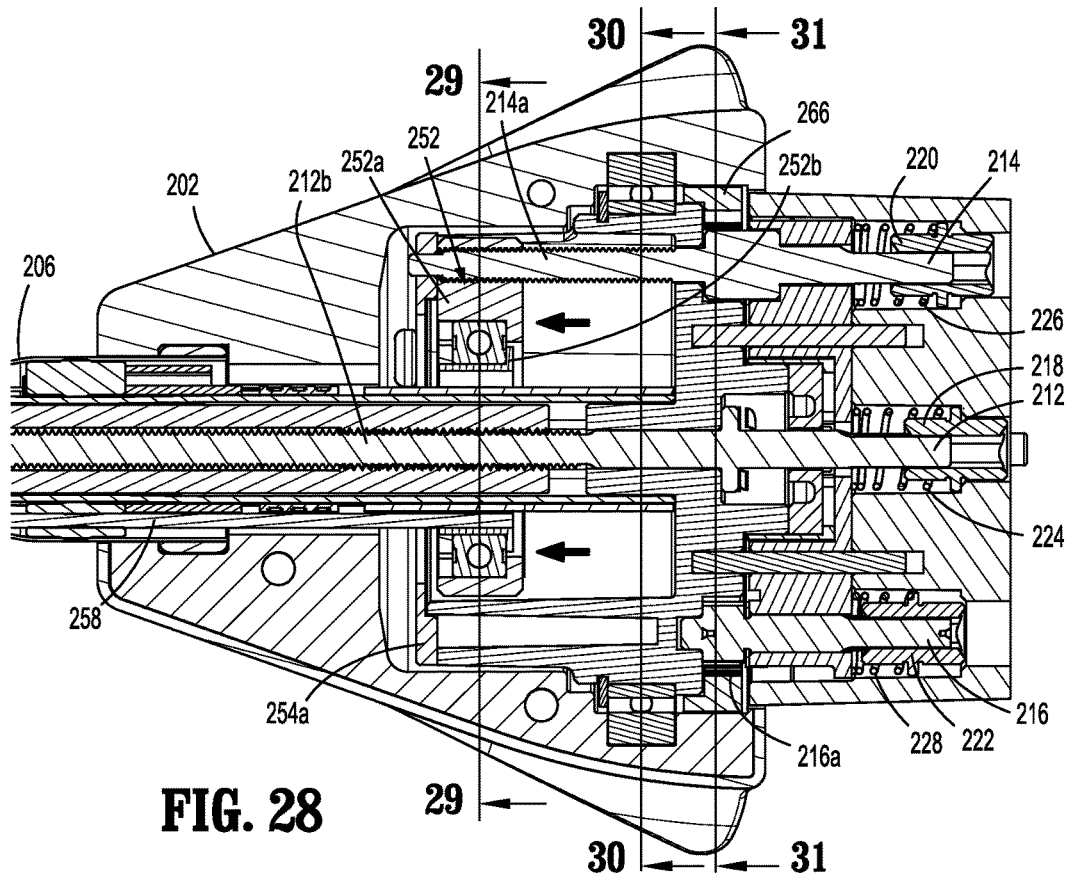
FIG. 28 is a cross-sectional view as taken along section line 27-27 of FIG. 2B, illustrating actuation of the articulation assembly in a distal direction.
Figure 31:
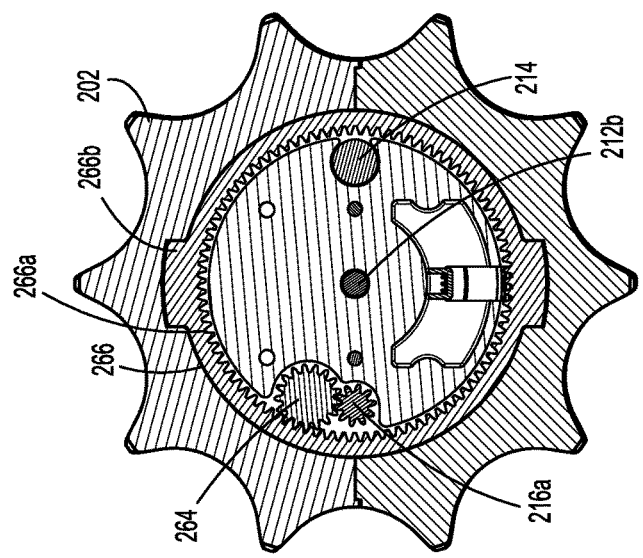
FIG. 31 is a cross-sectional view as taken along section line 31-31 of FIG. 28.
Figure 30:
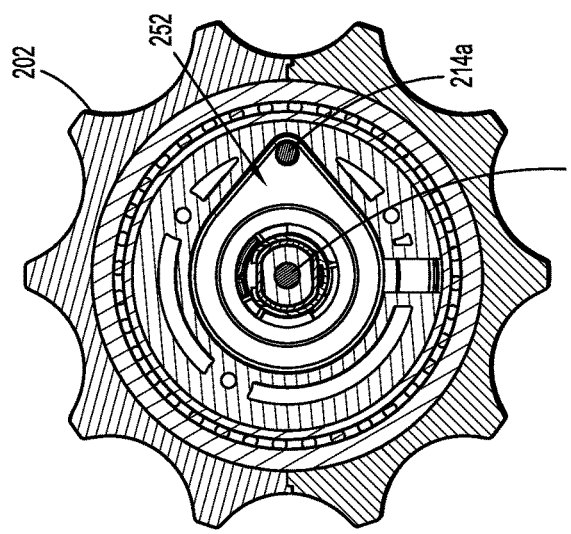
FIG. 30 is a cross-sectional view as taken along section line 30-30 of FIG. 28.
Figure 29:
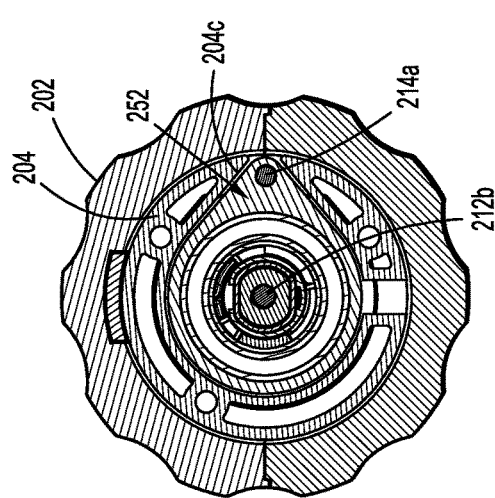
FIG. 29 is a cross-sectional view as taken along section line 29-29 of FIG. 28.
Figure 32:
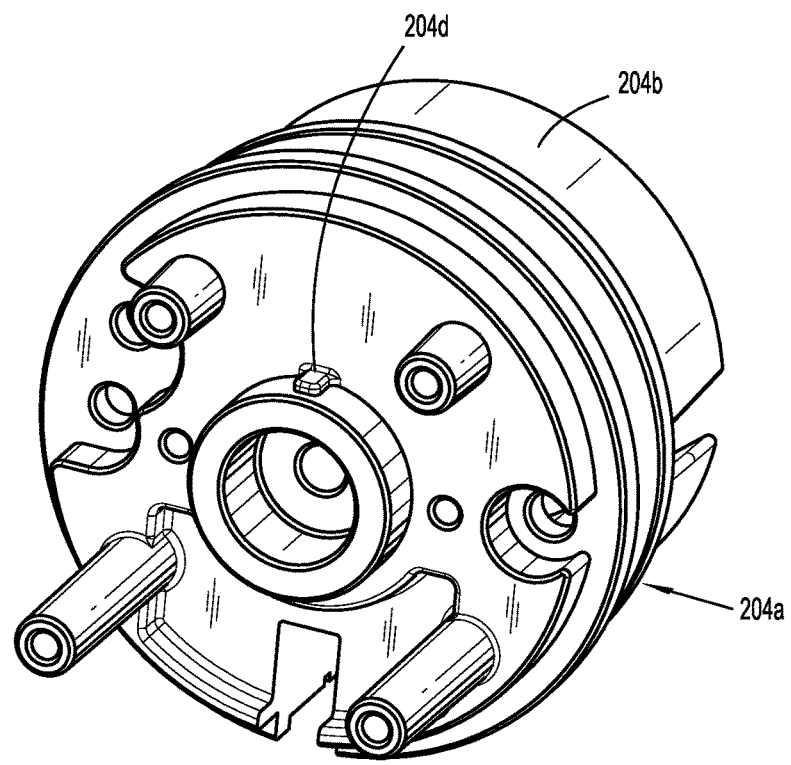
FIG. 32 is a rear, perspective view of a proximal inner housing hub according to the present disclosure.
Figure 33:
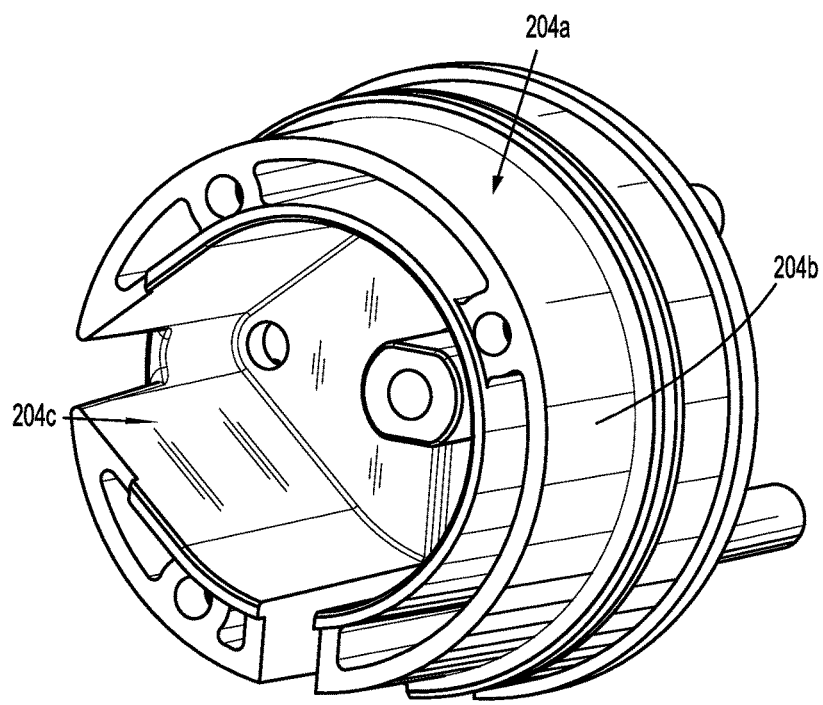
FIG. 33 is a front, perspective view of the proximal inner housing hub of FIG. 32.
Figure 34:
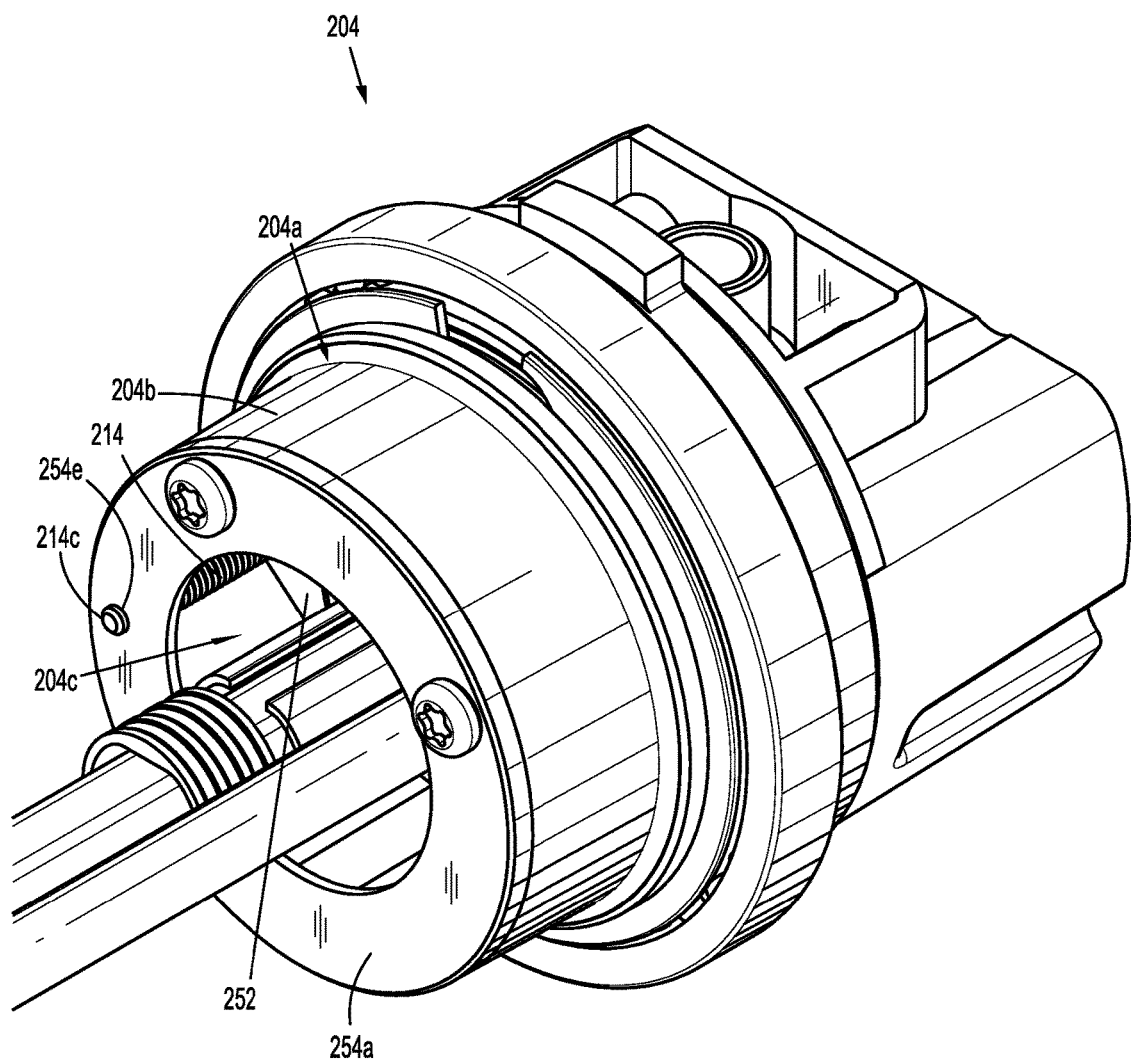
FIG. 34 is a front, perspective view of the proximal inner housing hub of FIGS. 32 and 33 illustrating a first and a second force/rotation transmitting/converting assembly and a reinforcing assembly associated therewith.
Figure 35:
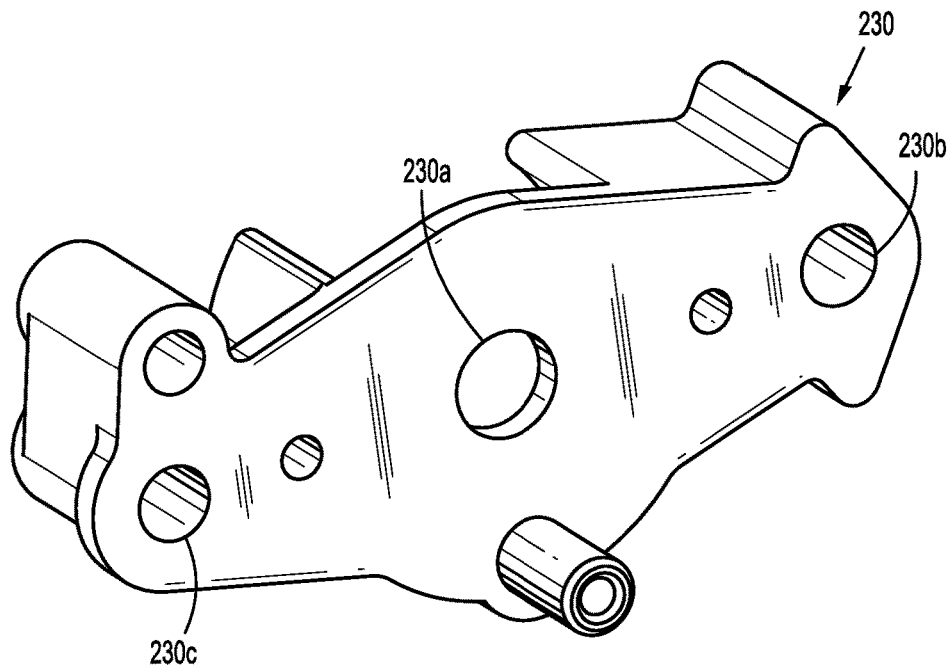
FIG. 35 is a front, perspective view of a plate bushing of the proximal inner housing assembly of the present disclosure.
Figure 36:
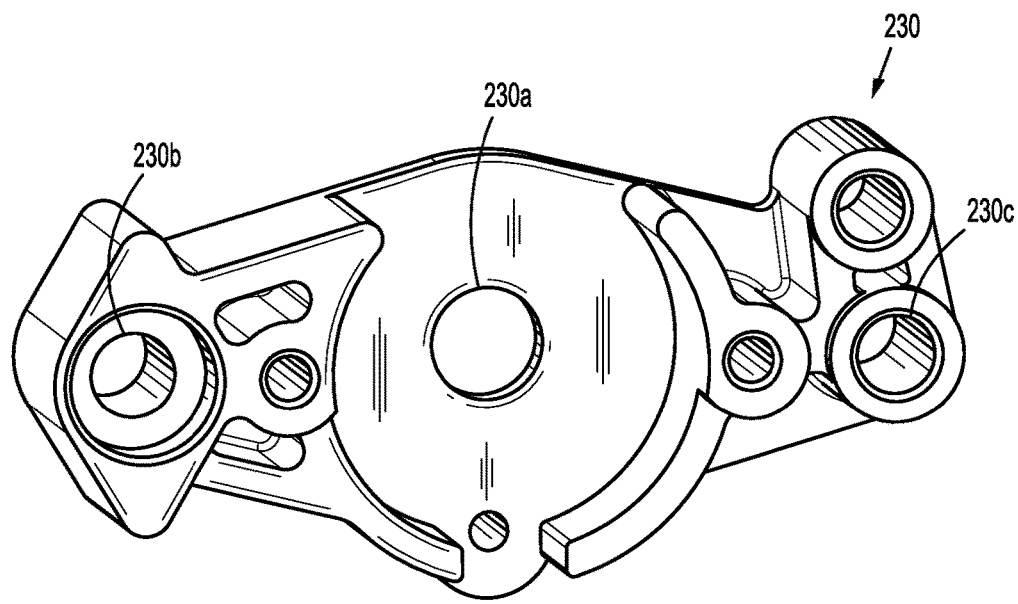
FIG. 36 is a rear, perspective view of the plate bushing of FIG. 35.
Figure 37:
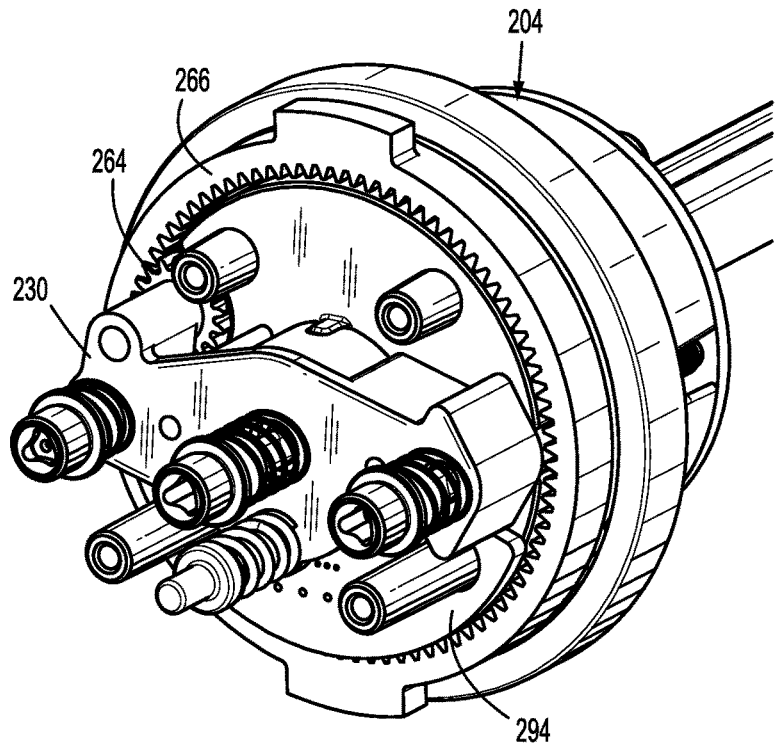
FIG. 37 is a rear, perspective view of the proximal inner housing assembly illustrating the plate bushing of FIGS. 35 and 36 attached thereto.

With particular reference to FIG. 15, slip ring cannula 700 includes a base portion 702, a longitudinal slit 710, a longitudinal wire track 720, a radially-extending post 730 adjacent a proximal portion of base portion 702, and a finger 740 extending proximally from a radially-outward portion of post 730. Referring now to FIG. 15 which illustrates slip ring cannula 700, and FIGS. 84-85 which show a different embodiment of a slip ring cannula 700b, longitudinal slit 710 is formed in base portion 702 and is configured to facilitate assembly between slip ring cannula 700 and a core tube 207 (see FIGS. 82 and 83) of outer tube 206 (see FIG. 2A). Wire track 720 extends along base portion 702 radially opposite from longitudinal slit 710 and provides a path for wires 299 to extend within slip ring cannula 700 and between slip ring 298 and circuit board 294. Post 730 is configured to abut an inner wall of hub 204a of inner housing assembly 204 to maintain the radial position of slip ring cannula 700 with respect to housing assembly 204. Finger 740 is configured such that when slip ring cannula 700 is engaged with housing assembly 204, hooks 742 of finger 740 hook around a proximal wall 205 of housing assembly 204 to maintain the longitudinal position of slip ring cannula 700 with respect to housing assembly 204 (see FIG. 85).

Turning now to FIGS. 80-83, another embodiment of a slip ring cannula 700a is illustrated. Slip ring cannula 700a includes a disc-like base portion 702a, a slit 710a extending radially outward from a central aperture 704a, a wire track 720a, and a pair of flexible tabs 730a extending proximally from an outer periphery of base portion 702a. Slip ring cannula 700a is configured such that core tube 207 extends through central aperture 704a. As shown with particular regard to FIGS. 81 and 83, wires 299 extend through wire track 720a as wires 299 extend between slip ring 298 and circuit board 294 (see FIG. 12A, for example). Each flexible tab 730a includes a one-way ratchet 732a which is configured to engage a radial wall 204e of hub 204a (see FIG. 82). Engagement between flexible tabs 730a and radial wall 204e of hub 204a provides linear stabilization of slip ring cannula 700a with respect to housing assembly 204. Engagement between radially outward surfaces 734a of flexible tabs 730a and radial wall 204e of hub 204a provides radial stabilization of slip ring cannula 700a with respect to housing assembly 204.

Figure 84:
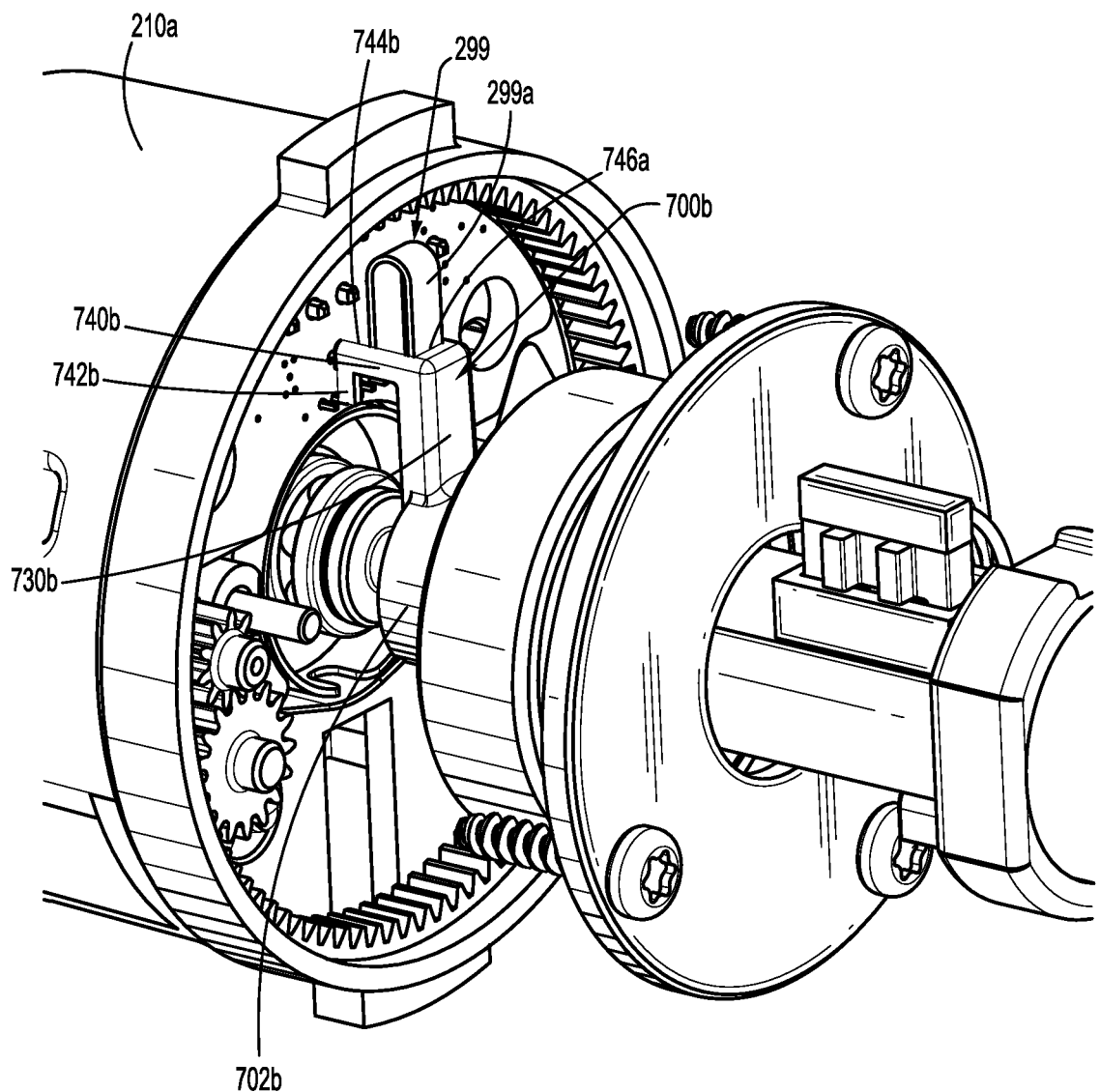
FIG. 84 is a perspective view of a portion of the adapter assembly including an alternate embodiment of a slip ring contact holder in accordance with the present disclosure.
Figure 85:
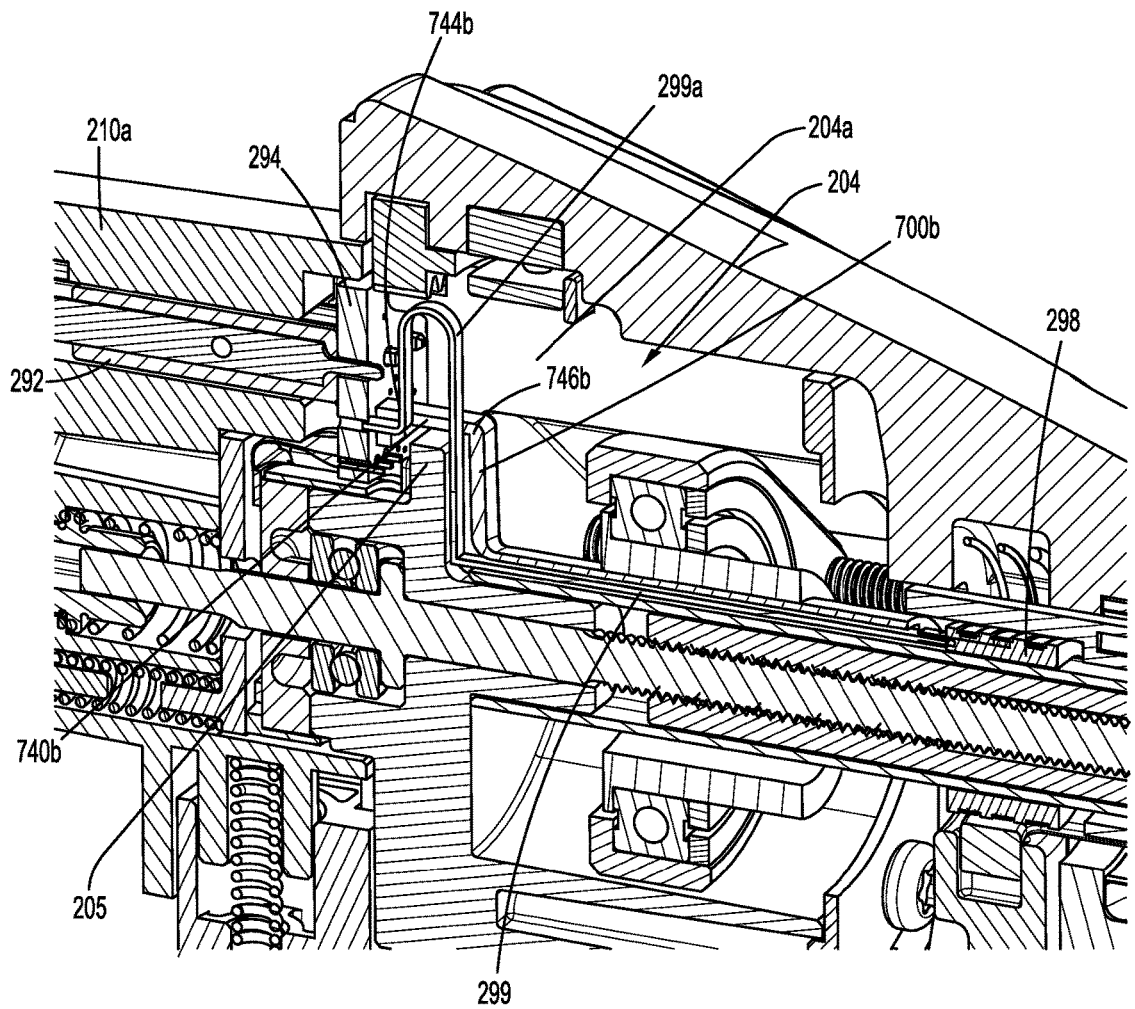
FIG. 85 is a cross-sectional view of the adapter assembly including the slip ring contact holder of FIG. 84.

With reference to FIGS. 84 and 85, a third embodiment of slip ring cannula 700b is shown. Slip ring cannula 700b is similar to slip ring cannula 700, discussed above with reference to FIG. 15, but also includes a proximal passageway 744b and a distal passageway 746b extending through finger 740b. Proximal and distal passageways 744b, 746b are configured to allow wires 299 and/or a cable to be threaded therethrough, as shown in FIGS. 84 and 85. It is envisioned that to facilitate assembling proximal electrical assembly 290b around hub 204a of housing assembly 204, an extra length 299a of wires 299 would be helpful. This extra length 299a of wires 299 would then be directed within adapter assembly 200 after circuit board 294 and strain gauge 296 (see FIG. 12A) have been assembled. As shown in FIG. 85, extra length 299a of wires 299 are able to fit radially outward of proximal wall 205 of hub 204a of housing assembly 204.

As can be appreciated, each embodiment of slip ring cannula 700, 700a and 700b, when assembled, will hold wires 299 taut in a linear manner with respect to slip ring 298, and will prevent articulation bearing assembly 252 (FIG. 25) from contacting wires 299. It is further envisioned that wires 299 are made from a material that is elastic and/or autoclavable. It is envisioned that these stretchable wires 299 are assembled over slip ring 298 in a first, non-stretched position. These wires 299 would then stretch toward a second position when slip ring 298 is assembled onto core tube 207. Here, wires 299 would be thin enough as to not interfere with articulation bearing assembly 252.

In operation, when a button of surgical device 100 is activated by the user, the software checks predefined conditions. If conditions are met, the software controls the motors and delivers mechanical drive to the attached surgical stapler, which can then open, close, rotate, articulate or fire depending on the function of the pressed button. The software also provides feedback to the user by turning colored lights on or off in a defined manner to indicate the status of surgical device 100, adapter assembly 200 and/or loading unit 300.

Reference may be made to U.S. Patent Publication No. 2009/0314821, filed on Aug. 31, 2009, entitled "TOOL ASSEMBLY FOR A SURGICAL STAPLING DEVICE" for a detailed discussion of the construction and operation of loading unit 300, as illustrated in FIGS. 1 and 48.

Any of the components described herein may be fabricated from either metals, plastics, resins, composites or the like taking into consideration strength, durability, wearability, weight, resistance to corrosion, ease of manufacturing, cost of manufacturing, and the like.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. An adapter assembly for selectively interconnecting a surgical loading unit that is configured to perform a function and a surgical device that is configured to actuate the loading unit, the loading unit including an axially translatable drive member, and the surgical device including a rotatable drive shaft, the adapter assembly comprising:
   a housing configured and adapted for connection with the surgical device and to be in operative communication with each rotatable drive shaft of the surgical device;
   an outer tube having a proximal end supported by the housing and a distal end configured and adapted for connection with the loading unit, wherein the distal end of the outer tube is in operative communication with each of the at least one axially translatable drive member of the loading unit;
   at least one force/rotation transmitting/converting assembly for interconnecting a respective one drive shaft of the surgical device and a respective one axially translatable drive member of the loading unit; and
   an electrical assembly supported at least partially within at least one of the housing and the outer tube, the electrical assembly including:
      a proximal electrical assembly configured to electrically communicate with the surgical device, the proximal electrical assembly being rotatably fixed with respect to the surgical device, the proximal electrical assembly including a plurality of electrical contact rings disposed around a slip ring; and
      a distal electrical assembly disposed in electrical communication with the loading unit, the distal electrical assembly being rotatable with respect to the proximal electrical assembly, the distal electrical assembly including a plurality of electrical contacts disposed in mechanical cooperation with a contact housing, each electrical contact configured to contact and maintain an electrical connection with one of the plurality of electrical contact rings of the proximal electrical assembly during rotation of the distal electrical assembly with respect to the proximal electrical assembly.

2. The adapter assembly according to claim 1, wherein each electrical contact of the distal electrical assembly is curved along at least a majority of its length.

3. The adapter assembly according to claim 1, wherein each electrical contact of the distal electrical assembly includes a continuous curve in a first direction, and wherein the plurality of electrical contact rings of the proximal electrical assembly are curved in a second direction, the first and second directions being opposite from each other.

4. The adapter assembly according to claim 1, wherein each electrical contact of the distal electrical assembly includes a leg and a foot, the leg extending from the contact housing, the foot extending at an angle from the leg, a portion of the foot configured to contact one of the plurality of electrical contact rings, wherein the angle is between about 100° and about 160°.

5. The adapter assembly according to claim 1, wherein each electrical contact of the distal electrical assembly includes a leg and two feet, the leg extending from the contact housing, each foot extending at an angle from the leg in opposite directions, a portion of each foot configured to contact one of the plurality of electrical contact rings, wherein the angle is between about 100° and about 160°.

6. The adapter assembly according to claim 1, wherein each electrical contact of the distal electrical assembly includes a leg, an ankle and an arcuate foot, the leg extending from the contact housing, the ankle extending at a first angle from the leg, and the arcuate foot extending at a second angle from the ankle, at least two portions of the arcuate foot are configured to contact one of the plurality of electrical contact rings, wherein the first angle is between about 150° and about 175°, and wherein the second angle is between about 10° and about 60°.

7. The adapter assembly according to claim 6, wherein the arcuate foot includes a radius of curvature that is one of less than and equal to a radius of curvature of the plurality of electrical contact rings.

8. The adapter assembly according to claim 1, wherein each electrical contact of the distal electrical assembly includes a leg, two feet extending from the leg in an opposite directions, and a flexible contact extending between the two feet, at least a portion of the flexible contact is configured to contact one of the plurality of electrical contact rings.

9. The adapter assembly according to claim 8, wherein the flexible contact is movable with respect to at least one foot.

10. The adapter assembly according to claim 1, wherein each electrical contact of the distal electrical assembly includes a leg and a ring, the leg extending from the contact housing, the ring extending from the leg, the ring configured to contact one of the plurality of electrical contact rings in an arc of greater than 180°.

11. The adapter assembly according to claim 10, wherein the ring forms between about 180° and about 360° of a circle.

12. The adapter assembly according to claim 1, wherein the contact housing includes a proximal leg configured to engage a proximal-most edge of the slip ring, and a distal leg configured to engage a distal-most edge of the slip ring.

13. The adapter assembly according to claim 12, wherein each leg of the contact housing includes a stepped portion, at least part of the stepped portion configured to engage a radially-outermost portion of the slip ring.

14. The adapter assembly according to claim 1, wherein the distal electrical assembly further includes a guide configured to help maintain a position of the contact housing with respect to the slip ring.

15. The adapter assembly according to claim 14, wherein the guide is configured to help maintain a longitudinal position and a radial position of the contact housing with respect to the slip ring.

16. The adapter assembly according to claim 14, wherein the guide includes an opening for receiving at least a portion of the contact housing therein, and wherein the guide includes a flexible member for extending between a pair of projections of the contact housing and for abutting a radially-outer surface of at least one of the projections of the contact housing.

17. The adapter assembly according to claim 14, wherein the guide includes an opening for receiving at least a portion of the contact housing therein, and wherein the guide includes a first post extending adjacent a first portion of the opening for extending between a pair of projections of the contact housing.

18. The adapter assembly according to claim 17, wherein the guide includes a second post extending adjacent a second portion of the opening for engaging a portion of the contact housing, the first portion and the second portion being on opposite sides of the opening.

19. The adapter assembly according to claim 14, wherein the guide includes an opening for receiving at least a portion of the contact housing therein, wherein the contact housing includes at least one projection, and wherein the guide includes at least one flexible tab for engaging a radially-outer surface of the at least one projection of the contact housing.

20. The adapter assembly according to claim 14, wherein the guide includes an opening for receiving at least a portion of the contact housing therein, wherein the contact housing includes at least two projections, and wherein the guide includes at least two flexible tabs, each flexible tab configured for engaging a radially-outer surface of one of the at least two projections of the contact housing.

\* \* \* \* \*